United States Patent
Xiao et al.

(10) Patent No.: US 11,325,982 B2
(45) Date of Patent: May 10, 2022

(54) BIPARATOPIC AND MULTIPARATOPIC ANTIBODIES WITH COMMON LIGHT CHAIN AND METHOD OF USE

(71) Applicants: XUANZHU BIOPHARMACEUTICAL CO., LTD., Shijiazhuang (CN); BEIJING XUANZHU COMBIO CO., LTD., Beijing (CN)

(72) Inventors: Shouhua Xiao, Foster City, CA (US); Xiaodong Zhu, San Francisco, CA (US)

(73) Assignees: XUANZHU BIOPHARMACEUTICAL CO., LTD., Shijiazhuang (CN); BEIJING XUANZHU COMBIO CO., LTD., Beijing (CN)

( * ) Notice: Subject to any disclaimer, the term of this patent is extended or adjusted under 35 U.S.C. 154(b) by 268 days.

(21) Appl. No.: 16/603,711

(22) PCT Filed: Apr. 9, 2018

(86) PCT No.: PCT/US2018/026759
§ 371 (c)(1),
(2) Date: Oct. 8, 2019

(87) PCT Pub. No.: WO2018/191188
PCT Pub. Date: Oct. 18, 2018

(65) Prior Publication Data
US 2020/0140568 A1 May 7, 2020

Related U.S. Application Data

(60) Provisional application No. 62/483,456, filed on Apr. 9, 2017.

(51) Int. Cl.
*C07K 16/00* (2006.01)
*C07K 16/32* (2006.01)

(52) U.S. Cl.
CPC .......... *C07K 16/32* (2013.01); *C07K 2317/24* (2013.01); *C07K 2317/31* (2013.01); *C07K 2317/526* (2013.01); *C07K 2317/55* (2013.01); *C07K 2317/565* (2013.01); *C07K 2317/732* (2013.01); *C07K 2317/76* (2013.01); *C07K 2317/92* (2013.01)

(58) Field of Classification Search
CPC ................ C07K 16/32; C07K 2317/24; C07K 2317/31; C07K 2317/55; C07K 2317/565; C07K 2317/732; C07K 2317/76; C07K 2317/92
See application file for complete search history.

(56) References Cited

U.S. PATENT DOCUMENTS

| | | |
|---|---|---|
| 8,975,382 B2 | 3/2015 | Revets et al. |
| 2013/0266564 A1 | 10/2013 | Jaramillo et al. |
| 2015/0232573 A1* | 8/2015 | Cheong .................. C07K 16/32 424/135.1 |
| 2015/0307594 A1 | 10/2015 | Corper et al. |
| 2019/0031782 A1* | 1/2019 | Xu ....................... G01N 33/577 |

FOREIGN PATENT DOCUMENTS

| | | | |
|---|---|---|---|
| CN | 105820251 A | | 8/2016 |
| EP | 3243840 A1 | | 11/2017 |
| WO | WO201108449 | * | 7/2011 |
| WO | WO-2015091738 A1 | | 6/2015 |
| WO | WO 2016/110267 | * | 7/2016 |
| WO | WO-2016110267 A1 | | 7/2016 |

OTHER PUBLICATIONS

International Search Report and Written Opinion of the International Searching Authority, issued in PCT/US2018/026759, dated Aug. 24, 2018; ISA/US.
Supplemental European Search Report issued in related European Application No. 18784656, dated Nov. 11, 2020.
Office Action in related case CN 2018800004095.0 dated Mar. 3, 2021.

* cited by examiner

*Primary Examiner* — Lei Yao
(74) *Attorney, Agent, or Firm* — Harness, Dickey & Pierce, P.L.C.

(57) ABSTRACT

The present invention relates to bispecific or multi-specific antibody molecules with two or more paratopes. At least one paratope is Fv or scFv, while the other paratope is in a mono-valent or bivalent Fab. These novel molecules also have an Fc moiety that allows extended half-life in vivo.

18 Claims, 16 Drawing Sheets
Specification includes a Sequence Listing.

FIG. 1

```
                 1         10        20        30        40
Pertuzumab       D I Q M T Q S P S S L S A S V G D R V T I T C K A S Q D V S I G V A W Y Q Q K P
                 D I Q M T Q S P S S L S A S V G D R V T I T C + A S Q D V +       V A W Y Q Q K P
Trastuzumab      D I Q M T Q S P S S L S A S V G D R V T I T C R A S Q D V N T A V A W Y Q Q K P
                                                               └─────── CDR-L1 ───────┘

41        50        52  54  56          60        70        80
Pertuzumab       G K A P K L L I Y S A S Y R Y T G V P S R F S G S G S G T D F T L T I S S L Q P
                 G K A P K L L I Y S A S + + Y +     G V P S R F S G S G S G T D F T L T I S S L Q P
Trastuzumab      G K A P K L L I Y S A S F L Y S G V P S R F S G S R S G T D F T L T I S S L Q P
                                       └── CDR-L2 ──┘

81        90  92  94  96        100       107
Pertuzumab       E D F A T Y Y C Q Q Y Y I Y P Y T F G Q G T K V E I K        SEQ ID NO:1
                 E D F A T Y Y C Q Q + Y +       P   T F G Q G T K V E I K    Consensus
Trastuzumab      E D F A T Y Y C Q Q H Y T T P P T F G Q G T K V E I K        SEQ ID NO:5
                                   └───── CDR-L3 ─────┘
```

FIG. 2

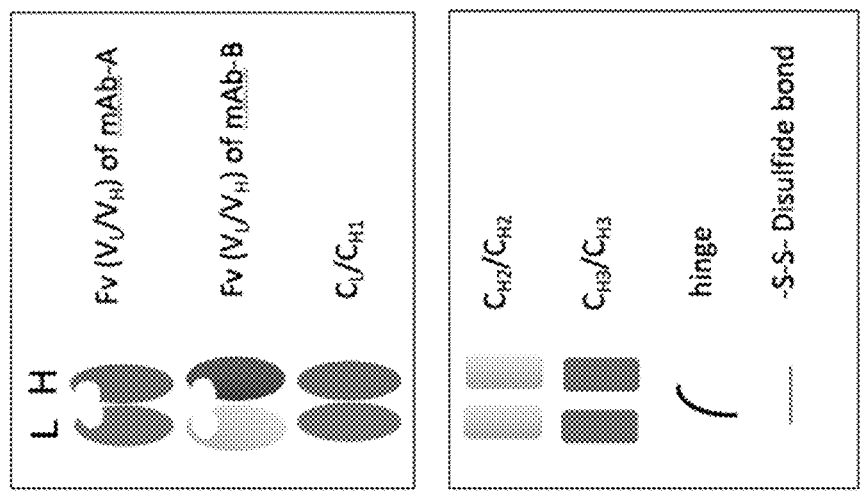
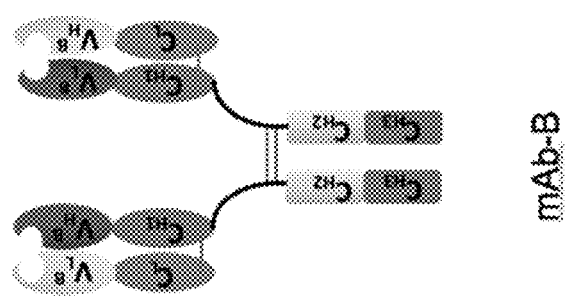
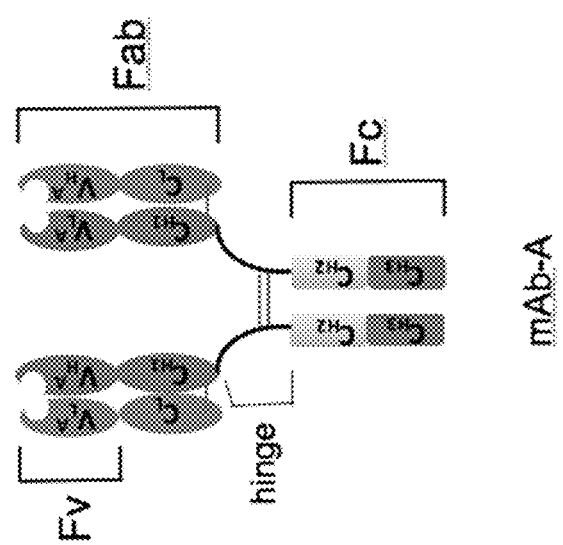
FIG. 3

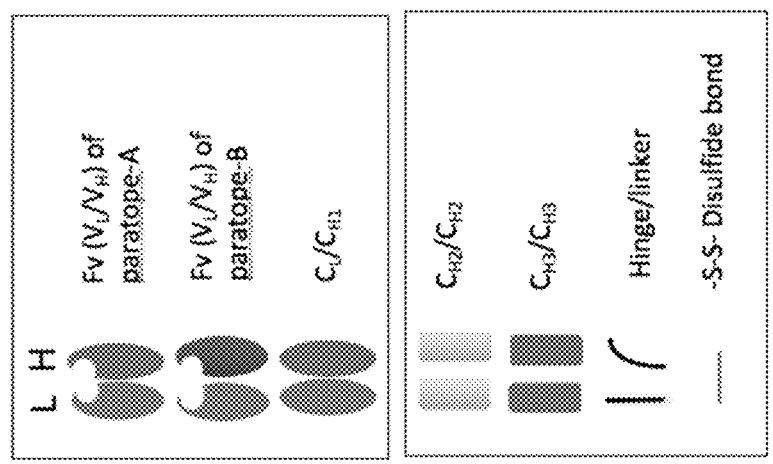
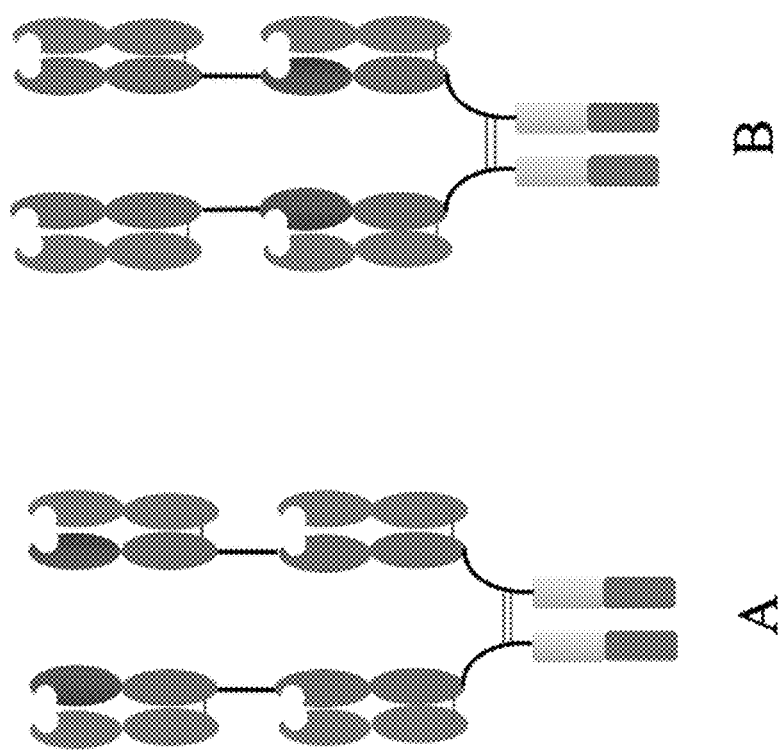
FIG. 4

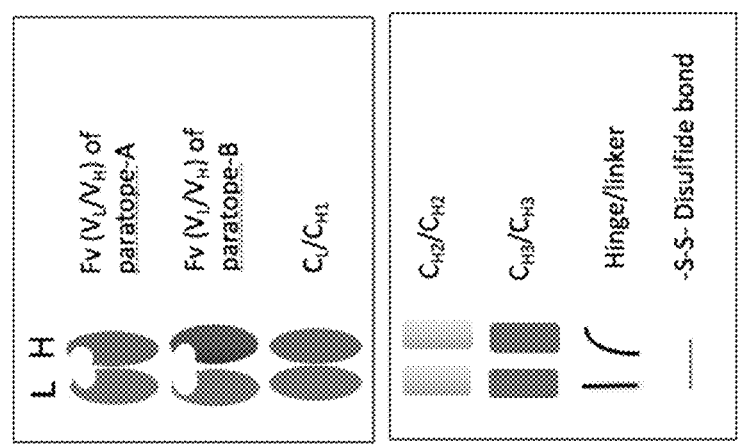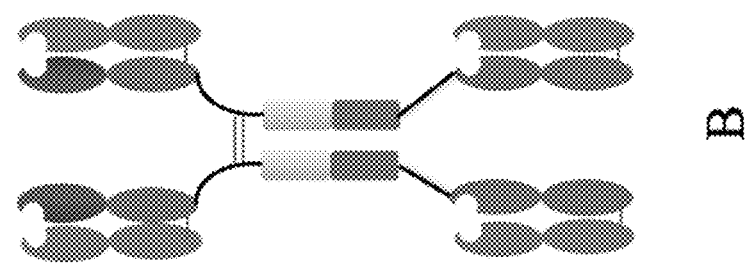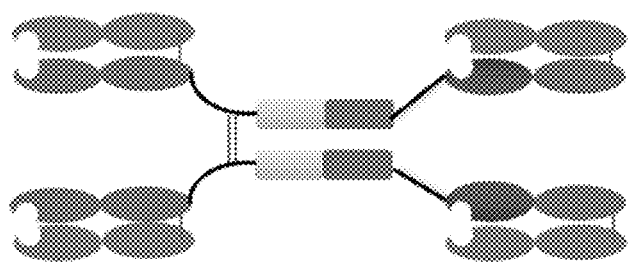
FIG. 5

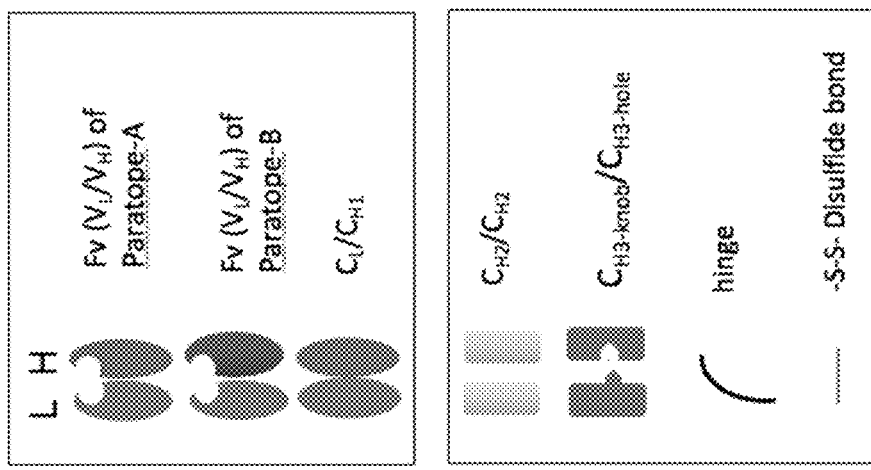
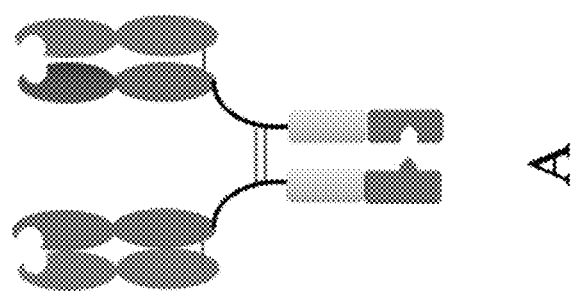
A
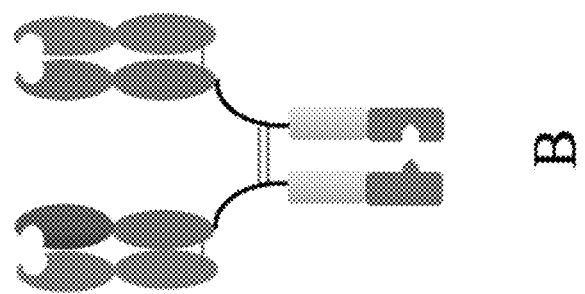
B
FIG. 6

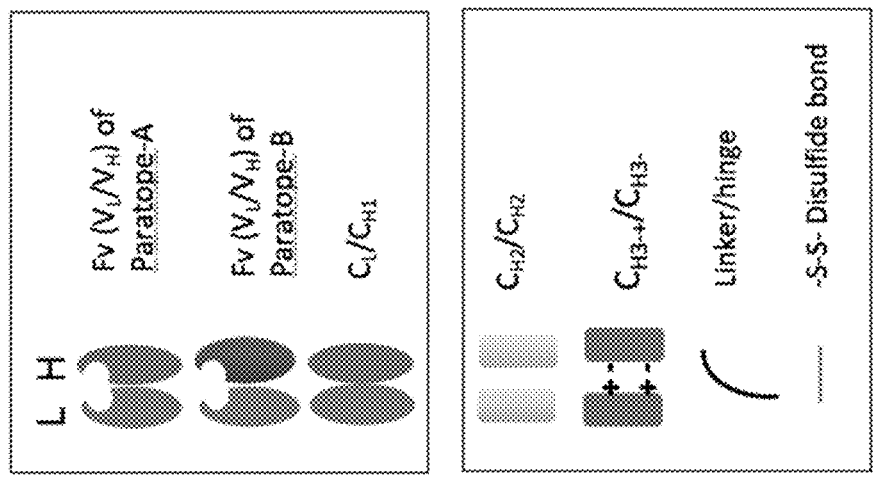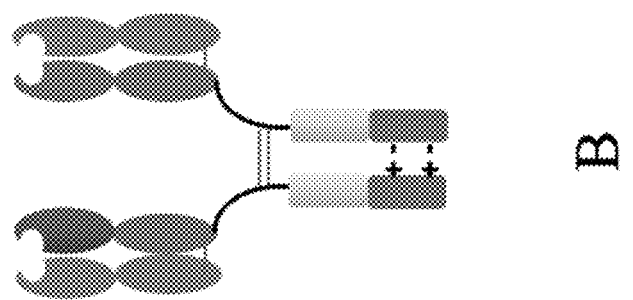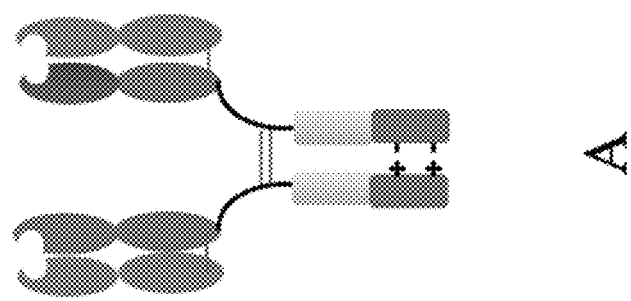
FIG. 7

| mAb # | EC50(ng/ml) | mAb # | EC50(ng/ml) |
|---|---|---|---|
| T1 | 546.0 | T54 | 255.1 |
| T22 | 210.7 | T55 | 279.7 |
| T51 | 386.5 | T56 | 174.1 |
| T52 | 241.8 | T57 | 377.0 |
| T53 | 351.7 | T58 | 199.9 |

SEQUENCE LISTING

```
<160> NUMBER OF SEQ ID NOS: 44

<210> SEQ ID NO 1
<211> LENGTH: 107
<212> TYPE: PRT
<213> ORGANISM: Artificial Sequence
<220> FEATURE:
<223> OTHER INFORMATION: pertuzumab light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
```

```
                    100                 105

<210> SEQ ID NO 2
<211> LENGTH: 214
<212> TYPE: PRT
<213> ORGANISM: Artificial Sequence
<220> FEATURE:
<223> OTHER INFORMATION: pertuzumab light chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 119
<212> TYPE: PRT
<213> ORGANISM: Artificial Sequence
<220> FEATURE:
<223> OTHER INFORMATION: pertuzumab heavy chain variable region

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80
```

```
Leu Gln Met Asn Ser Leu Arg Ala Glu Asp Thr Ala Val Tyr Tyr Cys
                    85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 4
<211> LENGTH: 448
<212> TYPE: PRT
<213> ORGANISM: Artificial Sequence
<220> FEATURE:
<223> OTHER INFORMATION: pertuzumab heavy chain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 5
<211> LENGTH: 107
<212> TYPE: PRT
<213> ORGANISM: Artificial Sequence
<220> FEATURE:
<223> OTHER INFORMATION: trastuzumab light chain variable region

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 6
<211> LENGTH: 214
<212> TYPE: PRT
<213> ORGANISM: Artificial Sequence
<220> FEATURE:
<223> OTHER INFORMATION: trastuzumab light chain

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 120
<212> TYPE: PRT
<213> ORGANISM: Artificial Sequence
<220> FEATURE:
<223> OTHER INFORMATION: trastuzumab heavy chain variable region

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 8
<211> LENGTH: 451
<212> TYPE: PRT
<213> ORGANISM: Artificial Sequence
<220> FEATURE:
<223> OTHER INFORMATION: trastuzumab heavy chain

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
               35                  40                  45
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

```
<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
                85                  90                  95

Thr Phe Gly Gly Gly Thr Lys Val Asp Ile Lys
            100                 105

<210> SEQ ID NO 10
<211> LENGTH: 214
<212> TYPE: PRT
<213> ORGANISM: Homo sapiens

<400> SEQUENCE: 10

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
                85                  90                  95

Thr Phe Gly Gly Gly Thr Lys Val Asp Ile Lys Gly Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 11
<211> LENGTH: 116
<212> TYPE: PRT
<213> ORGANISM: Homo sapiens

<400> SEQUENCE: 11

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser
        115

<210> SEQ ID NO 12
<211> LENGTH: 446
<212> TYPE: PRT
<213> ORGANISM: Homo sapiens

<400> SEQUENCE: 12

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

```
Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 13
<211> LENGTH: 708
<212> TYPE: PRT
<213> ORGANISM: Artificial Sequence
<220> FEATURE:
<223> OTHER INFORMATION: Biparatopic antibody construct HC11

<400> SEQUENCE: 13

Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30

Pro Gly Ser Leu Arg Leu Ser Cys Ala Ala Ser Gly Phe Thr Phe
        35                  40                  45

Ala Asp Tyr Thr Met Asp Trp Val Arg Gln Ala Pro Gly Lys Gly Leu
        50                  55                  60

Glu Trp Val Ala Asp Val Asn Pro Asn Ser Gly Gly Ser Ile Tyr Asn
65                  70                  75                  80

Gln Arg Phe Lys Gly Arg Phe Thr Leu Ser Val Asp Arg Ser Lys Asn
            85                  90                  95

Thr Leu Tyr Leu Gln Met Asn Ser Leu Arg Ala Glu Asp Thr Ala Val
            100                 105                 110

Tyr Tyr Cys Ala Arg Asn Leu Gly Pro Ser Phe Tyr Phe Asp Tyr Trp
            115                 120                 125
```

```
Gly Gln Gly Thr Leu Val Thr Val Ser Ser Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Lys Val Glu Pro Lys Ser
225                 230                 235                 240

Cys Asp Lys Gly Gly Gly Ser Gly Gly Gly Ser Gly Gly Gly Ser Gly
                245                 250                 255

Gly Gly Glu Val Gln Leu Val Glu Ser Gly Gly Gly Leu Val Gln Pro
            260                 265                 270

Gly Gly Ser Leu Arg Leu Ser Cys Ala Ala Ser Gly Phe Asn Ile Lys
            275                 280                 285

Asp Thr Tyr Ile His Trp Val Arg Gln Ala Pro Gly Lys Gly Leu Glu
            290                 295                 300

Trp Val Ala Arg Ile Tyr Pro Thr Thr Gly Tyr Thr Arg Tyr Ala Asp
305                 310                 315                 320

Ser Val Lys Gly Arg Phe Thr Ile Ser Ala Asp Thr Ser Lys Asn Thr
                325                 330                 335

Ala Tyr Leu Gln Met Asn Ser Leu Arg Ala Glu Asp Thr Ala Val Tyr
            340                 345                 350

Tyr Cys Ser Arg Trp Gly Gly Ser Gly Phe Tyr Ala Met Asp Tyr Trp
            355                 360                 365

Gly Gln Gly Thr Leu Val Thr Val Ser Ser Ala Ser Thr Lys Gly Pro
            370                 375                 380

Ser Val Phe Pro Leu Ala Pro Ser Ser Lys Ser Thr Ser Gly Gly Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
                420                 425                 430

Ala Val Leu Gln Ser Ser Gly Leu Tyr Ser Leu Ser Ser Val Val Thr
            435                 440                 445

Val Pro Ser Ser Ser Leu Gly Thr Gln Thr Tyr Ile Cys Asn Val Asn
450                 455                 460

His Lys Pro Ser Asn Thr Lys Val Asp Lys Lys Val Glu Pro Lys Ser
465                 470                 475                 480

Cys Asp Lys Thr His Thr Cys Pro Pro Cys Pro Ala Pro Glu Leu Leu
                485                 490                 495

Gly Gly Pro Ser Val Phe Leu Phe Pro Pro Lys Pro Lys Asp Thr Leu
                500                 505                 510

Met Ile Ser Arg Thr Pro Glu Val Thr Cys Val Val Val Asp Val Ser
            515                 520                 525

His Glu Asp Pro Glu Val Lys Phe Asn Trp Tyr Val Asp Gly Val Glu
530                 535                 540
```

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Lys Val Ser Asn Lys Ala Leu Pro Ala Pro
            580                 585                 590

Ile Glu Lys Thr Ile Ser Lys Ala Lys Gly Gln Pro Arg Glu Pro Gln
        595                 600                 605

Val Tyr Thr Leu Pro Pro Ser Arg Asp Glu Leu Thr Lys Asn Gln Val
    610                 615                 620

Ser Leu Thr Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
        675                 680                 685

Leu His Glu Ala Leu His Asn His Tyr Thr Gln Lys Ser Leu Ser Leu
    690                 695                 700

Ser Pro Gly Lys
705

<210> SEQ ID NO 14
<211> LENGTH: 2146
<212> TYPE: DNA
<213> ORGANISM: Artificial Sequence
<220> FEATURE:
<223> OTHER INFORMATION: Biparatopic antibody construct HC11

<400> SEQUENCE: 14
gaattcgcca ccatgaactt tggcctgagc ctgattttc tcgtcctgat cctgaagggc      60
gtgcagtgtg aggtgcagct ggtggagagc ggcggcggcc tggtgcagcc cggcggcagc     120
ctgcgcctgt cctgcgccgc cagcggcttc acctttgccg actacaccat ggactgggtg     180
cgccaggctc ccggcaaggg cctggagtgg gtggccgacg tgaaccccaa cagcggcggc     240
agcatctaca accagcgctt caagggccgc ttcaccctga gcgtggaccg cagcaagaac     300
accctgtacc tgcagatgaa cagcctgcgc gccgaggaca ccgccgtgta ctactgcgcc     360
cgcaacctgg gccccagctt ctacttcgac tattgggggc agggcacccct ggtcaccgtg     420 agcagcgcta gcaccaaggg cccatccgtc ttccccctgg cacctcctc caagagcacc     480 tctggggca cagctgccct gggctgcctg gtcaaggact acttccccga accagtgacc     540
gtgtcctgga actcaggcgc cctgaccagc ggcgtgcaca ccttccctgc cgtcctgcag     600
tcctcaggac tctactccct cagcagcgtg gtgactgtgc cctctagcag cttgggcacc     660
cagacctaca tctgcaacgt gaatcacaag cccagcaaca ccaaggtgga caagaaagtt     720
gagcccaaat cttgtgacaa aggcggaggg agcggcggag gctccggagg cggcagcgga     780
ggcggagagg tgcagctggt ggagtctgga ggagggctgg tgcagccagg agggtccctg     840
agactgtctt gcgccgctag tggcttcaac atcaaggaca cctacatcca ctgggtgaga     900 caggccccg gaaaggcct ggagtgggtg gccaggatct accctaccac cggctacacc     960
aggtacgccg acagcgtgaa gggcaggttc accatcagcg ccgacaccag caagaacacc    1020
gcctacctgc agatgaacag cctgagggcc gaggacaccg ccgtgtacta ctgcagcaga    1080

```
tggggcggca gcggcttcta cgccatggac tactggggac agggcacact ggtcactgtg    1140
tctagtgcct caacaaaggg gcctagcgtg tttccactgg ctccctcaag caaaagcact    1200
tccggaggca ccgctgcact gggatgtctg gtgaaggact acttcccaga gcccgtcacc    1260
gtgtcttgga cagtggggc tctgaccagc ggagtccaca catttcctgc agtgctgcag    1320
tcctctggcc tgtacagcct gagttcagtg gtcacagtcc caagctcctc tctggggacc    1380
cagacatata tctgcaacgt gaatcacaag ccaagcaata ctaaagtcga caagaaagtg    1440
gagcccaaga gctgtgataa aactcatacc tgcccccctt gtcctgcacc agaactgctg    1500
ggaggaccat ccgtgttcct gtttccaccc aagcctaaag caccctgat gatttcccgc     1560
acacccgagg tcacttgcgt ggtcgtggac gtgtctcacg aggaccccga agtcaagttc    1620
aactggtacg tggatggcgt cgaagtgcat aatgctaaga ccaaaccaag ggaggaacag    1680
tacaactcca catatcgcgt cgtgtctgtc ctgactgtgc tgcaccagga ttggctgaac    1740
ggcaaagagt ataagtgcaa agtgagcaat aaggccctgc ccgctcctat cgagaaaact    1800
attagcaagg ctaaagggca gcctcgcgaa ccacaggtgt acaccctgcc tccatctcgg    1860
gacgaactga ctaagaacca agtcagtctg acctgtctgg tgaaagggtt ctatcctagc    1920
gacattgcag tggagtggga atccaatgga cagccagaga acaattacaa gaccacaccc    1980
cctgtgctgg actcagatgg aagcttcttt ctgtatagta agctgaccgt ggataaatca    2040
cgctggcagc agggcaacgt cttttcttgt agtgtgctgc atgaagccct gcacaatcat    2100
tacacacaga agtcactgag cctgtccect ggcaaatgaa ggatcc                   2146
```

<210> SEQ ID NO 15
<211> LENGTH: 708
<212> TYPE: PRT
<213> ORGANISM: Artificial Sequence
<220> FEATURE:
<223> OTHER INFORMATION: Biparatopic antibody construct HC12

<400> SEQUENCE: 15

```
Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ala Asp Tyr Thr Met Asp Trp Val Arg Gln Ala Pro Gly Lys Gly Leu
    50                  55                  60

Glu Trp Val Ala Asp Val Asn Pro Asn Ser Gly Ala Ser Ile Tyr Asn
65                  70                  75                  80

Gln Arg Phe Lys Gly Arg Phe Thr Leu Ser Val Asp Arg Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asn Leu Gly Pro Ser Phe Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175
```

```
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
                195                 200                 205
Val Pro Ser Ser Ser Leu Gly Thr Gln Thr Tyr Ile Cys Asn Val Asn
            210                 215                 220
His Lys Pro Ser Asn Thr Lys Val Asp Lys Lys Val Glu Pro Lys Ser
225                 230                 235                 240
Cys Asp Lys Gly Gly Gly Ser Gly Gly Gly Ser Gly Gly Gly Ser Gly
                245                 250                 255
Gly Gly Glu Val Gln Leu Val Glu Ser Gly Gly Gly Leu Val Gln Pro
            260                 265                 270
Gly Gly Ser Leu Arg Leu Ser Cys Ala Ala Ser Gly Phe Asn Ile Lys
            275                 280                 285
Asp Thr Tyr Ile His Trp Val Arg Gln Ala Pro Gly Lys Gly Leu Glu
            290                 295                 300
Trp Val Ala Arg Ile Tyr Pro Thr Thr Gly Tyr Thr Arg Tyr Ala Asp
305                 310                 315                 320
Ser Val Lys Gly Arg Phe Thr Ile Ser Ala Asp Thr Ser Lys Asn Thr
                325                 330                 335
Ala Tyr Leu Gln Met Asn Ser Leu Arg Ala Glu Asp Thr Ala Val Tyr
            340                 345                 350
Tyr Cys Ser Arg Trp Gly Gly Gly Phe Tyr Ala Met Asp Tyr Trp
            355                 360                 365
Gly Gln Gly Thr Leu Val Thr Val Ser Ser Ala Ser Thr Lys Gly Pro
            370                 375                 380
Ser Val Phe Pro Leu Ala Pro Ser Ser Lys Ser Thr Ser Gly Gly Thr
385                 390                 395                 400
Ala Ala Leu Gly Cys Leu Val Lys Asp Tyr Phe Pro Glu Pro Val Thr
                405                 410                 415
Val Ser Trp Asn Ser Gly Ala Leu Thr Ser Gly Val His Thr Phe Pro
            420                 425                 430
Ala Val Leu Gln Ser Ser Gly Leu Tyr Ser Leu Ser Ser Val Val Thr
            435                 440                 445
Val Pro Ser Ser Ser Leu Gly Thr Gln Thr Tyr Ile Cys Asn Val Asn
            450                 455                 460
His Lys Pro Ser Asn Thr Lys Val Asp Lys Lys Val Glu Pro Lys Ser
465                 470                 475                 480
Cys Asp Lys Thr His Thr Cys Pro Pro Cys Pro Ala Pro Glu Leu Leu
                485                 490                 495
Gly Gly Pro Ser Val Phe Leu Phe Pro Pro Lys Pro Lys Asp Thr Leu
            500                 505                 510
Met Ile Ser Arg Thr Pro Glu Val Thr Cys Val Val Val Asp Val Ser
            515                 520                 525
His Glu Asp Pro Glu Val Lys Phe Asn Trp Tyr Val Asp Gly Val Glu
            530                 535                 540
Val His Asn Ala Lys Thr Lys Pro Arg Glu Glu Gln Tyr Asn Ser Thr
545                 550                 555                 560
Tyr Arg Val Val Ser Val Leu Thr Val Leu His Gln Asp Trp Leu Asn
                565                 570                 575
Gly Lys Glu Tyr Lys Cys Lys Val Ser Asn Lys Ala Leu Pro Ala Pro
            580                 585                 590
Ile Glu Lys Thr Ile Ser Lys Ala Lys Gly Gln Pro Arg Glu Pro Gln
```

```
            595                 600                 605
Val Tyr Thr Leu Pro Pro Ser Arg Asp Glu Leu Thr Lys Asn Gln Val
    610                 615                 620

Ser Leu Thr Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
        675                 680                 685

Leu His Glu Ala Leu His Asn His Tyr Thr Gln Lys Ser Leu Ser Leu
690                 695                 700

Ser Pro Gly Lys
705

<210> SEQ ID NO 16
<211> LENGTH: 2146
<212> TYPE: DNA
<213> ORGANISM: Artificial Sequence
<220> FEATURE:
<223> OTHER INFORMATION: Biparatopic antibody construct HC12

<400> SEQUENCE: 16
gaattcgcca ccatgaactt tggcctgagc ctgattttc tcgtcctgat cctgaagggc       60
gtgcagtgtg aggtgcagct ggtggagagc ggcggcggcc tggtgcagcc cggcggcagc      120
ctgcgcctgt cctgcgccgc cagcggcttc acctttgccg actacaccat ggactgggtg      180
cgccaggctc ccggcaaggg cctggagtgg gtggccgacg tgaacccaa cagcggcgcc       240 agcatctaca ccagcgcttt caagggccgc ttcaccctga gcgtggaccg cagcaagaac      300
accctgtacc tgcagatgaa cagcctgcgc gccgaggaca ccgccgtgta ctactgcgcc      360
cgcaacctgg gccccagctt ctacttcgac tattgggggc agggcaccct ggtcaccgtg      420
agcagcgcta gcaccaaggg cccatccgtc ttccccctgg cacccctcct caagagcacc      480 tctggggca cagctgccct gggctgcctg gtcaaggact acttccccga accagtgacc       540
gtgtcctgga actcaggcgc cctgaccagc ggcgtgcaca ccttccctgc tgtcctgcag      600
tcctcaggac tctactccct cagcagcgtg gtgactgtgc cctctagcag cttgggcacc      660
cagacctaca tctgcaacgt gaatcacaag cccagcaaca ccaaggtgga caagaaagtt      720
gagcccaaat cttgtgacaa aggcggaggg agcggcggag gctccggagg cggcagcgga      780
ggcggagagg tgcagctggt ggagtctgga ggagggctgg tgcagccagg agggtccctg      840
agactgtctt gcgccgctag tggcttcaac atcaaggaca cctacatcca ctgggtgaga      900 caggccccg gaaaaggcct ggagtgggtg gccaggatct accctaccac cggctacacc      960
aggtacgccg acagcgtgaa gggcaggttc accatcagcg ccgacaccag caagaacacc     1020
gcctacctgc agatgaacag cctgagggcc gaggacaccg ccgtgtacta ctgcagcaga     1080 tgggcggca gcggcttcta cgccatggac tactggggac agggcacact ggtcactgtg     1140
tctagtgcct caacaaaggg gccatccgtc ttcccactgg ctccctcaag caaaagcact     1200
tccggaggca ccgctgcact gggatgtctg gtcaaggact acttcccaga gcccgtcacc     1260
gtgtcttgga cagtgggggc tctgaccagc ggagtccaca catttcctgc agtgctgcag     1320
tcctctggcc tgtacagcct gagttcagtg gtcacagtcc caagctcctc tctggggacc     1380
```

```
cagacatata tctgcaacgt gaatcacaag ccaagcaata ctaaagtcga caagaaagtg    1440
gagcccaaga gctgtgataa aactcatacc tgccccccct tgtcctgcacc agaactgctg    1500 ggaggaccat ccgtgttcct gtttccaccc aagcctaaag acaccctgat gatttcccgc    1560
acacccgagg tcacttgcgt ggtcgtggac gtgtctcacg aggaccccga agtcaagttc    1620
aactggtacg tggatggcgt cgaagtgcat aatgctaaga ccaaaccaag ggaggaacag    1680
tacaactcca catatcgcgt cgtgtctgtc ctgactgtgc tgcaccagga ttggctgaac    1740
ggcaaagagt ataagtgcaa agtgagcaat aaggccctgc ccgctcctat cgagaaaact    1800
attagcaagg ctaaagggca gcctcgcgaa ccacaggtgt acaccctgcc tccatctcgg    1860
gacgaactga ctaagaacca agtcagtctg acctgtctgg tgaaagggtt ctatcctagc    1920
gacattgcag tggagtggga atccaatgga cagccagaga acaattacaa gaccacaccc    1980
cctgtgctgg actcagatgg aagcttcttt ctgtatagta agctgaccgt ggataaatca    2040
cgctggcagc agggcaacgt cttttcttgt agtgtgctgc atgaagccct gcacaatcat    2100
tacacacaga agtcactgag cctgtcccct ggcaaatgaa ggatcc                    2146
```

<210> SEQ ID NO 17
<211> LENGTH: 705
<212> TYPE: PRT
<213> ORGANISM: Artificial Sequence
<220> FEATURE:
<223> OTHER INFORMATION: Biparatopic antibody construct HC13

<400> SEQUENCE: 17

```
Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ala Asp Tyr Thr Met Asp Trp Val Arg Gln Ala Pro Gly Lys Gly Leu
    50                  55                  60

Glu Trp Val Ala Asp Val Asn Pro Asn Ser Gly Gly Ser Ile Tyr Asn
65                  70                  75                  80

Gln Arg Phe Lys Gly Arg Phe Thr Leu Ser Val Asp Arg Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asn Leu Gly Pro Ser Phe Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
```

-continued

```
                225                 230                 235                 240
        Cys Asp Lys Thr His Thr Cys Pro Pro Cys Pro Ala Pro Glu Leu Leu
                        245                 250                 255
        Gly Gly Pro Ser Val Phe Leu Phe Pro Pro Lys Pro Lys Asp Thr Leu
                        260                 265                 270
        Met Ile Ser Arg Thr Pro Glu Val Thr Cys Val Val Val Asp Val Ser
                        275                 280                 285
        His Glu Asp Pro Glu Val Lys Phe Asn Trp Tyr Val Asp Gly Val Glu
                        290                 295                 300
        Val His Asn Ala Lys Thr Lys Pro Arg Glu Glu Gln Tyr Asn Ser Thr
        305                 310                 315                 320
        Tyr Arg Val Val Ser Val Leu Thr Val Leu His Gln Asp Trp Leu Asn
                        325                 330                 335
        Gly Lys Glu Tyr Lys Cys Lys Val Ser Asn Lys Ala Leu Pro Ala Pro
                        340                 345                 350
        Ile Glu Lys Thr Ile Ser Lys Ala Lys Gly Gln Pro Arg Glu Pro Gln
                        355                 360                 365
        Val Tyr Thr Leu Pro Pro Ser Arg Asp Glu Leu Thr Lys Asn Gln Val
                        370                 375                 380
        Ser Leu Thr Cys Leu Val Lys Gly Phe Tyr Pro Ser Asp Ile Ala Val
        385                 390                 395                 400
        Glu Trp Glu Ser Asn Gly Gln Pro Glu Asn Asn Tyr Lys Thr Thr Pro
                        405                 410                 415
        Pro Val Leu Asp Ser Asp Gly Ser Phe Phe Leu Tyr Ser Lys Leu Thr
                        420                 425                 430
        Val Asp Lys Ser Arg Trp Gln Gln Gly Asn Val Phe Ser Cys Ser Val
                        435                 440                 445
        Leu His Glu Ala Leu His Asn His Tyr Thr Gln Lys Ser Leu Ser Leu
                        450                 455                 460
        Ser Pro Gly Gly Gly Ser Gly Gly Gly Ser Gly Gly Gly Ser Gly Gly
        465                 470                 475                 480
        Gly Gly Glu Val Gln Leu Val Glu Ser Gly Gly Leu Val Gln Pro
                        485                 490                 495
        Gly Gly Ser Leu Arg Leu Ser Cys Ala Ala Ser Gly Phe Asn Ile Lys
                        500                 505                 510
        Asp Thr Tyr Ile His Trp Val Arg Gln Ala Pro Gly Lys Gly Leu Glu
                        515                 520                 525
        Trp Val Ala Arg Ile Tyr Pro Thr Thr Gly Tyr Thr Arg Tyr Ala Asp
                        530                 535                 540
        Ser Val Lys Gly Arg Phe Thr Ile Ser Ala Asp Thr Ser Lys Asn Thr
        545                 550                 555                 560
        Ala Tyr Leu Gln Met Asn Ser Leu Arg Ala Glu Asp Thr Ala Val Tyr
                        565                 570                 575
        Tyr Cys Ser Arg Trp Gly Gly Ser Gly Phe Tyr Ala Met Asp Tyr Trp
                        580                 585                 590
        Gly Gln Gly Thr Leu Val Thr Val Ser Ser Ala Ser Thr Lys Gly Pro
                        595                 600                 605
        Ser Val Phe Pro Leu Ala Pro Ser Ser Lys Ser Thr Ser Gly Gly Thr
                        610                 615                 620
        Ala Ala Leu Gly Cys Leu Val Lys Asp Tyr Phe Pro Glu Pro Val Thr
        625                 630                 635                 640
        Val Ser Trp Asn Ser Gly Ala Leu Thr Ser Gly Val His Thr Phe Pro
                        645                 650                 655
```

```
Ala Val Leu Gln Ser Ser Gly Leu Tyr Ser Leu Ser Ser Val Val Thr
            660                 665                 670

Val Pro Ser Ser Ser Leu Gly Thr Gln Thr Tyr Ile Cys Asn Val Asn
        675                 680                 685

His Lys Pro Ser Asn Thr Lys Val Asp Lys Lys Val Glu Pro Lys Ser
    690                 695                 700

Cys
705

<210> SEQ ID NO 18
<211> LENGTH: 2137
<212> TYPE: DNA
<213> ORGANISM: Artificial Sequence
<220> FEATURE:
<223> OTHER INFORMATION: Biparatopic antibody construct HC13

<400> SEQUENCE: 18
gaattcgcca ccatgaactt tggcctgagc ctgattttc tcgtcctgat cctgaagggc      60
gtgcagtgtg aggtgcagct ggtggagagc ggcggcggcc tggtgcagcc ggcggcagc    120 ctgcgcctgt cctgcgccgc cagcggcttc acctttgccg actacaccat ggactgggtg    180
cgccaggctc ccggcaaggg cctggagtgg gtggccgacg tgaaccccaa cagcggcggc    240
agcatctaca ccagcgcttt caagggccgc ttcaccctga cgtggaccg cagcaagaac    300 accctgtacc tgcagatgaa cagcctgcgc gccgaggaca ccgccgtgta ctactgcgcc    360
cgcaacctgg cccccagctt ctacttcgac tattggggc agggcaccct ggtcaccgtg    420
agcagcgcta gcaccaaggg cccatccgtc ttccccctgg caccctcctc caagagcacc    480 tctggggggca gctgccct gggctgcctg gtcaaggact acttccccga accagtgacc    540
gtgtcctgga actcaggcgc cctgaccagc ggcgtgcaca ccttccctgc tgtcctgcag    600
tcctcaggac tctactccct cagcagcgtg gtgactgtgc cctctagcag cttgggcacc    660
cagacctaca tctgcaacgt gaatcacaag cccagcaaca ccaaggtgga caagaaagtt    720
gagcccaaat cttgtgataa aactcatacc tgccccccctt gtcctgcacc agaactgctg    780
ggaggaccat ccgtgttcct gtttccacc aagcctaaag acaccctgat gatttcccgc    840
acacccgagg tcacttgcgt ggtcgtggac gtgtctcacg aggaccccga agtcaagttc    900
aactggtacg tggatggcgt cgaagtgcat aatgctaaga ccaaaccaag ggaggaacag    960
tacaactcca catatcgcgt cgtgtctgtc ctgactgtgc tgcaccagga ttggctgaac   1020
ggcaaagagt ataagtgcaa agtgagcaat aaggccctgc cgctcctat cgagaaaact   1080 attagcaagg ctaaagggca gcctcgcgaa ccacaggtgt acaccctgcc tccatctcgg   1140
gacgaactga ctaagaacca agtcagtctg acctgtctgg tgaaagggtt ctatcctagc   1200
gacattgcag tggagtggga atccaatgga cagccagaga caattacaa gaccacaccc   1260 cctgtgctgg actcagatgg aagcttcttt ctgtatagta agctgaccgt ggataaatca   1320
cgctggcagc agggcaacgt cttttcttgt agtgtgctgc atgaagccct gcacaatcat   1380
tacacacaga agtcactgag cctgtcccct ggcggcggag ggagcggcgg aggctccgga   1440
ggcggcagcg gaggcggaga ggtgcagctg gtggagtctg gaggagggct ggtgcagcca   1500
ggagggtccc tgagactgtc ttgcgccgct agtggcttca acatcaagga cacctacatc   1560
cactgggtga caggccccc ggaaaaaggc ctggagtggg tggccaggat ctaccctacc   1620
accggctaca ccaggtacgc cgacagcgtg aagggcaggt tcaccatcag cgccgacacc   1680
```

-continued

```
agcaagaaca ccgcctacct gcagatgaac agcctgaggg ccgaggacac cgccgtgtac    1740
tactgcagca gatggggcgg cagcggcttc tacgccatgg actactgggg acagggcaca    1800
ctggtcactg tgtctagtgc ctcaacaaag gggcctagcg tgtttccact ggctccctca    1860
agcaaaagca cttccggagg caccgctgca ctgggatgtc tggtgaagga ctacttccca    1920
gagcccgtca ccgtgtcttg aacagtgggg ctctgaccag cggagtccac acatttcct    1980 gcagtgctgc agtcctctgg cctgtacagc ctgagttcag tggtcacagt cccaagctcc    2040
tctctgggga cccagacata tatctgcaac gtgaatcaca agccaagcaa tactaaagtc    2100
gacaagaaag tggagcccaa gagctgttga aggatcc                              2137
```

<210> SEQ ID NO 19
<211> LENGTH: 468
<212> TYPE: PRT
<213> ORGANISM: Artificial Sequence
<220> FEATURE:
<223> OTHER INFORMATION: Biparatopic antibody construct HC14

<400> SEQUENCE: 19

```
Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ala Asp Tyr Thr Met Asp Trp Val Arg Gln Ala Pro Gly Lys Gly Leu
    50                  55                  60

Glu Trp Val Ala Asp Val Asn Pro Asn Ser Gly Gly Ser Ile Tyr Asn
65                  70                  75                  80

Gln Arg Phe Lys Gly Arg Phe Thr Leu Ser Val Asp Arg Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asn Leu Gly Pro Ser Phe Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285
```

```
His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Trp Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Leu His Glu Ala Leu His Asn His Tyr Thr Gln Lys Ser Leu Ser Leu
    450                 455                 460

Ser Pro Gly Lys
465
```

```
<210> SEQ ID NO 20
<211> LENGTH: 1426
<212> TYPE: DNA
<213> ORGANISM: Artificial Sequence
<220> FEATURE:
<223> OTHER INFORMATION: Biparatopic antibody construct HC14

<400> SEQUENCE: 20
gaattcgcca ccatgaactt tggcctgagc ctgattttc tcgtcctgat cctgaagggc      60
gtgcagtgtg aggtgcagct ggtggagagc ggcggcggcc tggtgcagcc cggcggcagc    120
ctgcgcctgt cctgcgccgc cagcggcttc acctttgccg actacaccat ggactgggtg    180
cgccaggctc ccggcaaggg cctggagtgg gtggccgacg tgaaccccaa cagcggcggc    240
agcatctaca ccagcgcttt caagggccgc ttcaccctga gcgtggaccg cagcaagaac    300
accctgtacc tgcagatgaa cagcctgcgc gccgaggaca ccgccgtgta ctactgcgcc    360
cgcaacctgg cccccagctt ctacttcgac tattgggggc agggcaccct ggtcaccgtg    420
agcagcgcta gcaccaaggg cccatccgtc ttccccctgg cacctcctc caagagcacc    480
tctgggggca cagctgccct gggctgcctg gtcaaggact acttccccga accagtgacc    540
gtgtcctgga actcaggcgc cctgaccagc ggcgtgcaca ccttccctgc tgtcctgcag    600
tcctcaggac tctactccct cagcagcgtg gtgactgtgc cctctagcag cttgggcacc    660
cagacctaca tctgcaacgt gaatcacaag cccagcaaca ccaaggtgga caagaaagtt    720
gagcccaaat cttgtgataa aactcatacc tgcccccctt gtcctgcacc agaactgctg    780
ggaggaccat ccgtgttcct gtttccaccc aagcctaaag acaccctgat gatttcccgc    840
acacccgagg tcacttgcgt ggtcgtggac gtgtctcacg aggaccccga agtcaagttc    900
aactggtacg tggatggcgt cgaagtgcat aatgctaaga ccaaaccaag ggaggaacag    960
```

-continued

```
tacaactcca catatcgcgt cgtgtctgtc ctgactgtgc tgcaccagga ttggctgaac    1020
ggcaaagagt ataagtgcaa agtgagcaat aaggccctgc ccgctcctat cgagaaaact    1080
attagcaagg ctaaagggca gcctcgcgaa ccacaggtgt acaccctgcc tccatctcgg    1140
gacgaactga ctaagaacca agtcagtctg tggtgtctgg tgaaagggtt ctatcctagc    1200
gacattgcag tggagtggga atccaatgga cagccagaga caattacaa gaccacaccc     1260 cctgtgctgg actcagatgg aagcttcttt ctgtatagta agctgaccgt ggataaatca    1320
cgctggcagc agggcaacgt cttttcttgt agtgtgctgc atgaagccct gcacaatcat    1380
tacacacaga agtcactgag cctgtccccct ggcaaatgaa ggatcc                  1426
```

<210> SEQ ID NO 21
<211> LENGTH: 469
<212> TYPE: PRT
<213> ORGANISM: Artificial Sequence
<220> FEATURE:
<223> OTHER INFORMATION: Biparatopic antibody construct HC15

<400> SEQUENCE: 21

```
Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Thr Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Ser Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285
```

```
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
            325                 330                 335
Asn Gly Lys Glu Tyr Lys Cys Lys Val Ser Asn Lys Ala Leu Pro Ala
        340                 345                 350
Pro Ile Glu Lys Thr Ile Ser Lys Ala Lys Gly Gln Pro Arg Glu Pro
    355                 360                 365
Gln Val Tyr Thr Leu Pro Pro Ser Arg Asp Glu Leu Thr Lys Asn Gln
370                 375                 380
Val Ser Leu Ser Cys Ala Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
            405                 410                 415
Pro Pro Val Leu Asp Ser Asp Gly Ser Phe Phe Leu Val Ser Lys Leu
        420                 425                 430
Thr Val Asp Lys Ser Arg Trp Gln Gln Gly Asn Val Phe Ser Cys Ser
    435                 440                 445
Val Leu His Glu Ala Leu His Asn His Tyr Thr Gln Lys Ser Leu Ser
450                 455                 460
Leu Ser Pro Gly Lys
465

<210> SEQ ID NO 22
<211> LENGTH: 1429
<212> TYPE: DNA
<213> ORGANISM: Artificial Sequence
<220> FEATURE:
<223> OTHER INFORMATION: Biparatopic antibody construct HC15

<400> SEQUENCE: 22
gaattcgcca ccatgaactt tggcctgagc ctgattttc tcgtcctgat cctgaagggc      60
gtgcagtgtg aggtgcagct ggtggagtct ggaggagggc tggtgcagcc aggagggtcc    120
ctgagactgt cttgcgccgc tagtggcttc aacatcaagg acacctacat ccactgggtg    180
agacaggccc ccggaaaagg cctggagtgg gtggccagga tctaccctac caccggctac    240
accaggtacg ccgacagcgt gaagggcagg ttcaccatca gcgccgacac cagcaagaac    300
accgcctacc tgcagatgaa cagcctgagg gccgaggaca ccgccgtgta ctactgcagc    360
agatggggcg gcagcggctt ctacgccatg gactactggg gacagggcac actggtcact    420
gtgtctagtg cctcaacaaa ggggcctagc gtgtttccac tggctccctc aagcaaaagc    480
acttccggag caccgctgc actgggatgt ctggtgaagg actacttccc agagcccgtc    540
accgtgtctt ggaacagtgg ggctctgacc agcggagtcc acacatttcc tgcagtgctg    600
cagtcctctg gcctgtacag cctgagttca gtggtcacag tcccaagctc ctctctgggg    660
acccagacat atatctgcaa cgtgaatcac aagccaagca atactaaagt cgacaagaaa    720
gtggagccca gagctgtga taaaactcat acctgccccc cttgtcctgc accagaactg    780
ctgggaggac catccgtgtt cctgtttcca cccaagccta agacaccct gatgatttcc    840
cgcacacccg aggtcacttg cgtggtcgtg gacgtgtctc acgaggaccc cgaagtcaag    900
ttcaactggt acgtggatgg cgtcgaagtg cataatgcta agaccaaacc aagggaggaa    960
```

```
cagtacaact ccacatatcg cgtcgtgtct gtcctgactg tgctgcacca ggattggctg    1020
aacggcaaag agtataagtg caaagtgagc aataaggccc tgcccgctcc tatcgagaaa    1080
actattagca aggctaaagg gcagcctcgc gaaccacagg tgtacaccct gcctccatct    1140
cgggacgaac tgactaagaa ccaagtcagt ctgagctgtg ccgtgaaagg gttctatcct    1200
agcgacattg cagtggagtg ggaatccaat ggacagccag agaacaatta caagaccaca    1260 cccctgtgc tggactcaga tggaagcttc tttctggtga gtaagctgac cgtggataaa     1320
tcacgctggc agcagggcaa cgtcttttct tgtagtgtgc tgcatgaagc cctgcacaat    1380
cattacacac agaagtcact gagcctgtcc cctggcaaat gaaggatcc                1429
```

<210> SEQ ID NO 23
<211> LENGTH: 15
<212> TYPE: PRT
<213> ORGANISM: Artificial Sequence
<220> FEATURE:
<223> OTHER INFORMATION: Linker sequence

<400> SEQUENCE: 23

```
Gly Gly Gly Ser Gly Gly Gly Ser Gly Gly Gly Ser Gly Gly Gly
1               5                   10                  15
```

<210> SEQ ID NO 24
<211> LENGTH: 19
<212> TYPE: PRT
<213> ORGANISM: Artificial Sequence
<220> FEATURE:
<223> OTHER INFORMATION: Signal sequence

<400> SEQUENCE: 24

```
Met Asn Phe Gly Leu Ser Leu Ile Phe Leu Val Leu Ile Leu Lys Gly
1               5                   10                  15

Val Gln Cys
```

<210> SEQ ID NO 25
<211> LENGTH: 45
<212> TYPE: PRT
<213> ORGANISM: Artificial Sequence
<220> FEATURE:
<223> OTHER INFORMATION: Signal sequence

<400> SEQUENCE: 25

```
Gly Gly Cys Gly Gly Ala Gly Gly Gly Ala Gly Cys Gly Gly Cys Gly
1               5                   10                  15

Gly Ala Gly Gly Cys Thr Cys Cys Gly Gly Ala Gly Gly Cys Gly Gly
                20                  25                  30

Cys Ala Gly Cys Gly Gly Ala Gly Gly Cys Gly Gly Ala
            35                  40                  45
```

<210> SEQ ID NO 26
<211> LENGTH: 12
<212> TYPE: PRT
<213> ORGANISM: Artificial Sequence
<220> FEATURE:
<223> OTHER INFORMATION: EcoRI/Kozak sequence

<400> SEQUENCE: 26

```
Gly Ala Ala Thr Thr Cys Gly Cys Cys Ala Cys Cys
1               5                   10
```

<210> SEQ ID NO 27
<211> LENGTH: 7

```
-continued

<212> TYPE: DNA
<213> ORGANISM: Artificial Sequence
<220> FEATURE:
<223> OTHER INFORMATION: BamHI cloning site

<400> SEQUENCE: 27 aggatcc                                                              7

<210> SEQ ID NO 28
<211> LENGTH: 57
<212> TYPE: DNA
<213> ORGANISM: Artificial Sequence
<220> FEATURE:
<223> OTHER INFORMATION: Signal sequence

<400> SEQUENCE: 28
atgaactttg gcctgagcct gattttctc gtcctgatcc tgaagggcgt gcagtgt     57

<210> SEQ ID NO 29
<211> LENGTH: 243
<212> TYPE: PRT
<213> ORGANISM: Artificial Sequence
<220> FEATURE:
<223> OTHER INFORMATION: Pert_VH_V16xCH1FcML

<400> SEQUENCE: 29
```

Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Thr Met Asp Trp Val Arg Gln Ala Pro Gly Lys Gly Leu
    50                  55                  60

Glu Trp Val Ala Asp Val Asn Pro Asn Ser Gly Gly Ser Ile Tyr Asn
65                  70                  75                  80

Gln Arg Phe Lys Gly Arg Phe Thr Leu Ser Val Asp Arg Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asn Leu Gly Pro Ser Phe Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys

<210> SEQ ID NO 30
<211> LENGTH: 450
<212> TYPE: PRT
<213> ORGANISM: Artificial Sequence
<220> FEATURE:
<223> OTHER INFORMATION: Tra_VH-VNT_DSCH1

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Thr Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Ser Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp

```
                370              375              380
Glu Ser Asn Gly Gln Pro Glu Asn Asn Tyr Lys Thr Thr Pro Pro Val
385              390              395              400

Leu Asp Ser Asp Gly Ser Phe Phe Leu Tyr Ser Lys Leu Thr Val Asp
            405              410              415

Lys Ser Arg Trp Gln Gln Gly Asn Val Phe Ser Cys Ser Val Leu His
            420              425              430

Glu Ala Leu His Asn His Tyr Thr Gln Lys Ser Leu Ser Leu Ser Pro
            435              440              445

Gly Lys
    450

<210> SEQ ID NO 31
<211> LENGTH: 708
<212> TYPE: PRT
<213> ORGANISM: Artificial Sequence
<220> FEATURE:
<223> OTHER INFORMATION: Pert_VH_V16xCH1FcML-linker-Tra_VH-VNT_DSCH1

<400> SEQUENCE: 31

Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Thr Met Asp Trp Val Arg Gln Ala Pro Gly Lys Gly Leu
    50                  55                  60

Glu Trp Val Ala Asp Val Asn Pro Asn Ser Gly Gly Ser Ile Tyr Asn
65                  70                  75                  80

Gln Arg Phe Lys Gly Arg Phe Thr Leu Ser Val Asp Arg Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asn Leu Gly Pro Ser Phe Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Gly Gly Gly Ser Gly Gly Gly Ser Gly Gly Gly Ser Gly
                245                 250                 255

Gly Gly Glu Val Gln Leu Val Glu Ser Gly Gly Gly Leu Val Gln Pro
            260                 265                 270

Gly Gly Ser Leu Arg Leu Ser Cys Ala Ala Ser Gly Phe Asn Ile Lys
```

```
                 275                 280                 285
Asp Thr Tyr Ile His Trp Val Arg Gln Ala Pro Gly Lys Gly Leu Glu
290                 295                 300
Trp Val Ala Arg Ile Tyr Pro Thr Thr Gly Tyr Thr Arg Tyr Ala Asp
305                 310                 315                 320
Ser Val Lys Gly Arg Phe Thr Ile Ser Ala Asp Thr Ser Lys Asn Thr
                325                 330                 335
Ala Tyr Leu Gln Met Asn Ser Leu Arg Ala Glu Asp Thr Ala Val Tyr
                340                 345                 350
Tyr Cys Ser Arg Trp Gly Gly Ser Gly Phe Tyr Ala Met Asp Tyr Trp
                355                 360                 365
Gly Gln Gly Thr Leu Val Thr Val Ser Ser Ala Ser Thr Lys Gly Pro
                370                 375                 380
Ser Val Phe Pro Leu Ala Pro Ser Ser Lys Ser Thr Ser Gly Gly Thr
385                 390                 395                 400
Ala Ala Leu Gly Cys Leu Val Lys Asp Tyr Phe Pro Glu Pro Val Thr
                405                 410                 415
Val Ser Trp Asn Ser Gly Ala Leu Thr Ser Gly Val His Thr Phe Pro
                420                 425                 430
Ala Val Leu Gln Ser Ser Gly Leu Tyr Ser Leu Ser Ser Val Val Thr
                435                 440                 445
Val Pro Ser Ser Ser Leu Gly Thr Gln Thr Tyr Ile Cys Asn Val Asn
                450                 455                 460
His Lys Pro Ser Asn Thr Lys Val Asp Lys Lys Val Glu Pro Lys Ser
465                 470                 475                 480
Cys Asp Lys Thr His Thr Cys Pro Pro Cys Pro Ala Pro Glu Leu Leu
                485                 490                 495
Gly Gly Pro Ser Val Phe Leu Phe Pro Pro Lys Pro Lys Asp Thr Leu
                500                 505                 510
Met Ile Ser Arg Thr Pro Glu Val Thr Cys Val Val Val Asp Val Ser
                515                 520                 525
His Glu Asp Pro Glu Val Lys Phe Asn Trp Tyr Val Asp Gly Val Glu
                530                 535                 540
Val His Asn Ala Lys Thr Lys Pro Arg Glu Glu Gln Tyr Asn Ser Thr
545                 550                 555                 560
Tyr Arg Val Val Ser Val Leu Thr Val Leu His Gln Asp Trp Leu Asn
                565                 570                 575
Gly Lys Glu Tyr Lys Cys Lys Val Ser Asn Lys Ala Leu Pro Ala Pro
                580                 585                 590
Ile Glu Lys Thr Ile Ser Lys Ala Lys Gly Gln Pro Arg Glu Pro Gln
                595                 600                 605
Val Tyr Thr Leu Pro Pro Ser Arg Glu Glu Met Thr Lys Asn Gln Val
                610                 615                 620
Ser Leu Thr Cys Leu Val Lys Gly Phe Tyr Pro Ser Asp Ile Ala Val
625                 630                 635                 640
Glu Trp Glu Ser Asn Gly Gln Pro Glu Asn Asn Tyr Lys Thr Thr Pro
                645                 650                 655
Pro Val Leu Asp Ser Asp Gly Ser Phe Phe Leu Tyr Ser Lys Leu Thr
                660                 665                 670
Val Asp Lys Ser Arg Trp Gln Gln Gly Asn Val Phe Ser Cys Ser Val
                675                 680                 685
Leu His Glu Ala Leu His Asn His Tyr Thr Gln Lys Ser Leu Ser Leu
                690                 695                 700
```

-continued

```
Ser Pro Gly Lys
705

<210> SEQ ID NO 32
<211> LENGTH: 467
<212> TYPE: PRT
<213> ORGANISM: Artificial Sequence
<220> FEATURE:
<223> OTHER INFORMATION: Pert_Fab+Fc

<400> SEQUENCE: 32

Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Thr Met Asp Trp Val Arg Gln Ala Pro Gly Lys Gly Leu
    50                  55                  60

Glu Trp Val Ala Asp Val Asn Pro Asn Ser Gly Gly Ser Ile Tyr Asn
65                  70                  75                  80

Gln Arg Phe Lys Gly Arg Phe Thr Leu Ser Val Asp Arg Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asn Leu Gly Pro Ser Phe Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350
```

```
Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Leu His Glu Ala Leu His Asn His Tyr Thr Gln Lys Ser Leu Ser Leu
        450                 455                 460

Ser Pro Gly
465

<210> SEQ ID NO 33
<211> LENGTH: 223
<212> TYPE: PRT
<213> ORGANISM: Artificial Sequence
<220> FEATURE:
<223> OTHER INFORMATION: Tras_Fab

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Thr Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Ser Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 34
```

<211> LENGTH: 705
<212> TYPE: PRT
<213> ORGANISM: Artificial Sequence
<220> FEATURE:
<223> OTHER INFORMATION: Pert_HC_v2x-Tra_HC_vNT_DS_ML

<400> SEQUENCE: 34

```
Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Thr Met Asp Trp Val Arg Gln Ala Pro Gly Lys Gly Leu
    50                  55                  60

Glu Trp Val Ala Asp Val Asn Pro Asn Ser Gly Gly Ser Ile Tyr Asn
65                  70                  75                  80

Gln Arg Phe Lys Gly Arg Phe Thr Leu Ser Val Asp Arg Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asn Leu Gly Pro Ser Phe Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380
```

```
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
    435                 440                 445

Leu His Glu Ala Leu His Asn His Tyr Thr Gln Lys Ser Leu Ser Leu
450                 455                 460

Ser Pro Gly Gly Gly Ser Gly Gly Gly Ser Gly Gly Gly Ser Gly
465                 470                 475                 480

Gly Gly Glu Val Gln Leu Val Glu Ser Gly Gly Leu Val Gln Pro
                485                 490                 495

Gly Gly Ser Leu Arg Leu Ser Cys Ala Ala Ser Gly Phe Asn Ile Lys
            500                 505                 510

Asp Thr Tyr Ile His Trp Val Arg Gln Ala Pro Gly Lys Gly Leu Glu
        515                 520                 525

Trp Val Ala Arg Ile Tyr Pro Thr Thr Gly Tyr Thr Arg Tyr Ala Asp
530                 535                 540

Ser Val Lys Gly Arg Phe Thr Ile Ser Ala Asp Thr Ser Lys Asn Thr
545                 550                 555                 560

Ala Tyr Leu Gln Met Asn Ser Leu Arg Ala Glu Asp Thr Ala Val Tyr
                565                 570                 575

Tyr Cys Ser Arg Trp Gly Gly Ser Gly Phe Tyr Ala Met Asp Tyr Trp
            580                 585                 590

Gly Gln Gly Thr Leu Val Thr Val Ser Ser Ala Ser Thr Lys Gly Pro
        595                 600                 605

Ser Val Phe Pro Leu Ala Pro Ser Ser Lys Ser Thr Ser Gly Gly Thr
    610                 615                 620

Ala Ala Leu Gly Cys Leu Val Lys Asp Tyr Phe Pro Glu Pro Val Thr
625                 630                 635                 640

Val Ser Trp Asn Ser Gly Ala Leu Thr Ser Gly Val His Thr Phe Pro
                645                 650                 655

Ala Val Leu Gln Ser Ser Gly Leu Tyr Ser Leu Ser Ser Val Val Thr
            660                 665                 670

Val Pro Ser Ser Ser Leu Gly Thr Gln Thr Tyr Ile Cys Asn Val Asn
        675                 680                 685

His Lys Pro Ser Asn Thr Lys Val Asp Lys Lys Val Glu Pro Lys Ser
    690                 695                 700

Cys
705

<210> SEQ ID NO 35
<211> LENGTH: 468
<212> TYPE: PRT
<213> ORGANISM: Artificial Sequence
<220> FEATURE:
<223> OTHER INFORMATION: Pert_HC_v16x Knob

<400> SEQUENCE: 35

Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30
```

-continued

```
Pro Gly Gly Ser Leu Arg Leu Ser Cys Ala Ala Ser Gly Phe Thr Phe
         35                  40                  45

Thr Asp Tyr Thr Met Asp Trp Val Arg Gln Ala Pro Gly Lys Gly Leu
 50                  55                  60

Glu Trp Val Ala Asp Val Asn Pro Asn Ser Gly Gly Ser Ile Tyr Asn
 65                  70                  75                  80

Gln Arg Phe Lys Gly Arg Phe Thr Leu Ser Val Asp Arg Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Arg Asn Leu Gly Pro Ser Phe Tyr Phe Asp Tyr Trp
                115                 120                 125

Gly Gln Gly Thr Leu Val Thr Val Ser Ser Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Glu Glu Met Thr Lys Asn Gln Val
    370                 375                 380

Ser Leu Trp Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445
```

Leu His Glu Ala Leu His Asn His Tyr Thr Gln Lys Ser Leu Ser Leu
            450                 455                 460

Ser Pro Gly Lys
465

<210> SEQ ID NO 36
<211> LENGTH: 450
<212> TYPE: PRT
<213> ORGANISM: Artificial Sequence
<220> FEATURE:
<223> OTHER INFORMATION: Tras_HC_hole

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Thr Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Ser Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Leu His
            420                 425                 430

Glu Ala Leu His Asn His Tyr Thr Gln Lys Ser Leu Ser Leu Ser Pro
            435                 440                 445

Gly Lys
    450

<210> SEQ ID NO 37
<211> LENGTH: 450
<212> TYPE: PRT
<213> ORGANISM: Artificial Sequence
<220> FEATURE:
<223> OTHER INFORMATION: gTra_HC_vNT_DT_ML

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Thr Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Leu His
            420                 425                 430

Glu Ala Leu His Asn His Tyr Thr Gln Lys Ser Leu Ser Leu Ser Pro
        435                 440                 445

Gly Lys
    450

<210> SEQ ID NO 38
<211> LENGTH: 741
<212> TYPE: DNA
<213> ORGANISM: Artificial Sequence
<220> FEATURE:
<223> OTHER INFORMATION: EcoRI-Kozak-Pert_VH_V16xCH1FcML

<400> SEQUENCE: 38
gaattcgcca ccatgaactt tggcctgagc ctgattttc tcgtcctgat cctgaagggc    60
gtgcagtgtg aggtgcagct ggtggagagc ggcggcggcc tggtgcagcc cggcggcagc   120
ctgcgcctgt cctgcgccgc cagcggcttc acctttaccg actacaccat ggactgggtg   180
cgccaggctc ccggcaaggg cctggagtgg gtggccgacg tgaaccccaa cagcggcggc   240
agcatctaca accagcgctt caagggccgc ttcaccctga gcgtggaccg cagcaagaac   300
accctgtacc tgcagatgaa cagcctgcgc gccgaggaca ccgccgtgta ctactgcgcc   360
cgcaacctgg cccccagctt ctacttcgac tattggggc agggcaccct ggtcaccgtg   420
agcagcgcta gcaccaaggg cccatccgtc ttccccctgg caccctcctc caagagcacc   480
tctgggggca gctgccct gggctgcctg gtcaaggact acttccccga accagtgacc   540
gtgtcctgga actcaggcgc cctgaccagc ggcgtgcaca ccttccctgc tgtcctgcag   600
tcctcaggac tctactccct cagcagcgtg gtgactgtgc cctctagcag cttgggcacc   660
cagacctaca tctgcaacgt gaatcacaag cccagcaaca ccaaggtgga caagaaagtt   720
gagcccaaat cttgtgacaa a                                              741
```

<210> SEQ ID NO 39
<211> LENGTH: 1360
<212> TYPE: DNA
<213> ORGANISM: Artificial Sequence
<220> FEATURE:
<223> OTHER INFORMATION: Tra_VH-VNT_DSCH1

<400> SEQUENCE: 39

```
gaggtgcagc tggtggagtc tggaggaggg ctggtgcagc caggagggtc cctgagactg      60
tcttgcgccg ctagtggctt caacatcaag gacacctaca tccactgggt gagacaggcc     120
cccggaaaag gcctggagtg ggtggccagg atctacccta ccaccggcta caccaggtac     180
gccgacagcg tgaagggcag gttcaccatc agcgccgaca ccagcaagaa caccgcctac     240
ctgcagatga acagcctgag ggccgaggac accgccgtgt actactgcag cagatggggc     300
ggcagcggct tctacgccat ggactactgg ggacagggca cactggtcac tgtgtctagt     360
gcctcaacaa aggggcctag cgtgtttcca ctggctccct caagcaaaag cacttccgga     420
ggcaccgctg cactgggatg tctggtgaag gactacttcc cagagcccgt caccgtgtct     480
tggaacagtg gggctctgac cagcggagtc cacacatttc ctgcagtgct gcagtcctct     540
ggcctgtaca gcctgagttc agtggtcaca gtcccaagct cctctctggg gacccagaca     600
tatatctgca acgtgaatca caagccaagc aatactaaag tcgacaagaa agtggagccc     660
aagagctgtg ataaaactca tacctgcccc ccttgtcctg caccagaact gctgggagga     720
ccatccgtgt tcctgtttcc acccaagcct aaagacaccc tgatgatttc ccgcacaccc     780
gaggtcactt gcgtggtcgt ggacgtgtct cacgaggacc ccgaagtcaa gttcaactgg     840
tacgtggatg gcgtcgaagt gcataatgct aagaccaaac aagggagga acagtacaac     900
tccacatatc gcgtcgtgtc tgtcctgact gtgctgcacc aggattggct gaacggcaaa     960
gagtataagt gcaaagtgag caataaggcc ctgcccgctc tatcgagaa aactattagc     1020
aaggctaaag gcagcctcg cgaaccacag gtgtacaccc tgcctccatc tcgggaggaa     1080
atgactaaga accaagtcag tctgacctgt ctggtgaaag ggttctatcc tagcgacatt     1140
gcagtggagt gggaatccaa tggacagcca gagaacaatt acaagaccac accccctgtg     1200
ctggactcag atggaagctt ctttctgtat agtaagctga ccgtggataa atcacgctgg     1260
cagcagggca acgtctttc ttgtagtgtg ctgcatgaag ccctgcacaa tcattacaca     1320
cagaagtcac tgagcctgtc ccctggcaaa tgaaggatcc                          1360
```

<210> SEQ ID NO 40
<211> LENGTH: 2127
<212> TYPE: DNA
<213> ORGANISM: Artificial Sequence
<220> FEATURE:
<223> OTHER INFORMATION: Pert_HC_v2x_Tra_HC_vNT_DS_ML

<400> SEQUENCE: 40

```
gaattcgcca ccatgaactt tggcctgagc ctgattttc tcgtcctgat cctgaagggc      60
gtgcagtgtg aggtgcagct ggtggagagc ggcggcggcc tggtgcagcc ggcggcagc     120
ctgcgcctgt cctgcgccgc cagcggcttc acctttaccg actacaccat ggactgggtg     180
cgccaggctc ccggcaaggg cctggagtgg gtggccgacg tgaacccaa cagcggcggc     240
agcatctaca accagcgctt caagggccgc ttcaccctga gcgtggaccg cagcaagaac     300
accctgtacc tgcagatgaa cagcctgcgc gccgaggaca ccgccgtgta ctactgcgcc     360
cgcaacctgg gcccagctt ctacttcgac tattgggggc agggcaccct ggtcaccgtg     420
```

| | |
|---|---|
| agcagcgcta gcaccaaggg cccatccgtc ttccccctgg caccctcctc caagagcacc | 480 |
| tctgggggca cagctgccct gggctgcctg gtcaaggact acttccccga accagtgacc | 540 |
| gtgtcctgga actcaggcgc cctgaccagc ggcgtgcaca ccttccctgc tgtcctgcag | 600 |
| tcctcaggac tctactccct cagcagcgtg gtgactgtgc cctctagcag cttgggcacc | 660 |
| cagacctaca tctgcaacgt gaatcacaag cccagcaaca ccaaggtgga caagaaagtt | 720 |
| gagcccaaat cttgtgataa aactcatacc tgccccccctt gtcctgcacc agaactgctg | 780 |
| ggaggaccat ccgtgttcct gtttccaccc aagcctaaag acaccctgat gatttcccgc | 840 |
| acacccgagg tcacttgcgt ggtcgtggac gtgtctcacg aggaccccga agtcaagttc | 900 |
| aactggtacg tggatggcgt cgaagtgcat aatgctaaga ccaaaccaag ggaggaacag | 960 |
| tacaactcca catatcgcgt cgtgtctgtc ctgactgtgc tgcaccagga ttggctgaac | 1020 |
| ggcaaagagt ataagtgcaa agtgagcaat aaggccctgc ccgctcctat cgagaaaact | 1080 |
| attagcaagg ctaaagggca gcctcgcgaa ccacaggtgt acaccctgcc tccatctcgg | 1140 |
| gaggaaatga ctaagaacca agtcagtctg acctgtctgg tgaaagggtt ctatcctagc | 1200 |
| gacattgcag tggagtggga atccaatgga cagccagaga acaattacaa gaccacaccc | 1260 |
| cctgtgctgg actcagatgg aagcttcttt ctgtatagta agctgaccgt ggataaatca | 1320 |
| cgctggcagc agggcaacgt cttttcttgt agtgtgctgc atgaagccct gcacaatcat | 1380 |
| tacacacaga agtcactgag cctgtcccct ggcggcggag ggagcggcgg aggctccgga | 1440 |
| ggcggcagcg gaggcggaga ggtgcagctg gtggagtctg gaggaggcet ggtgcagcca | 1500 |
| ggagggtccc tgagactgtc ttgcgccgct agtggcttca acatcaagga cacctacatc | 1560 |
| cactgggtga acaggccccc cggaaaaggc ctggagtggg tggccaggat ctaccctacc | 1620 |
| accggctaca ccaggtacgc cgacagcgtg aagggcaggt tcaccatcag cgccgacacc | 1680 |
| agcaagaaca ccgcctacct gcagatgaac agcctgaggg ccgaggacac cgccgtgtac | 1740 |
| tactgcagca gatggggcgg cagcggcttc tacgccatgg actactgggg acagggcaca | 1800 |
| ctggtcactg tgtctagtgc ctcaacaaag gggcctagcg tgtttccact ggctccctca | 1860 |
| agcaaaagca cttccggagg caccgctgca ctggatgtc tggtgaagga ctacttccca | 1920 |
| gagcccgtca ccgtgtcttg aacagtgggg ctctgaccag gcggagtcca cacatttcct | 1980 |
| gcagtgctgc agtcctctgg cctgtacagc ctgagttcag tggtcacagt cccaagctcc | 2040 |
| tctctgggga cccagacata tatctgcaac gtgaatcaca agccaagcaa tactaaagtc | 2100 |
| gacaagaaag tggagcccaa gagctgt | 2127 |

<210> SEQ ID NO 41
<211> LENGTH: 1426
<212> TYPE: DNA
<213> ORGANISM: Artificial Sequence
<220> FEATURE:
<223> OTHER INFORMATION: Pert_HC_v16x Knob

<400> SEQUENCE: 41

| | |
|---|---|
| gaattcgcca ccatgaactt tggcctgagc ctgatttttc tcgtcctgat cctgaagggc | 60 |
| gtgcagtgtg aggtgcagct ggtggagagc ggcggcggcc tggtgcagcc cggcggcagc | 120 |
| ctgcgcctgt cctgcgccgc cagcggcttc acctttaccg actacaccat ggactgggtg | 180 |
| cgccaggctc ccggcaaggg cctggagtgg gtggccgacg tgaacccaa cagcggcggc | 240 |
| agcatctaca accagcgctt caagggccgc ttcaccctga gcgtggaccg cagcaagaac | 300 |
| accctgtacc tgcagatgaa cagcctgcgc gccgaggaca ccgccgtgta ctactgcgcc | 360 |

```
cgcaacctgg gccccagctt ctacttcgac tattggggc agggcaccct ggtcaccgtg      420
agcagcgcta gcaccaaggg cccatccgtc ttccccctgg cacctcctc aagagcacc      480 tctgggggca cagctgccct gggctgcctg gtcaaggact acttccccga accagtgacc     540
gtgtcctgga actcaggcgc cctgaccagc ggcgtgcaca ccttccctgc tgtcctgcag     600
tcctcaggac tctactccct cagcagcgtg gtgactgtgc cctctagcag cttgggcacc     660
cagacctaca tctgcaacgt gaatcacaag cccagcaaca ccaaggtgga caagaaagtt     720
gagcccaaat cttgtgataa aactcatacc tgccccccct tgtcctgcac agaactgctg     780
ggaggaccat ccgtgttcct gtttccaccc aagcctaaag acaccctgat gatttcccgc     840
acacccgagg tcacttgcgt ggtcgtggac gtgtctcacg aggaccccga agtcaagttc     900
aactggtacg tggatggcgt cgaagtgcat aatgctaaga ccaaaccaag ggaggaacag     960
tacaactcca catatcgcgt cgtgtctgtc ctgactgtgc tgcaccagga ttggctgaac    1020
ggcaaagagt ataagtgcaa agtgagcaat aaggccctgc ccgctcctat cgagaaaact    1080
attagcaagg ctaaagggca gcctcgcgaa ccacaggtgt acaccctgcc tccatctcgg    1140
gaggaaatga ctaagaacca agtcagtctg tggtgtctgg tgaaagggtt ctatcctagc    1200
gacattgcag tggagtggga atccaatgga cagccagaga acaattacaa gaccacaccc    1260
cctgtgctgg actcagatgg aagcttcttt ctgtatagta agctgaccgt ggataaatca    1320
cgctggcagc agggcaacgt ctttttcttgt agtgtgctgc atgaagccct gcacaatcat    1380
tacacacaga agtcactgag cctgtcccct ggcaaatgaa ggatcc                   1426

<210> SEQ ID NO 42
<211> LENGTH: 774
<212> TYPE: DNA
<213> ORGANISM: Artificial Sequence
<220> FEATURE:
<223> OTHER INFORMATION: Tras-optimized Fc

<400> SEQUENCE: 42
atgaactttg gcctgagcct gattttctc gtcctgatcc tgaagggcgt gcagtgtgag       60
gtgcagctgg tggagagcgg cggcggcctg gtgcagcccg gcggcagcct gcgcctgtcc     120
tgcgccgcca gcggcttcac cttttgccgac tacaccatgg actgggtgcg ccaggctccc    180
ggcaagggcc tggagtgggt ggccgacgtg aaccccaaca gcggcgccag catctacaac    240
cagcgcttca gggccgcttc acccctgagc gtggaccgca gcaagaacac cctgtacctg    300
cagatgaaca gcctgcgcgc cgaggacacc gccgtgtact actgcgcccg caacctgggc    360
cccagcttct acttcgacta ttggggcag ggcaccctgg tcaccgtgag cagcgctagc     420
accaagggcc catccgtctt ccccctggca cctcctcca gagcacctc tgggggcaca    480 gctgccctgg ctgcctggt caaggactac ttccccgaac cagtgaccgt gtcctggaac    540
tcaggcgccc tgaccagcgg cgtgcacacc ttccctgctg tcctgcagtc ctcaggactc    600
tactccctca gcagcgtggt gactgtgccc tctagcagct gggcaccca gacctacatc    660 tgcaacgtga atcacaagcc cagcaacacc aaggtggaca agaaagttga gcccaaatct    720
tgtgacaaag gcgagggag cggcggaggc tccgaggcg cagcggagg cgga             774

<210> SEQ ID NO 43
<211> LENGTH: 1429
<212> TYPE: DNA
<213> ORGANISM: Artificial Sequence
<220> FEATURE:
```

<223> OTHER INFORMATION: Tras_HC_hole

<400> SEQUENCE: 43

| | | | | | |
|---|---|---|---|---|---|
| gaattcgcca | ccatgaactt | tggcctgagc | ctgattttc | tcgtcctgat | cctgaagggc | 60
| gtgcagtgtg | aggtgcagct | ggtggagtct | ggaggagggc | tggtgcagcc | aggagggtcc | 120
| ctgagactgt | cttgcgccgc | tagtggcttc | aacatcaagg | acacctacat | ccactgggtg | 180
| agacaggccc | ccggaaaagg | cctggagtgg | gtggccagga | tctaccctac | caccggctac | 240
| accaggtacg | ccgacagcgt | gaagggcagg | ttcaccatca | gcgccgacac | cagcaagaac | 300
| accgcctacc | tgcagatgaa | cagcctgagg | gccgaggaca | ccgccgtgta | ctactgcagc | 360
| agatggggcg | gcagcggctt | ctacgccatg | gactactggg | gacagggcac | actggtcact | 420
| gtgtctagtg | cctcaacaaa | ggggcctagc | gtgtttccac | tggctccctc | aagcaaaagc | 480
| acttccggag | gcaccgctgc | actgggatgt | ctggtgaagg | actacttccc | agagcccgtc | 540
| accgtgtctt | ggaacagtgg | ggctctgacc | agcggagtcc | acacatttcc | tgcagtgctg | 600
| cagtcctctg | gcctgtacag | cctgagttca | gtggtcacag | tcccaagctc | ctctctgggg | 660
| acccagacat | atatctgcaa | cgtgaatcac | aagccaagca | atactaaagt | cgacaagaaa | 720
| gtggagccca | gagctgtga | taaaactcat | acctgccccc | cttgtcctgc | accagaactg | 780
| ctggaggac | catccgtgtt | cctgtttcca | cccaagccta | agacacccct | gatgatttcc | 840
| cgcacacccg | aggtcacttg | cgtggtcgtg | gacgtgtctc | acgaggaccc | cgaagtcaag | 900
| ttcaactggt | acgtggatgg | cgtcgaagtg | cataatgcta | agaccaaacc | aagggaggaa | 960
| cagtacaact | ccacatatcg | cgtcgtgtct | gtcctgactg | tgctgcacca | ggattggctg | 1020
| aacggcaaag | agtataagtg | caaagtgagc | aataaggccc | tgcccgctcc | tatcgagaaa | 1080
| actattagca | aggctaaagg | gcagcctcgc | gaaccacagg | tgtacaccct | gcctccatct | 1140
| cgggaggaaa | tgactaagaa | ccaagtcagt | ctgagctgtg | ccgtgaaagg | gttctatcct | 1200
| agcgacattg | cagtggagtg | ggaatccaat | ggacagccag | agaacaatta | caagaccaca | 1260
| cccccctgtgc | tggactcaga | tggaagcttc | tttctggtga | gtaagctgac | cgtggataaa | 1320
| tcacgctggc | agcagggcaa | cgtcttttct | tgtagtgtgc | tgcatgaagc | cctgcacaat | 1380
| cattacacac | agaagtcact | gagcctgtcc | cctggcaaat | gaaggatcc | | 1429

<210> SEQ ID NO 44
<211> LENGTH: 1360
<212> TYPE: DNA
<213> ORGANISM: Artificial Sequence
<220> FEATURE:
<223> OTHER INFORMATION: gTra_HC_vNT_DT_ML minus signal peptide

<400> SEQUENCE: 44

| | | | | | |
|---|---|---|---|---|---|
| gaggtgcagc | tggtggagtc | tggaggaggg | ctggtgcagc | aggagggtc | cctgagactg | 60
| tcttgcgccg | ctagtggctt | caacatcaag | gacacctaca | tccactgggt | gagacaggcc | 120
| cccggaaaag | gcctggagtg | ggtggccagg | atctacccta | ccaccggcta | caccaggtac | 180
| gccgacagcg | tgaagggcag | gttcaccatc | agcgccgaca | ccagcaagaa | caccgcctac | 240
| ctgcagatga | acagcctgag | ggccgaggac | accgccgtgt | actactgcag | cagatggggc | 300
| ggcaccggct | tctacgccat | ggactactgg | ggacagggca | cactggtcac | tgtgtctagt | 360
| gcctcaacaa | aggggcctag | cgtgtttcca | ctggctccct | caagcaaaag | cacttccgga | 420
| ggcaccgctg | cactgggatg | tctggtgaag | gactacttcc | cagagcccgt | caccgtgtct | 480
| tggaacagtg | gggctctgac | cagcggagtc | cacacatttc | ctgcagtgct | gcagtcctct | 540

```
ggcctgtaca gcctgagttc agtggtcaca gtcccaagct cctctctggg gacccagaca      600
tatatctgca acgtgaatca caagccaagc aatactaaag tcgacaagaa agtggagccc      660
aagagctgtg ataaaactca tacctgcccc ccttgtcctg caccagaact gctgggagga      720
ccatccgtgt tcctgtttcc acccaagcct aaagacaccc tgatgatttc ccgcacaccc      780
gaggtcactt gcgtggtcgt ggacgtgtct cacgaggacc ccgaagtcaa gttcaactgg      840
tacgtggatg gcgtcgaagt gcataatgct aagaccaaac caagggagga acagtacaac      900
tccacatatc gcgtcgtgtc tgtcctgact gtgctgcacc aggattggct gaacggcaaa      960
gagtataagt gcaaagtgag caataaggcc ctgcccgctc ctatcgagaa aactattagc     1020
aaggctaaag ggcagcctcg cgaaccacag gtgtacaccc tgcctccatc tcgggaggaa     1080
atgactaaga accaagtcag tctgacctgt ctggtgaaag ggttctatcc tagcgacatt     1140
gcagtggagt gggaatccaa tggacagcca gagaacaatt acaagaccac accccctgtg     1200
ctggactcag atggaagctt ctttctgtat agtaagctga ccgtggataa atcacgctgg     1260
cagcagggca acgtcttttc ttgtagtgtg ctgcatgaag ccctgcacaa tcattacaca     1320
cagaagtcac tgagcctgtc ccctggcaaa tgaaggatcc                           1360
```

BIPARATOPIC AND MULTIPARATOPIC ANTIBODIES WITH COMMON LIGHT CHAIN AND METHOD OF USE

CROSS REFERENCE TO RELATED APPLICATIONS

This application is a 35 U.S.C. 371 national phase entry of PCT/US2018/026759, filed Apr. 9, 2018, which claims the benefit of U.S. Provisional patent application No. 62/483,456, filed on Apr. 9, 2017, each of which is incorporated herein by reference in its entirety for all purposes.

TECHNICAL FIELD

This invention relates to biparatopic and multiparatopic antibody constructs in which each antibody construct comprises two or more distinct paratopes. The distinct paratopes interact with different epitopes either from the same antigen or from two different antigens. These bispecific antibodies comprise at least two different heavy chain variable domains each paired with a common light chain variable domain. Provided are methods of making such. Also disclosed are uses thereof to diagnose and to treat human diseases.

BACKGROUND OF THE INVENTION

Human epidermal growth factor receptor 2 (HER2, also known as ErbB2) is a member of the ErbB family of receptor tyrosine-protein kinases. It is a type I membrane protein, with a single-pass transmembrane domain, an extra cellular domain and a cytoplasmic kinase domain. Through its domain II of the extra cellular domain, HER2 forms hetero dimers with other ErbB family members, such as EGFR (ErbB1 or HER1), HER3 (ErbB3), or HER4 (ErbB4). The HER2 gene is amplified (HER2$^+$) in about 20% of breast cancer patients. Targeting HER2 with monoclonal antibodies has been shown to be very efficacious in treating HER2 amplified breast cancer patients. The murine anti-HER2 monoclonal antibody 4D5 (mAb 4D5) targets HER2 specifically in HER2-overexpressing cancer cells (U.S. Pat. No. 5,821,337), by binding domain IV of the extracellular domain of HER2. Trastuzumab (Herceptin®), a humanized version of mAb 4D5, was approved by FDA in 1998 for treating HER2$^+$ breast cancer. It works by inhibiting HER2 mediated cell signaling, and also through antibody-dependent cellular cytotoxicity (ADCC), involving effector cells in peripheral blood, such as NK cells and macrophages.

Although HER2 is a receptor tyrosine kinase, it does not have any physiological cognate ligand. Instead, it forms heterodimer with another member of the ErbB family, such as EGFR, HER3 or HER4 that binds to their cognate ligand EGF, heregulins 1 & 2, and heregulins 3 & 4, respectively. Pertuzumab (rhuMab 2C4, PERJETA®, U.S. Pat. No. 7,862,817) is another humanized anti-HER2 monoclonal antibody, but binds to the domain II of the HER2 ECD, a separate epitope on HER2 than that of trastuzumab. Because the domain II of the HER2 ECD is involved in dimerization, binding of pertuzumab to HER2 prevents HER2 from dimerizing with another receptor, such as EGFR, HER3 or HER4. Combination of pertuzumab with trastuzumab showed superior efficacy than trastuzumab or pertuzumab alone, and has been approved by FDA to HER2$^+$ metastatic breast cancer (2012) and a year later in neoadjuvant setting of HER2$^+$ breast cancer (2013).

Targeting two antigens or two epitopes on the same antigen with one biparatopic molecule has been shown to be superior to targeting with an individual antibody alone, or with a combination of two separate antibodies. An example for the former case is a biparatopic molecule called dual variable domain immunoglobulin (DVD-Ig, Gu J. et al., *PLoS One* 10(5):e0124135, 2015) that targets both HER3 and EGFR. An example for the latter case is a DVD-Ig molecule in which both paratopes target HER2, but at two different epitopes (Gu J. et al., *PLoS One* 9(5):e97292, 2014), showing significant efficacy improvement over the combination of trastuzumab and pertuzumab in a xenograft tumor model that is resistant to trastuzumab treatment.

However, in the case of the biparatopic DVD-Ig molecule that recognizes two epitopes on HER2, while this DVD-Ig molecule has shown to be an antagonist for several cancer cell lines, it has been shown to have agonistic activity for N87 cancer cell line (Gu et al., 2014).

Alternatively, a biparatopic molecule can be constructed in other formats, such as a heterodimer mAb with two different heavy chains. When two different light chains are used, there is possibility of incorrect heavy chain-light chain paring that results in non-functional paratopes, in addition to the correct paring of the heavy chain and light chain to generate paratope A and paratope B.

One of the strategies to overcome the incorrect heavy chain and light chain pairing is to use a common light chain. It has been disclosed in the art that targeting both domain II and domain IV of HER2, engineered from trastuzumab and pertuzumab. US20170029529 disclosed a biparatopic molecule with heterodimer format using a common light chain based on the pertuzumab light chain, except using the CDR-L3 from trastuzumab.

WO2016110267 disclosed another biparatopic molecule with heterodimer format using a common light chain based on the light chain of pertuzumab or trastuzumab, with either Thr or Ile substitutions at residues 31 in CDR-L1 and substitutions of Thr or Tyr at residue 94 in CDR-L3, respectively. In this case, the binding affinity has not maintained for both paratopes.

SUMMARY

The presently disclosed embodiments relate to multiparatopic antibody constructs, especially biparatopic antibody constructs having specificity for at least two epitopes in the same antigen or in different antigens. These antibody constructs comprise a common light chain capable of pairing with a least two different heavy chain variable domains to form a functional paratope. The multiparatopic antibody constructs are useful in treating cancers in which the antigens recognized (bound) by the antibody constructs paratopes are expressed in the tumor.

In some embodiments the multiparatopic antibody construct comprises a first paratope that recognizes (binds to) domain II of HER2. In some embodiments this paratope is derived from pertuzumab.

In some embodiments the multiparatopic antibody construct comprises a second paratope that recognizes (binds to) domain IV of HER2. In some embodiments this paratope is derived from trastuzumab.

In some embodiments the multiparatopic antibody construct comprises a second paratope that recognizes (binds to) vascular endothelial growth factor receptor 2 (VEGFR2). In some embodiments this paratope is derived from ramucirumab, In still other embodiments the first and/or second paratope is derived from another antibody that recognizes another antigen expressed at the surface of tumor cells including cancerous (neoplastic) cells and cells of the tumor vasculature.

In some embodiments the heavy chain variable domain for one or more of the paratopes is optimized to retain or improve binding of the paratope to the cognate epitope when paired with a common light chain. Optimization can comprise making amino acid substitutions in the variable domain and especially in the CDRs.

In some embodiments the multiparatopic antibody construct comprises an optimized common light chain. The common light chain may be based on the light chain from one of the at least two parental antibodies. The parental light chain may make minimal contribution to the paratope as compared to a typical light chain or as compared to the light chains of other parental antibodies for the particular multiparatopic antibody construct.

Some embodiments relate to a common light chain based on the light chain of trastuzumab, but contains mutations that improve its interaction with the variable domain derived from a second parental antibody. In some embodiments pertuzumab is a second parental antibody. Various embodiments include mutations located at position 56 of CDR-L2 or position 91, 94, or 96 of CDR-L3, for example: S56T, S56A, or S56Y; H91Y, H91F, or H91W; T94Y, T94F, or T94W; or P96Y, P96F, or P96W; or combinations of substitutions at 1, 2, 3, or 4 of these positions. In some embodiments the trastuzumab-related common light chain further comprises a mutation at position 30 of CDR-L1, for example: N30A or N30S, to address stability issues related to deamidation of N30.

Some embodiments relate to a common light chain based on the light chain of ramucirumab, but contain mutations that improve its interaction with the variable domain derived from a second parental antibody. In some embodiments pertuzumab is a second parental antibody. Various embodiments include mutations located at position 55 of CDR-L2 or position 91 or 96 of CDR-L3, for example: D55Y; A91Y; P96Y; or combinations of substitutions at 1, 2, or 3 of these positions.

In embodiments in which one of the paratopes is derived from pertuzumab, the pertuzumab-related heavy chain variable region is unmodified or includes mutations located in CDR-H2 at position 54 or in CDR-H3 at position 98, for example: T30A, T30S, T30N, or T30D; G56A, G56S, or G56T; or a combination of substitutions at each of these positions.

In embodiments in which one of the paratopes is derived from trastuzumab, the trastuzumab-related heavy chain variable region is unmodified or includes mutations located in CDR-H1 at position 30 or in CDR-H2 at position 56, for example: N54S, N54T, or N54A; D98W, D98S, D98T, or D98R; or a combination of substitutions at each of these positions.

In some embodiments the multiparatopic antibody construct is biparatopic. In some embodiments a biparatopic antibody construct has a Fab-Ig format. In some embodiments a biparatopic antibody construct has an Ig-Fab format. In some embodiments a biparatopic construct has a heterodimer format. In some embodiments a biparatopic construct serves has a base to which additional antigen binding domains are added to form multiparatopic antibody constructs with higher valency for one or another of the cognate epitopes, that recognize an increased number of epitopes, or both.

In some embodiments the multiparatopic antibody constructs have modified Fc regions to modulate their ability to meditate various immunological activities, such as ADCC, ADCP, and CDC, or their interaction with affinity purification reagents. In some embodiments the multiparatopic antibody constructs have modified Fc regions to increase their serum half-life. In particular embodiments the modification to increase serum half-life is M428L.

Some embodiments are nucleic acids encoding the multiparatopic antibody constructs, expression vectors incorporating these encoding nucleic acid sequences, and host cells transformed with these expression vectors. In some embodiments the coding sequence has been codon-optimized.

Some embodiments are methods of treatment for cancer in which the multiparatopic antibody construct is administered to a patient in need thereof. In some embodiments the method of treatment further entails surgery, radiation treatment, or the administration of other anti-cancer drugs including chemotherapeutics, targeted-therapeutics, and hormone treatments. In some embodiments the multiparatopic antibody construct is conjugated to a drug. Still other embodiments relate to use of the multiparatopic antibody construct in the treatment of cancer or in the manufacture of a medicament for the treatment of cancer, and compositions comprising the multiparatopic antibody constructs for use in the treatment of cancer.

BRIEF DESCRIPTIONS OF THE DRAWINGS

FIG. 1: Alignment of the amino acid sequences of the variable domains of the light chain of the anti-HER2 monoclonal antibodies trastuzumab and pertuzumab. Numbering is based on Vajdos et al., *J. Mol. Biol.* 320:415 (2002), using the Kabat numbering (Kabat et al., NIH publication no. 91-3242, pp 662,680,689 (1991)

FIG. 2: Alignment of the amino acid sequences of the variable domains of the heavy chain of the anti-HER2 monoclonal antibodies trastuzumab and pertuzumab. Numbering is based on Vajdos et al., (2002), using the Kabat numbering.

FIG. 3. Diagram of antibody-A and antibody-B, depicting different domains of these antibodies.

FIG. 4. Diagram of the Fab-Ig format of the biparatopic molecule with a common light chain, engineered from antibody-A and antibody-B.

FIG. 5. Diagram of the Ig-Fab format of the biparatopic molecule with a common light chain, engineered from antibody-A and antibody-B.

FIG. 6. Diagram of the heterodimeric IgG format of the biparatopic molecule with a common light chain, engineered from antibody-A and antibody-B. The knob-in-holes mutations are used (Atwell S et al., *J Mol Biol.* 270(1):26-35, 1997; Merchant A M et al., *Nat Biotechnol.* 16(7):677-81, 1998).

FIG. 7. Diagram of the heterodimeric IgG format of the biparatopic molecule with a common light chain, engineered from antibody-A and antibody-B. The charge pair mutations are used (Gunasekaran K et al., *J Biol Chem.* 285(25): 19637-46, 2010).

Figure 11:
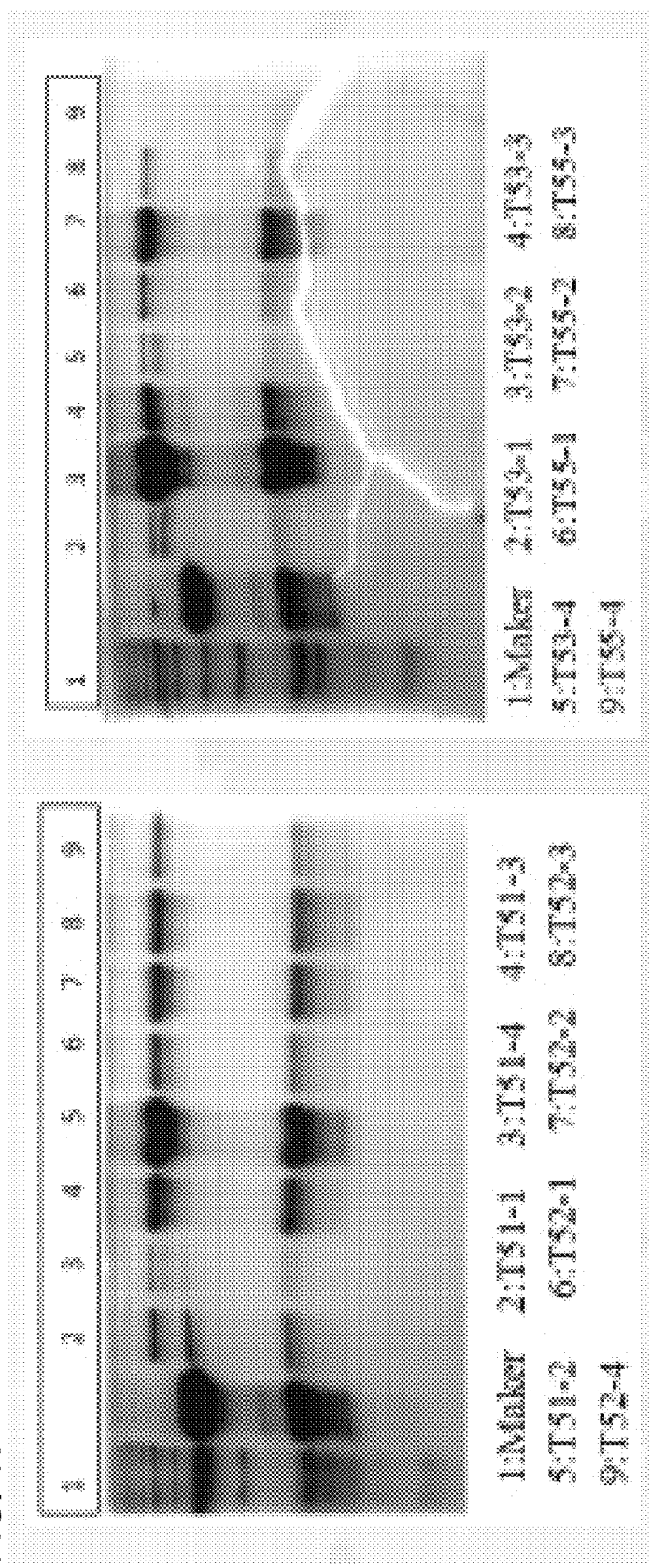
Figure 11:
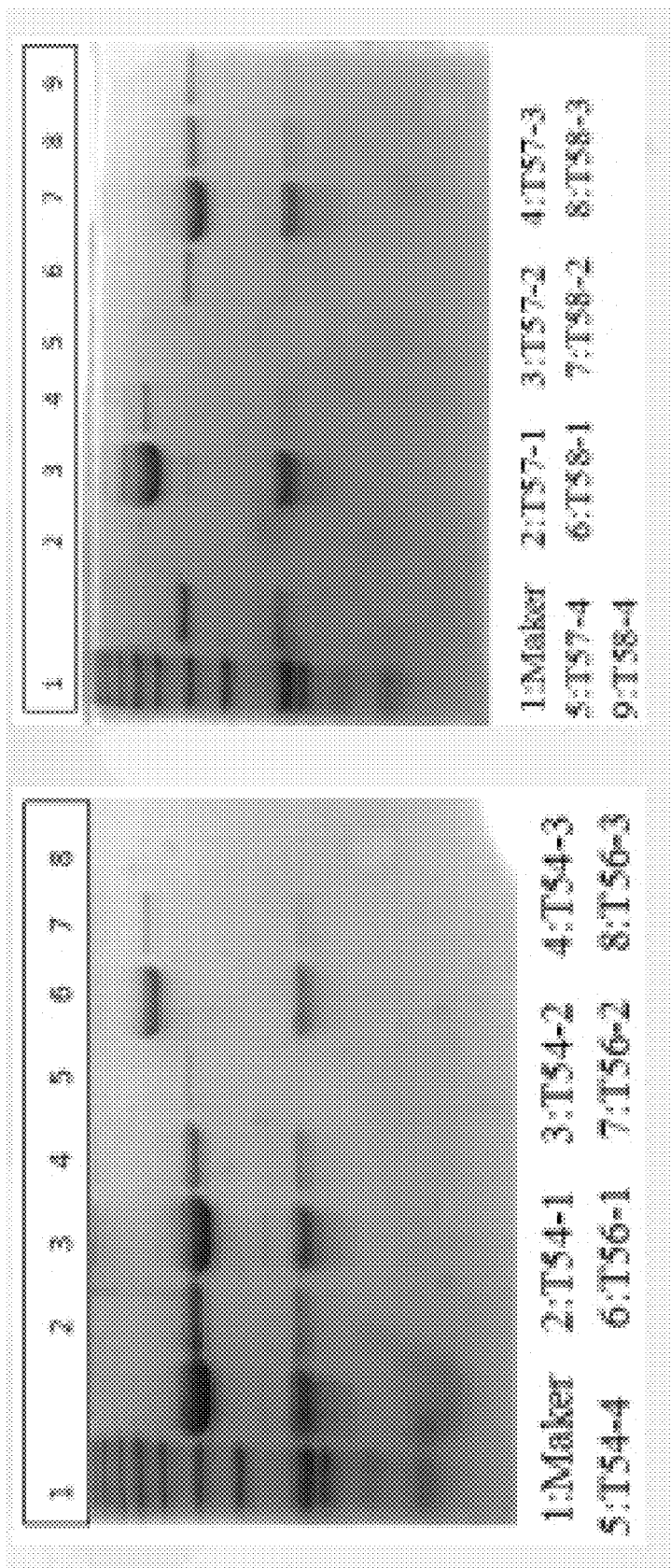

FIG. 11 present polyacrylamide gels following electrophoresis of purified biparatopic antibody constructs T51 and T54 expressed in mammalian cell HEK293.

FIG. 12 depicts (A) the binding potency of biparatopic antibody constructs by ELISA and (B) their EC50.

Figure 13:
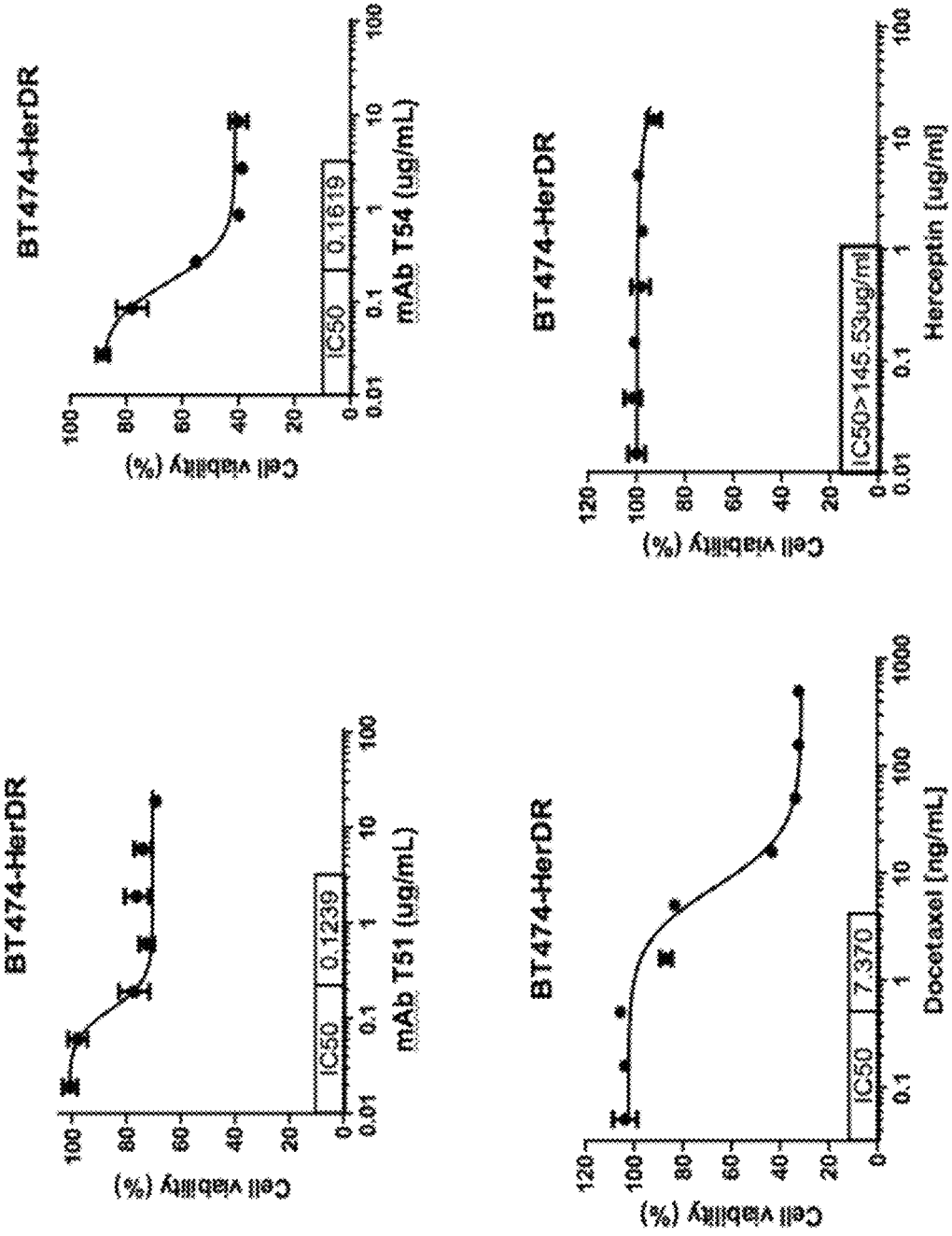

FIG. 13 depicts the effect of (A) biparatopic antibody construct T51 and (B) T54 in inhibiting the growth of the HERCEPTIN-drug resistant BT474 breast cancer cell line.

Figure 14B:
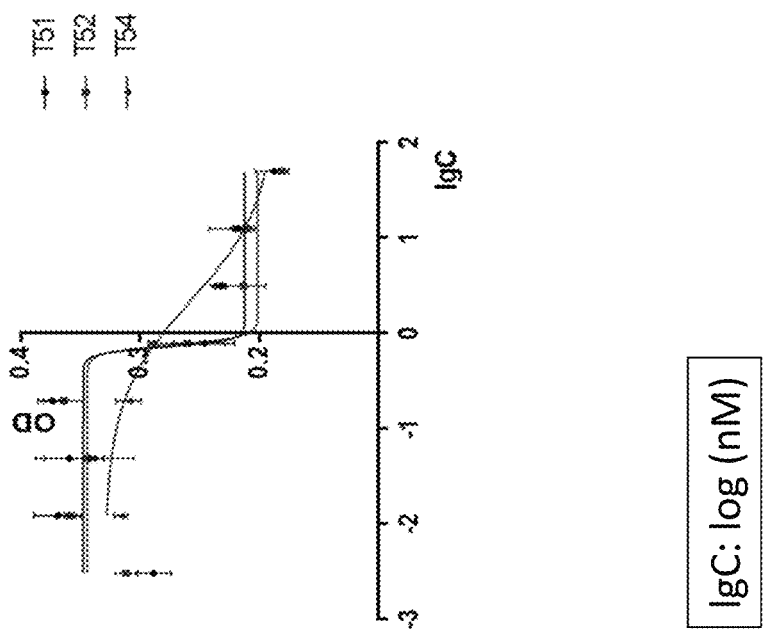
Figure 14A:
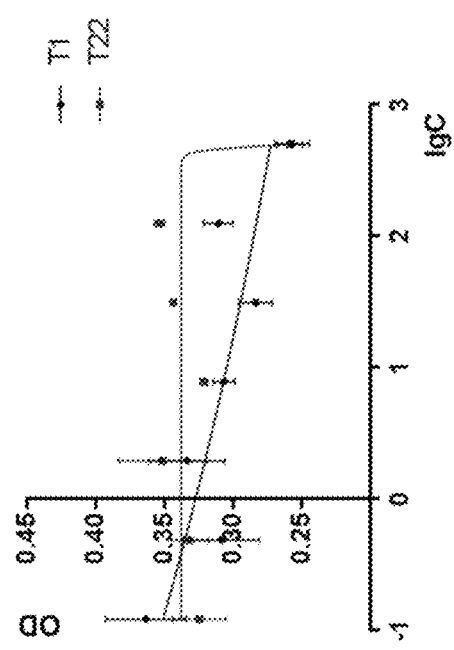
Figure 14C:
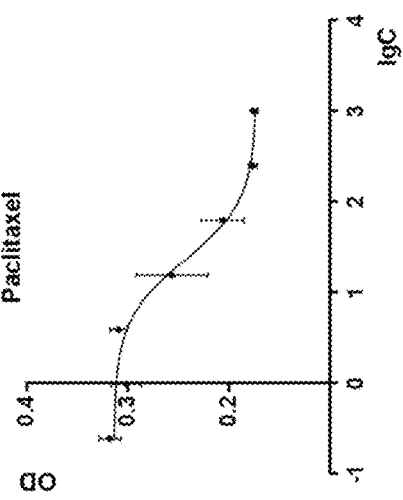

FIG. 14 depicts the effect of (A) biparatopic antibody construct T51 and (B) T54 in inhibiting the growth of the NCI-N87 gastric cancer cell line.

DETAILED DESCRIPTION

Disclosed herein are bispecific antibody constructs that each comprise at least two antigen recognition sites (paratopes) from two different parent antibodies (as depicted, in FIG. 3) that recognize two distinct epitopes either from the same antigen or from two different antigens. These biparatopic molecules comprise copies of one common light chain and one or more copies of two different heavy chain variable domains on the same heavy chain or in two different heavy chains.

As used herein the term "antibody" refers to molecules having the general structure of a naturally occurring mammalian immunoglobulin (Ig) of which IgG is paradigmatic. That is, two identical light chains comprising one variable domain and one constant domain and two identical heavy chains comprising one variable domain and three constants domains. A light chain and a heavy chain associate with each other through their variable domains and the constant domain of the light chain with the first constant domain of the heavy chain. The two heavy chains associate with each other through the 2nd and 3rd constant domains. The antibody's antigen binding site is formed by the two variable domains and especially by the three complementarity determining regions (CDRs) of each variable domain. An antibody is said to bind a molecule (an antigen) if it is capable of specifically interacting with and adsorbing to the molecule. Antibody binding does not include non-specific or low-affinity interactions. Although "antibody" is intended to connote the naturally occurring structure of immunoglobulins it nonetheless include engineered molecules retaining this general structure, such as chimeric, CDR-grafted, and humanized antibodies.

As used herein the term "antibody construct" refers to molecules in which the general structure of naturally occurring mammalian immunoglobulins has been modified, especially by—but not necessarily limited to—engineering the association of two non-identical heavy chains or adding additional domains. In preferred embodiments disclosed herein the additional domains form a structure corresponding to an antibody Fab fragment (fragment of antigen binding). In other embodiments further additional domains of an antibody construct can form a structure corresponding to other antibody fragments such as Fv (variable fragment, consisting of VH and VL), single-chain Fv (scFv), or some other antigen-binding portion of an antibody.

As used herein the term "parental antibody" refers to one or another of the antibodies from which the paratopes of the multiparatopic antibody construct is derived. By derived it is meant that the amino acid sequence information for the paratope was obtained from the parental antibody. Additional amino acid sequence information, other than that for the paratope, may be obtained from the parental antibody. It should be understood that the amino acid sequences of the variable domains that form the paratope in the parental antibodies may be used unmodified or they may be modified, for example to optimize formation and affinity of the paratope when using a common light chain.

As used herein the term "epitope" refers to that part of an antigen that mediates antigen-specific binding with an antibody by making contact with the antigen binding site of the antibody (or antibody construct).

As used herein the term "paratope" refers to that part of an antibody (or antibody construct) that mediates antigen-specific binding with an antigen by making contact with the epitope of the antigen.

As used herein the term "biparatopic antibody construct" indicates a construct having two distinct epitope-binding sites. The antibody construct can be monovalent, bivalent, or multivalent for one or both of the paratopes.

As used herein the term "common light chain" refers to an immunoglobulin light chain comprising a variable domain that can productively associate with multiple heavy chain variable domains to form a paratope with each heavy chain variable region that is capable of specifically binding the epitope bound by the antibody in which the heavy chain variable region was originally encountered.

Various antibody heavy or light chains, or portions thereof, are referred to herein as being "related" to the corresponding chain or portion thereof of an enumerated or specifically identified antibody. This denotes that the chain or portion thereof has identical sequence to the corresponding chain or portion thereof of an enumerated or specifically identified antibody, save for specifically indicated modifications, such as amino acid substitutions, of which there may be none. In alternative embodiments the related chain or portion thereof has at least 90, 95, 96, 97, 98, or 99 percent sequence identity with to the corresponding chain or portion thereof of an enumerated or specifically identified antibody.

As used herein the terms "modification", "mutation", and "substitution" (and grammatical forms thereof) refer to engineered changes in amino acid sequence. Unless context dictates otherwise, mutation does not refer to sequence changes arising from unaided biological processes. Substitutions shall be denoted conventionally with an amino acid in single letter code from the reference sequence, a position in the reference sequence, and amino acid in single letter code from the resultant sequence. For example A26S would indicate that the alanine at the 26th position in the reference sequence has be changed to a serine in the resultant sequence.

Several different overall architectures can be adopted for the disclosed antibody constructs. The description of these antibody constructs will focus on biparatopic antibody constructs but it is to be understood that additional variable domains may be added to each heavy chain so that the heavy chain comprises, for example, 3, 4, 5, or more, variable domains that contribute to the formation of the same number of paratopes. In these multiparatopic antibodies the 3rd paratope may confer specificity for a 3rd epitope, making the antibody construct tri-specific. Alternatively, the 3rd paratope may be specific for one of the epitopes recognized by either of the first two paratopes, so that the antibody construct remains bispecific, but has increased valency for one of the epitopes. Similarly, a 4th paratope may be specific for a 4th epitope so that the antibody construct is tetraspecific, or it may be specific for one of the epitopes recognized by any of the first three paratopes so that the antibody construct is tri- or bispecific. And so on.

The bi- or multiparatopic antibody construct comprises two or more copies of a common light chain that contains one or more mutations as disclosed herein and have of variable domain or the derivative thereof with >80 identity, 85% identity, >90% identify, >95% identity, >98% identity to the unaltered sequence upon which it is based.

The biparatopic antibody constructs can be in a homodimer format (comprising two identical heavy chains), such as Fab-Ig (as depicted in FIG. 4) or Ig-Fab (as depicted in FIG. 5). In the Fab-Ig format, the second heavy chain variable domain ($V_H^B$) and CH1 are fused to the N-terminus of the heavy chain of the first antibody ($V_H^B$-CH1-linker-$V_H^A$-$C_{H1}$-hinge-$C_{H2}$-$C_{H3}$, FIG. 4). In Ig-Fab format, the second heavy chain variable domain ($V_H^B$) and $C_{H1}$ are fused to the C-terminus of the Fc domain (fragment crystallizable, consisting essentially of the $C_{H2}$ and $C_{H3}$ domains) of the first antibody ($V_H^A$-$C_{H1}$-hinge-$C_{H2}$-$C_{H3}$-linker-$V_H^B$-$C_{H1}$), which has its variable domain ($V_H^A$) in the canonical position (FIG. 5). Higher order multiparatopic antibody constructs can contain further variable domains appended to the N- or C-terminal ends of these basic designs. The linker consists of 0 to 100 amino acids of any composition. In some preferred embodiment, the linker is $(G_4S)n$, or $(G_2SG_2)n$, where n is any number between 1 to 20. In some other preferred embodiments, the linker comprises full or part of the hinge region of immunoglobulins (IgG, IgA, IgM, IgD), or human serum albumin loop sequence). When these heavy chain constructs are expressed together with a common light chain, each molecule has two distinct bivalent paratopes (four antigen binding sites all together).

The biparatopic molecule can also be in a heterodimer Ig format. Two different heavy chains from the two different antibodies can form heterodimers using technologies described in the art, including but not limited to, the knobs-into-holes (FIG. 6, Ridgway J B, *Protein Engineering* 9:617, 1996), or electrostatic steering mechanism (FIG. 7, Gunasekaran K et al., 2010). When paired with the common light chain, the molecule has two distinct monovalent paratopes (just two antigen binding sites as in a natural IgG molecule).

The constant regions ($C_{H1}$, $C_{H2}$, and $C_{H3}$) are of human immunoglobulins, such as IgG, IgM, IgA, IgD. or IgG and its subtypes IgG1, IgG2, IgG3, IgG4; or a combination of recombined $C_{H1}$, $C_{H2}$, and $C_{H3}$ domains from these types and subtypes.

To eliminate incorrect pairing of the heavy and light chains of the two paratopes, a common light chain is used. The common light chain is chosen by identifying a monoclonal antibody in which the paratope mainly consists of residues from the heavy chain. Upon search of a database of structures of antibodies complexed with their cognate antigens, pertuzumab emerged as a good candidate as a source of a light chain variable domain that makes minimal contribution to the paratope. The majority of pertuzumab's interactions with its epitope in domain II of the HER2 ECD are from its heavy chain (Franklin et al., *Cancer Cell* 5:317-328, 2004). Only three residues from the light chain are involved in interacting with HER2 and are in the complementarity determining regions (CDRs) 2 and 3: Y49 and Y55 of CDR-L2, and Y94 of CDR-L3 (Kabat numbering system, FIG. 1).

For the second parental antibody used to generate the biparatopic molecule, there is no requirement that the paratope consists mainly of heavy chain. As an example, trastuzumab is used as the source of the second paratope.

Creating a Common Light Chain

A common light chain was engineered using the light chain of trastuzumab as the starting point (FIG. 1). Changes were made in the variable domain and the native constant domain was retained. However, in alternative embodiments the constant domain is replaced with any human light chain K or A constant domain. Since residues Y49 and Y55 of the pertuzumab light chain CDR-L2, which are involved in binding to HER2, are also Tyr in trastuzumab, two approaches were pursued to generate a common light chain: The first was to use CDR-L3 of pertuzumab, and mutate the residues in CDR-L1 and CDR-L2 of trastuzumab to the residue in pertuzumab. The second approach was to mutate residue 94 of CDR-L3 to each of the other 19 standard genetically-encoded amino acids. These light chains were first tested with the heavy chain of trastuzumab and pertuzumab separately, to select the mutations that retained biding to both domain IV and II, respectively, of HER2 ECD. The best performing light chain is used as a common light chain. In a preferred embodiment T94 is mutated to Tyr (T94Y), as found naturally in pertuzumab. In some other preferred embodiments, T94 is mutated to Phe (T94F). And yet in some other preferred embodiments, T94 is mutated to Trp (T94W).

In some embodiments, the common light chain is further optimized. For example, N30 of CDR-L1 of trastuzumab light chain can be mutated to another residue, such as N30S, to eliminate the hot spot of deamidation that was known in the art for trastuzumab. In some embodiments, N30S and T94Y are combined (N30S/T94Y). In some other preferred embodiments, N30S is combined with T94F mutation (N30S/T94F). And yet in some other preferred embodiments, N30S is combined with T94W mutation (N30S/T94W).

In some preferred embodiments, the N30 in the common light chain is mutated to A (N30A). In some embodiments, N30A and T94Y are combined (N30A/T94Y). In some other preferred embodiments, N30A is combined with T94F mutation (N30A/T94F). And yet in some other preferred embodiments, N30A is combined with T94W mutation (N30A/T94W).

A third approach to optimize the common light chain involves mutating residue H91 of CDR-L3 to the other 19 standard genetically-encoded amino acids. In some preferred embodiments, H91 is mutated to Tyr (H94Y), as found in pertuzumab. In some other preferred embodiments, H91 is mutated to Phe (H94F). And yet in some other preferred embodiments, H91 is mutated to Trp (H91W).

In some embodiments, the common light chain is further optimized, including combination with other mutations, such as N30S, N30A.

In some embodiments, N30S and H91Y are combined (N30S/H91Y). In some other preferred embodiments, N30S is combined with the H91F mutation (N30S/H91F). And yet in some other preferred embodiments, N30S is combined with H91W mutation (N30S/H91W).

In some preferred embodiments, the N30 in the common light chain is mutated to A (N30A). In some embodiments, N30A and H91Y are combined (N30A/H91Y). In some other preferred embodiments, N30A is combined with H91F mutation (N30A/H91F). And yet in some other preferred embodiments, N30A is combined with H91W mutation (N30A/H91W).

A fourth approach to optimizing the common light chain involves mutating residue P96 of CDR-L3 to each of the other 19 standard genetically-encoded amino acids. In some preferred embodiments, P96 is mutated to Tyr (P96Y), as in pertuzumab. In some other preferred embodiments, P96 is mutated to Phe (P96F). And yet in some other preferred embodiments, P96 is mutated to Trp (P96W). In some embodiments, the common light chain is further optimized, including combination with other mutations, such as N30S, N30A.

In some embodiments, N30S and P96Y are combined (N30S/P96Y). In some other preferred embodiments, N30S is combined with P96F mutation (N30S/P96F). And yet in some other preferred embodiments, N30S is combined with P96W mutation (N30S/P96W).

In some preferred embodiments, the N30 in the common light chain that is mutated to A (N30A). In some embodiments, N30A and P96Y are combined (N30A/P96Y). In some other preferred embodiments, N30A is combined with P96F mutation (N30A/P96F). And yet in some other preferred embodiments, N30A is combined with P96W mutation (N30A/P96W).

A fifth approach to optimizing the common light chain involves mutating residue S56 of CDR-L2 to each of the other 19 standard genetically-encoded amino acids. In some embodiments S56 is mutated to Thr, as in pertuzumab. In preferred embodiments S56 is mutated to Tyr (S56Y). In some embodiments, the common light chain is further optimized, including combination with other mutations, such as N30S, N30A. In some preferred embodiments N30S and S56Y are combined (N30A/S56Y).

In some embodiments, the common light chain has a combination of substitutions at any or all of the positions described above. For example, a preferred embodiment having a combination of three substitutions is N30S/S56Y/T94W. In some embodiments one or more individual substitutions are specifically excluded, either generally or with respect to a particular multiparatopic antibody construct (such as, Fab-Ig, Ig-Fab, or heterodimer). For example, in some embodiments T94Y is completely excluded, and in other embodiments T94Y is excluded for biparatopic antibodies in the heterodimer format. Such exclusions may be limited to one or more particular amino acid substitutions at the position in question or may extend to all possible mutations at that position. Some embodiments are permissive of additional mutations. Other embodiments exclude mutations at any position for which mutations are not explicitly described. These teachings are generalizable to common light chains based on light chains other than the trastuzumab light chain and to common light chains pairing with combinations of heavy chain variable domains related to other antibodies than pertuzumab and trastuzumab.

The optimized common light chain molecules are combined with the heavy chain variable domains of pertuzumab and trastuzumab, or their mutants described below.

In alternative embodiments a common light chain can be engineered using the light chain of ramucirumab as the starting point. This ramucirumab-derived common light chain variable region (CDR1, CDR2, and CDR3) comprises mainly light chain residues from ramucirumab, but retains several key amino acid residues from the light chain of pertuzumab, including one or more amino acid residues of Tyr55 in CDR-L2, Tyr91, and Pro96 in CDR-L3 (Kabat numbering scheme). Some of the light chain variable domain residues are conserved between pertuzumab and ramucirumab (Tables 1 and 2) and in some embodiments these residues are retained.

TABLE 1

Amino acid sequence in CDR2 of light chains of pertuzumab and ramucirumab

| | AA # (Kabat scheme) | | | | | | |
|---|---|---|---|---|---|---|---|
| | 50 | 51 | 52 | 53 | 54 | 55 | 56 |
| Pertuzumab | S | A | A | Y | R | Y | T |
| Ramucirumab | D | A | S | N | L | D | T |
| Identical AA | | * | * | | | | * |

(Identical amino acid is indicated by an * underneath the residue)

TABLE 2

Amino acid sequence in the CDR3 of light chain of pertuzumab and ramucirumab

| | AA # (Kabat scheme) | | | | | | | | |
|---|---|---|---|---|---|---|---|---|---|
| | 89 | 90 | 91 | 92 | 93 | 94 | 95 | 96 | 97 |
| Pertuzumab | Q | Q | Y | Y | U | Y | P | Y | T |
| Ramucirumab | Q | Q | A | J | A | F | P | P | T |
| Identical AA | * | * | | | | | * | | * |

(Identical amino acid is indicated by an * underneath the residue)

In some embodiments, the ramucirumab-derived common light chain has a combination of substitutions at any or all of the positions described above. The optimized common light chain molecules are combined with the heavy chain variable domains of pertuzumab and ramucirumab, or their mutants described below.

Optimization of the Heavy Chains of Antibody-A and Antibody-B.

Figure 2:
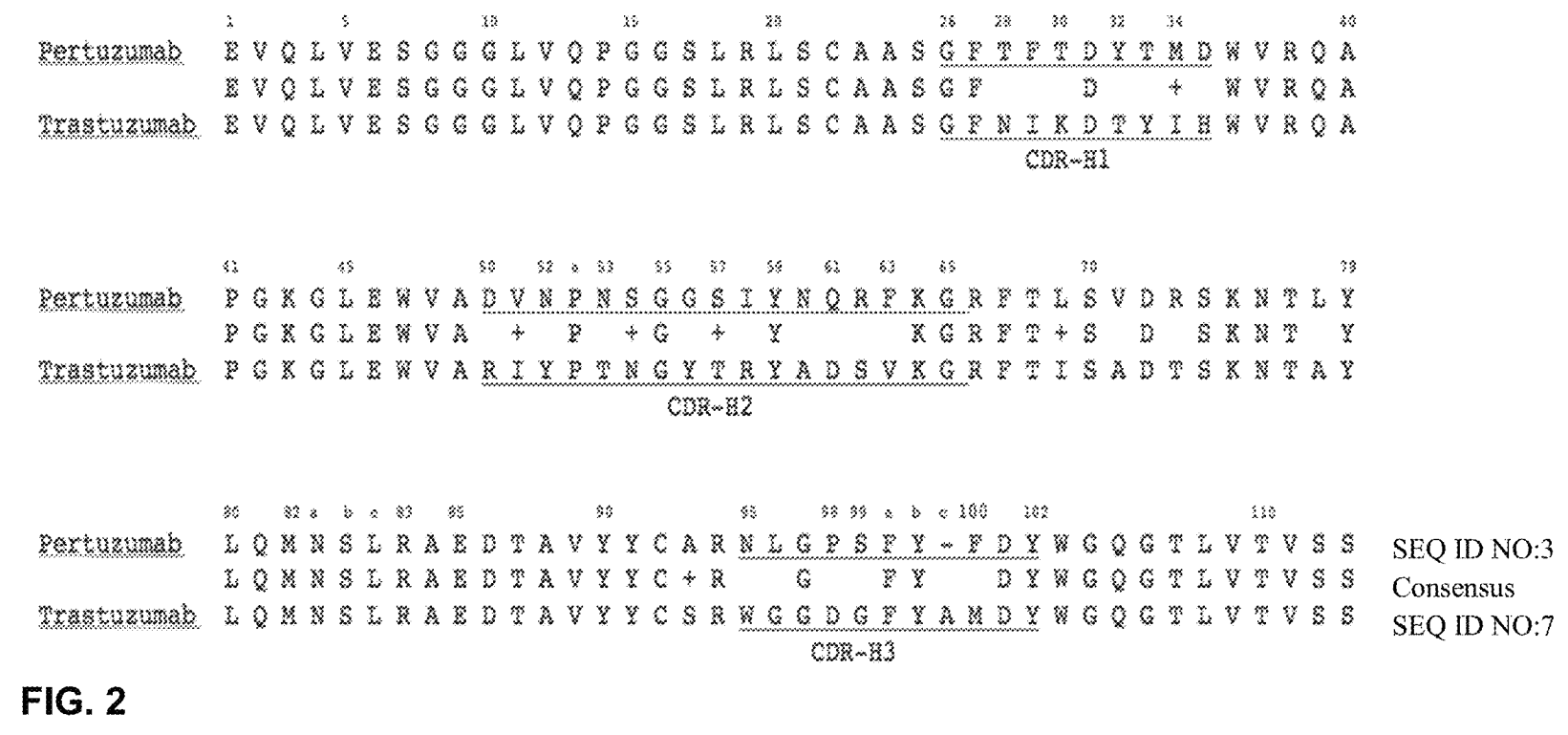

The biparatopic molecules consist of one or more copies of pertuzumab heavy chain variable domain with the following mutated amino acid residues: T30 (Kabat numbering, FIG. 2), such as T30A, T30S, T30N, T30D; and G56 (Kabat numbering, FIG. 2), such as G56A, G56S, G56T, as well combinations of these mutations (such as T30A and G56A).

The biparatopic molecules consist of one or more copies of the trastuzumab heavy chain variable domain with the following mutated amino acid residues: N54 (Kabat numbering, FIG. 2), such as N54S, N54T, N54A; D98 (Kabat numbering, FIG. 2), such as D98W, D98S, D98T, D98R; as well combinations of these mutations (such as N54T and D98W).

In various embodiments a biparatopic antibody construct has a pertuzumab heavy chain variable domain having 0, 1, 2, or more mutations is combined with a trastuzumab heavy chain variable domain having 0, 1, 2, or more mutations. Some embodiments exclude one or more particular substitutions or mutations at a particular position. Other embodiments exclude all mutations at a particular position. Some embodiments are permissive of additional mutations. Other embodiments exclude mutations at any position for which mutations are not explicitly described. In some embodiments these exclusions are applied to a particular multiparatopic antibody construct format, such as Fab-Ig, Ig-Fab, or heterodimer. These teachings are generalizable to multiparatopic antibody constructs comprising heavy chain variable domains related to other antibodies besides pertuzumab and trastuzumab.

In further embodiments other heavy chain variable domains are included in the biparatopic antibody construct instead of the trastuzumab heavy chain variable domain.

Examples of antibodies that are used as the parental second antibody to build biparatopic antibody with pertuzumab as the first antibody include, but are not limited to, an anti-VEGFR2 antibody such as ramucirumab. The common light chain is based on these two antibodies, with the first antibody being pertuzumab, and the second antibody being ramucirumab.

In another embodiment, the second antibody is an anti-EGFR antibody, such as but not limited to certuximab, panitumumab, nimotuzumab, or zalutumumab.

Yet, in another embodiment, the second antibody is an anti-VEGF antibody, such as but not limited to bevacizumab.

In some embodiments, the second antibody is an anti-PD-1 antibody, such as but not limited to pembrolizumab, or nivolumab.

In some embodiments, the second antibody is an anti-PD-L1 antibody, such as but not limited to atezolizumab, or durvalumab.

In some embodiments, the second antibody is an anti-CTLA4 antibody, such as but not limited to ipilimumab.

In some embodiments, the second antibody is anti-CD3 antibody, such as but not limited to OKT3, SP34, or their derivatives, such as humanized, or affinity modified version.

In some aspects, the Fc of the biparatopic molecule contains Fc with increased ADCC, antibody-dependent cellular phagocytosis (ADCP) or complement-dependent cytotoxicty (CDC) activity, resulting from enhanced or deminished binding affinity to Fc receptors, such as CD16a, CD16b, CD32a, CD16b, CD64, and C1q protein. This include but are not limited to ADCC-enhanced afucosylated antibody, obtained either (1) by producing the biparatopic molecules in host cells that are defective in fucosylation, such as knock out of the FUT8 gene (Yamane-Ohnuki N et al., *Biotechnol Bioeng.* 87(5):614-22, 2004); or (2) have S239D, I332E, A330L substitutions (Kabat numbering) or a combination of any or all of these mutations in the Fc domain of the antibody (Lazar G A et al., *Proc Natl Acad Sci USA.* 103(11): 4005-4010, 2006).

In some aspects, the biparatopic molecule contains mutations in the Fc domain to diminish ADCC activity or CDC activity. These can include but are not limited to mutations at (1) N297 in the Fc domain, such as but not limited to N297A, N297G; (2) L234, such as L234A, L234G and/or L235, such as L235A, or L235; (3) P329, such as P329G; or (4) D265, such as D265A; or combinations of these substitutions at any or all of these positions.

In some aspects, the Fc mutations (all numbers are Eu index of Kabat numbering system) include those that increase serum half-life. In one embodiment, the Fc has the following substitutions T250Q, or M428L, or T250Q/M428L double mutations in $CH_3$ (Hinton et al., *J Biol Chem.* 279(8):6213-6, 2004). In another embodiment, the Fc of the biparatopic antibody has the M252Y/S254T/T256E triple mutation (Dall'Acqua W F et al., *J Immunol* 169(9):5171-80, 2002). Yet in another embodiment, the Fc of the biparatopic antibody has the N434A mutation (Petkova S B et al., *International Immunology* 18(12): 1759-1769, 2006.), or M428L/N434S double mutation, or M428/N434A double mutation (Zalevsky J et al., *Nat Biotechnol.* 28(2): 157-159, 2010).

Further embodiments include multiparatopic molecules comprising the biparatopic molecules described herein. In some embodiments, a third, a fourth or even further additional paratopes are added to the biparatopic molecules to generate triparatopic, tetraparatopic, or other multiparatopic molecules. The additional paratope(s) is either another antibody in a Fab format, or dcFv, or scFv format. The additional paratope(s) is a ligand binding domain. These additional paratopes are naturally produced or synthetics prepared.

Methods of Making the Compositions

The antibody constructs disclosed herein (and their component parts) may be produced by recombinant means. Thus, disclosed herein are nucleic acids encoding the antibody constructs, expression vectors containing nucleic acids encoding the antibodies, and cells comprising the nucleic acid encoding the antibody constructs. Methods for recombinant production are widely known in the art and comprise protein expression in prokaryotic and eukaryotic cells with subsequent isolation of the antibody construct and usually purification to a pharmaceutically acceptable purity. For the expression of the antibody constructs as aforementioned in a host cell, nucleic acids encoding the antibody construct sequences are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or *E. coli* cells, and the antibody is recovered from the cells (supernatant or cells after lysis).

Accordingly, certain embodiments disclosed herein include a method for the preparation of an antibody construct, comprising the steps of a) transforming a host cell with at least one expression vector comprising nucleic acid molecules encoding the antibody construct; b) culturing the host cell under conditions that allow synthesis of the antibody construct molecule; and c) recovering said antibody construct molecule from the culture.

The antibody constructs are suitably separated from the culture medium by conventional immunoglobulin purification procedures such as, for example, protein A-Sepharose, hydroxylapatite chromatography, gel electrophoresis, dialysis, or affinity chromatography.

As used herein, the expressions "cell," "cell line," and "cell culture" are used interchangeably and all such designations include progeny. Thus, the words "transformants" and "transformed cells" include the primary subject cell and cultures derived therefrom without regard for the number of passages. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection can be carried out e.g. by the calcium phosphate precipitation method. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride.

As used herein, "expression" refers to the process by which a nucleic acid is transcribed into mRNA and/or to the process by which the transcribed mRNA (also referred to as a transcript) is subsequently translated into peptides, polypeptides, or proteins. The transcripts and the encoded polypeptides are collectively referred to as gene product. If the polynucleotide includes sequences derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The term "host cell" as used herein denotes any kind of cellular system which can be engineered to generate the antibodies disclosed herein. In one embodiment HEK293 cells and CHO cells are used as host cells.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Similarly, in some instances an intron may be present between nucleic acid sequences that are operably linked. Linking is accomplished by ligation at convenient restriction sites. If such sites do not exist, then synthetic oligonucleotide adaptors or linkers are used in accordance with conventional practice.

Nucleic acid sequence encoding the antibody constructs can be readily obtained from the literature, or by reverse translation with reference to preferred codon usage of the intended host cell. Encoding nucleic acids may be assembled from chemically synthesized polynucleotides and/or previously cloned antibody-encoding DNA, possibly aided by site-directed mutagenesis.

For recombinant production of the antibody constructs, the nucleic acid encoding it may be isolated and inserted into a replicable vector for further cloning (amplification of the DNA) or for expression. DNA encoding the antibody construct is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615, specifically incorporated herein by reference for all it discloses regarding protein expression.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *S. typhimurium*, *Serratia*, e.g., *S. marcescans*, and *Shigella*, as well as Bacilli such as *B. subtilis* and *B. licheniformis*, *Pseudomonas* such as *P. aeruginosa*, and *Streptomyces*. One exemplary *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody construct-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *Yarrowia* (EP 402,226); *Pichia pastoris* (EP 183,070); *Candida*; *Trichoderma reesia* (EP 244,234); *Neurospora crassa*; *Schwanniomyces* such as *S. occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibody constructs are derived from multicellular organisms, including invertebrate cells such as plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *B. mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells are transformed with the above-described expression vectors for antibody production and cultured in conventional nutrient media modified as appropriate for inducing promoters, selecting transformants, or amplifying the genes encoding the desired sequences.

The host cells used to produce the antibody constructs may be cultured in a variety of media. Commercially available media such as Ham's F10, Minimal Essential Medium (MEM), RPMI-1640, and Dulbecco's Modified Eagle's Medium (DMEM) are suitable for culturing the host cells. In addition, U.S. Pat. Nos. 4,767,704; 4,657,866; 4,927,762; 4,560,655; or U.S. Pat. No. 5,122,469; WO 90/03430; WO 87/00195; or U.S. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody construct can be produced intracellularly, in the periplasmic space, or directly secreted into the medium. If the antibody construct is produced intracellularly, as a first step, the particulate debris, either host cells or lysed fragments, is removed, for example, by centrifugation or ultrafiltration.

The antibody composition prepared from the cells can be purified using, for example, hydroxyapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains. Protein G is recommended for all mouse isotypes and for human γ3. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody construct to be recovered.

Following any preliminary purification step(s), the mixture comprising the antibody construct of interest and contaminants may be subjected to low pH hydrophobic interaction chromatography using an elution buffer at a pH between about 2.5-4.5, preferably performed at low salt concentrations (e.g., from about 0-0.25 M salt).

Once purified the antibody construct can be dissolved in an aqueous solvent including any pharmaceutically acceptable buffers, salts, or other excipients. The dissolved antibody construct may be stored refrigerated or frozen prior to use. Alternatively it may be lyophilized and reconstituted shortly prior to use.

Methods of Using the Compositions

The present invention also relates to a pharmaceutical composition comprising a biparatopic antibody of the present invention.

The terms "treat" or "treatment" of a state, disorder or condition include: (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein the term "therapeutically effective" or "effective" applied to dose or amount refers to that quantity of a compound or pharmaceutical composition that when administered to a subject for treating (e.g., preventing or ameliorating) a state, disorder or condition, is sufficient to effect such treatment or prophylactic result. The "therapeutically effective amount" will vary depending on the compound or bacteria or analogues administered as well as the disease and its severity and the age, weight, physical condition and responsiveness of the mammal to be treated.

The phrase "pharmaceutically acceptable", as used in connection with compositions of the disclosure, refers to molecular entities and other ingredients of such compositions that are physiologically tolerable and do not typically produce untoward reactions when administered to a mammal (e.g., a human). In some embodiments, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Further embodiments relate to use of a biparatopic antibody construct as presently disclosed for the treatment of cancer. In another embodiment, use of the bispecific antibody as a medicament is provided. Preferably said use is for the treatment of cancer. Similar embodiments comprise use of biparatopic antibody construct, of a common light chain thereof, in the manufacture of a medicament for treating cancer. Other similar embodiments are methods of cancer treatment comprising administering a therapeutically effective amount of the biparatopic antibody construct to a patient in need thereof. In preferred embodiments the patient is a mammal. In especially preferred embodiments the patient is a human.

The compositions of the preferred embodiment described herein can be used for treating diseases. For example, the preferred embodiment anti-HER2 biparatopic molecule based on pertuzumab and trastuzumab can be used to treat cancers such as, but not necessarily limited to, HER2$^+$ breast cancer, gastric cancer, lung cancer and/or ovarian cancer.

The multiparatopic antibody construct composition can be administered alone or in conjunction with other agents suitable for treating cancer. For example, the compositions can be used in combination with other therapeutics, such as for chemotherapy or for targeted therapy, or for immunotherapy. Similarly they can be used in conjunction with radiation therapy or surgery.

The multiparatopic antibody constructs can also be used to make antibody-drug conjugates (ADC). There is a general preference in the art for site specific conjugation, as this can facilitate uniformity of product and stability of linkage. In preferred ADC embodiments using multiparatopic antibody constructs the drug is conjugated to the common light chain, for example in its constant domain or at its C-terminus. This is particularly advantageous in homodimeric formats, such as the Fab-Ig and Ig-Fab formats, as a biparatopic construct will deliver four molecules of the conjugated drug (assuming one conjugation site per light chain), thus doubling the payload of the typical ADC.

The multiparatopic antibody construct composition can be delivered by any suitable route. In some embodiments, the composition is delivered by injection or infusion, by skin patches, by reservoir/pumping devices, or by inhalation. In various aspects of these embodiments the multiparatopic antibody construct composition is administered intravenously, intraperitoneally, subcutaneously, or intramuscularly.

The composition in some embodiments can be administered once a day or less frequently. For example, in some embodiments, the composition is administered once every two days, once every three days, once every four days, once every five days, once every six days, once a week, once every two weeks, once every three weeks, once every four weeks, monthly, every two months, every three months, or every six months.

The optimal dose level of the effective molecule will depend on a variety of factors including the age, body weight, physical condition of the patients, on a possible combination with other drugs, and on the severity of the case of disease. The specific dosage can be determined by those skilled in the art in a similar way as for known cytokine molecule compositions.

Kits, Unit Dosages, and Articles of Manufacture

The present application further provides kits, unit dosages, and articles of manufacture comprising compositions described herein. The kits, unit dosages, and article of manufacture may comprises, for example, vials (such as sealed vials) pre-filled syringes, and auto-injectors (pens) comprising the compositions described herein.

Amino acids are referred to herein by either their commonly known 3-letter symbols or by the 1-letter symbols according to the IUPAC-IUB Biochemical Nomenclature Commission (see Table 3 below).

EXAMPLES

The following Examples use a variety of antibodies and antibody constructs each assigned a mAb number. Tables 3 through 6 identify their heavy and light chain components. Though not indicated in the Tables the biparatopic antibody constructs contain the M428L substitution in the Fc region in order to improve serum half-life as discussed above. Complete amino acid and nucleotide sequences for exemplary biparatopic antibody constructs are presented in Tables 8 and 9, respectively.

TABLE 3

Heavy chain-Light chain pairings
These antibodies pair the pertuzumab heavy chain (Per-HC) or trastuzumab heavy chain (Tra-HC) with either a wild type (WT) or common light chain based on the trastuzumab light chain (Tra_LC) with the indicated amino acid substitution

| mAb# | Heavy chain | Light chain* | Comment |
|---|---|---|---|
| T1 | Per-HC | Per_LC | WT pertuzumab |
| T2 | Per-HC | Tra_LC_N30S | |
| T3 | Per-HC | Tra_LC_L54R | |
| T4 | Per-HC | Tra_LC_S56Y | |
| T5 | Per-HC | Tra_LC_H91F | |
| T6 | Per-HC | Tra_LC_H91Y | |
| T7 | Per-HC | Tra_LC_T94Y | |
| T8 | Per-HC | Tra_LC_T94W | |
| T9 | Per-HC | Tra_LC_T94F | |
| T10 | Per-HC | Tra_LC_P96A | |
| T11 | Per-HC | Tra_LC | |
| T12 | Tra-HC | Per_LC | |
| T13 | Tra-HC | Tra_LC_N30S | WT trastuzumab |
| T14 | Tra-HC | Tra_LC_L54R | |
| T15 | Tra-HC | Tra_LC_S56Y | |
| T16 | Tra-HC | Tra_LC_H91F | |
| T17 | Tra-HC | Tra_LC_H91Y | |
| T18 | Tra-HC | Tra_LC_T94Y | |
| T19 | Tra-HC | Tra_LC_T94W | |
| T20 | Tra-HC | Tra_LC_T94F | |
| T21 | Tra-HC | Tra_LC_P96A | |
| T22 | Tra-HC | Tra_LC | |

*This table uses Kabat numbering

TABLE 4

Mutations of pertuzumab Heavy chains

| mAb# | Heavy chain | Heavy chain mutations* | Light chain | Comment |
|---|---|---|---|---|
| T1 | Per-HC | None | Per_LC | Pertuzumab |
| T24 | Per-HC_v2x | CDR-H2 T30A | Per_LC | |
| T25 | Per-HC_v8x | CDR-H2 G56A | Per_LC | |
| T26 | Per-HC_v16x | CDR-H2 T30A/ CDR-H2 G56A | Per_LC | |

*This table uses Kabat numbering

TABLE 5

Mutations of trastuzumab Heavy chains

| mAb# | Heavy chain mutations* | Light chain | Comment |
|---|---|---|---|
| 122 | None | Tra_LC | Trastuzumab |
| 128 | CDR-H2 N54T | Tra_LC | |
| 129 | CDR-H3 D98T | Tra_LC | |
| 131 | CDR-H3 D98S | Tra_LC | |
| 132 | CDR-H3 D98R | Tra_LC | |

TABLE 5-continued

Mutations of trastuzumab Heavy chains

| mAb# | Heavy chain mutations* | Light chain | Comment |
|---|---|---|---|
| 133 | CDR-H3 D198W | Tra_LC | |
| 134 | CDR-H2 N54T/CDR-H3 D98T | Tra_LC | |
| 135 | CDR-H2 N54T/CDR-H3 D98W | Tra_LC | |

*This table uses Kabat numbering

TABLE 6

Mutations of biparatopic mAb constructs

| mAb # | Heavy chain #1 | Heavy chain(s) | Common light chain |
|---|---|---|---|
| T51 | Bip_mAb_HC11 | $(V_{H\_Pert\_T30A})$-$C_{H1}$-linker-$(V_{H\_Tra\_N54T/D98S})$-$C_{H1}$-Fc | Tra_LC_N30S_S56Y |
| T52 | Bip_mAb_HC12 | $(V_{H\_Pert\_T30A/G56A})$-CH1-linker-$(V_{H\_Tra\_N54T/D98S})$-$C_{H1}$-Fc | Tra_LC_N30S_S56Y |
| T53 | Bip_mAb_HC13 | $(V_{H\_Pert\_T30A})$-$C_{H1}$-Fc-linker-$(V_{H\_Tra\_N54T/D98S}$-$C_{H1})$ | Tra_LC_N30S_S56Y |
| T54 | 1.Bip_mAb_HC14 (Knob) 2. Bip_mAb_HC15 (hole) | 1.$(V_{H-pert\_T30A})$-$C_{H1}$-$(Fc_{(T366W)})$ 2. $(V_{H\_Tra\_N54T/D98S})$-$C_{H1}$-$(Fc_{\_(T366S/L368A/Y407V)})$ | Tra_LC_N30S_S56Y |
| T55 | Bip_mAb_HC11 | $(V_{H\_Pert\_T30A})$-$C_{H1}$-linker-$(V_{H\_Tra\_N54T/D98S})$-$C_{H1}$-Fc | Tra_LC_N30S_S56Y_T94W |
| T56 | Bip_mAb_HC12 | $(V_{H\_Pert\_T30A/G56A})$-CH1-linker-$(V_{H\_Tra\_N54T/D98S})$-$C_{H1}$-Fc | Tra_LC_N30S_S56Y_T94W |
| T57 | Bip_mAb_HC13 | $(V_{H\_Pert\_T30A})$-$C_{H1}$-Fc-linker-$(V_{H-Tra\_N54T/D98S}$-$C_{H1})$ | Tra_LC_N30S_S56Y_T94W |
| T58 | 1.Bip_mAb_HC14 (knob) 2. Bip_mAb_HC15 (hole) | 1.$(V_{H-pert\_T30A})$-$C_{H1}$-(Fc (T366W)) 2. $(V_{H\_Tra\_N55T/D98S})$-$C_{H1}$-$(Fc_{\_(T366S/L368A/Y407V)})$ | Tra_LC_N30S_S56Y_T94W |

*This table uses Kabat numbering except for the substitutions in the Fc region which use Eu numbering Example 1. Binding Potency of Antibodies Comprising the Pertuzumab or Trastuzumab Heavy Chain and a Common Light Chain The binding potency of antibodies to the antigen HER2 was determined using an ELISA assay. The HER2 extracellular domain was coated overnight on 96-well plates by adding 0.2 ug/100 ul/well of HER2 extracellular domain solution. The plates were washed 6 times with PBS, and blocked with 3% BSA and incubated for 2 hours. The plates were again washed 6 times with PBS. Anti-HER2 antibodies were then added to each well at various concentration indicated in the figures. After 1 hour of binding, the plates were washed 6 times with PBS. Horse radish peroxidase (HRP) conjugated secondary antibody was added and incubated for 1 hr. HRP substrate TMB was added to each well and luminescence was read on plate reader. The data were then fitted into 4-parameter sigmoidal curve to generate IC50. Each sample was run in triplicate.

Figure 8A:
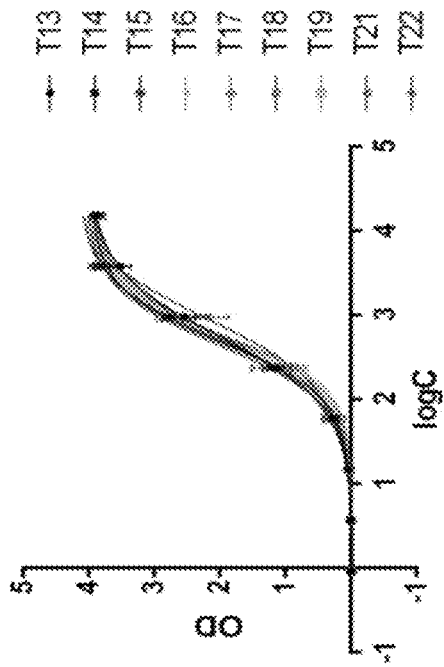
FIG. 8 depicts the effect on binding of mutations in the common light chain when paired with (A) the heavy chain of pertuzumab (mAbs T1 to T11) and (B) that of trastuzumab (mAbs T13 to T22) by ELISA. Panel C depicts the ELISA result for mAb T12 (trastuzumab heavy chain paired with pertuzumab light chain).
Figure 8B:
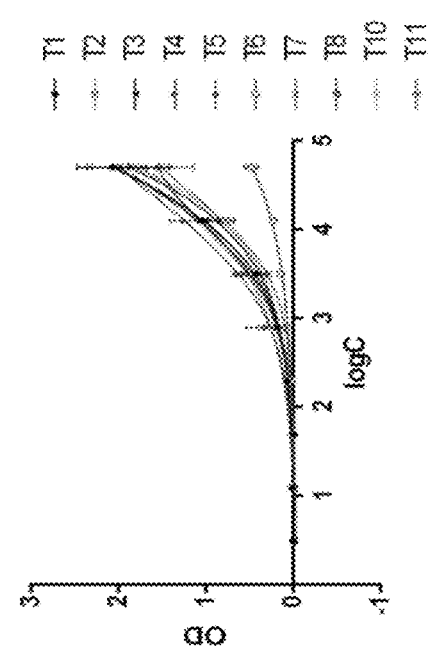
Figure 8C:
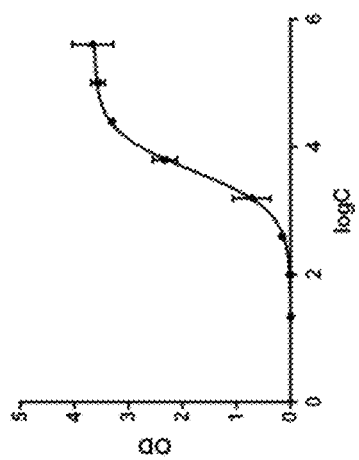

FIG. 8A shows the results from pairing various light chains with the heavy chain of pertuzumab (see Table 3). As can be seen, mAbs formed with all of the common light chains, except T6, performed similarly to pertuzumab (mAb T1), even the wild type trastuzumab light chain (mAbT11). FIGS. 8 B and 8C shows the results from pairing various light chains with the heavy chain of trastuzumab. As can be seen, mAbs formed with all of the common light chains performed similarly to the mAb formed with the wild type light chain from trastuzumab and better than mAb formed with the wild type light chain of pertuzumab (mab T12; FIG. 8B).

Figure 9A:
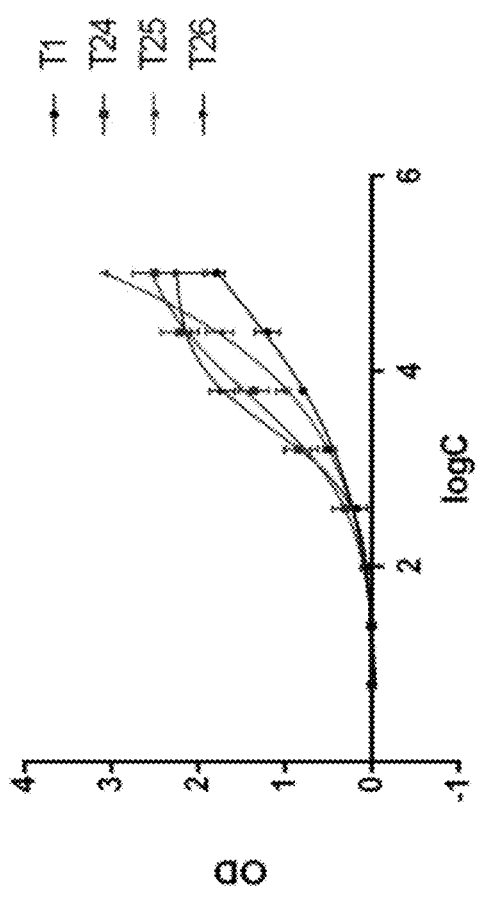
FIG. 9 depicts the effect on binding of the mutated heavy chain of (A) pertuzumab and (B) trastuzumab when paired with wild type light chain by ELISA.
Figure 9B:
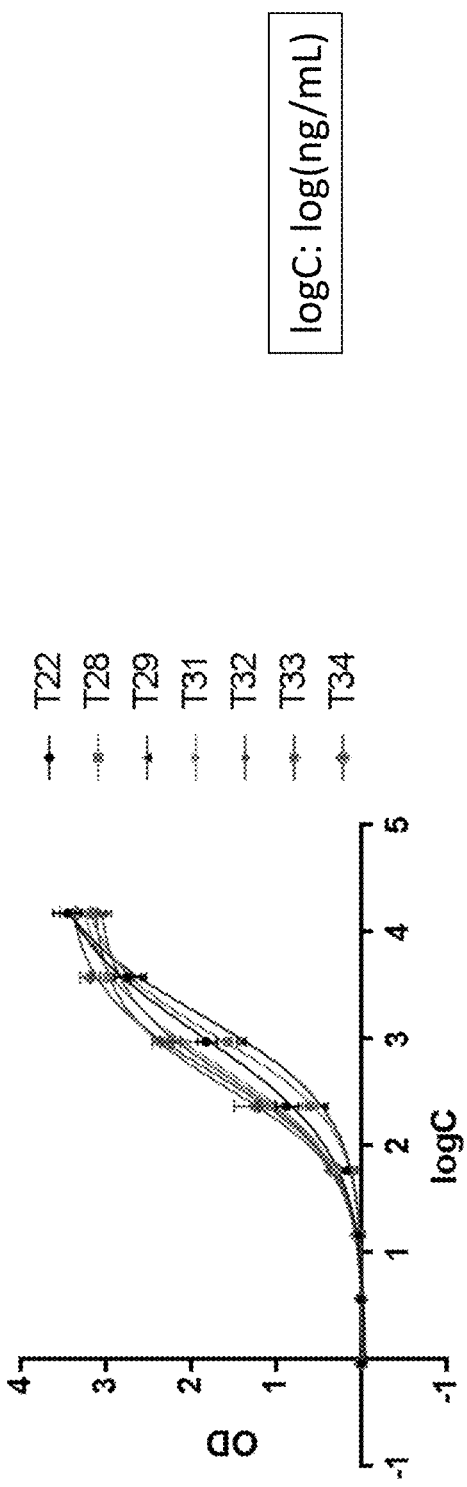

Example 2. Binding Potency of Antibodies Comprising Modified Pertuzumab or Trastuzumab Heavy Chain and Cognate Wild Type Light Chain Using the same ELISA assay described above the binding potency of mAbs formed from modified heavy chains paired with their wild type light chain were determined (see Table 4). As compared to pertuzumab (mAb T1) mAbs formed with all three of the modified pertuzumab heavy chains exhibited improved performance (FIG. 9A). As compared to trastuzumab (mAb T22) mAbs formed with all of the modified trastuzumab heavy chains exhibited generally similar performance, with four of the six showing a modest improvement. (FIG. 9B).

Figure 10A:
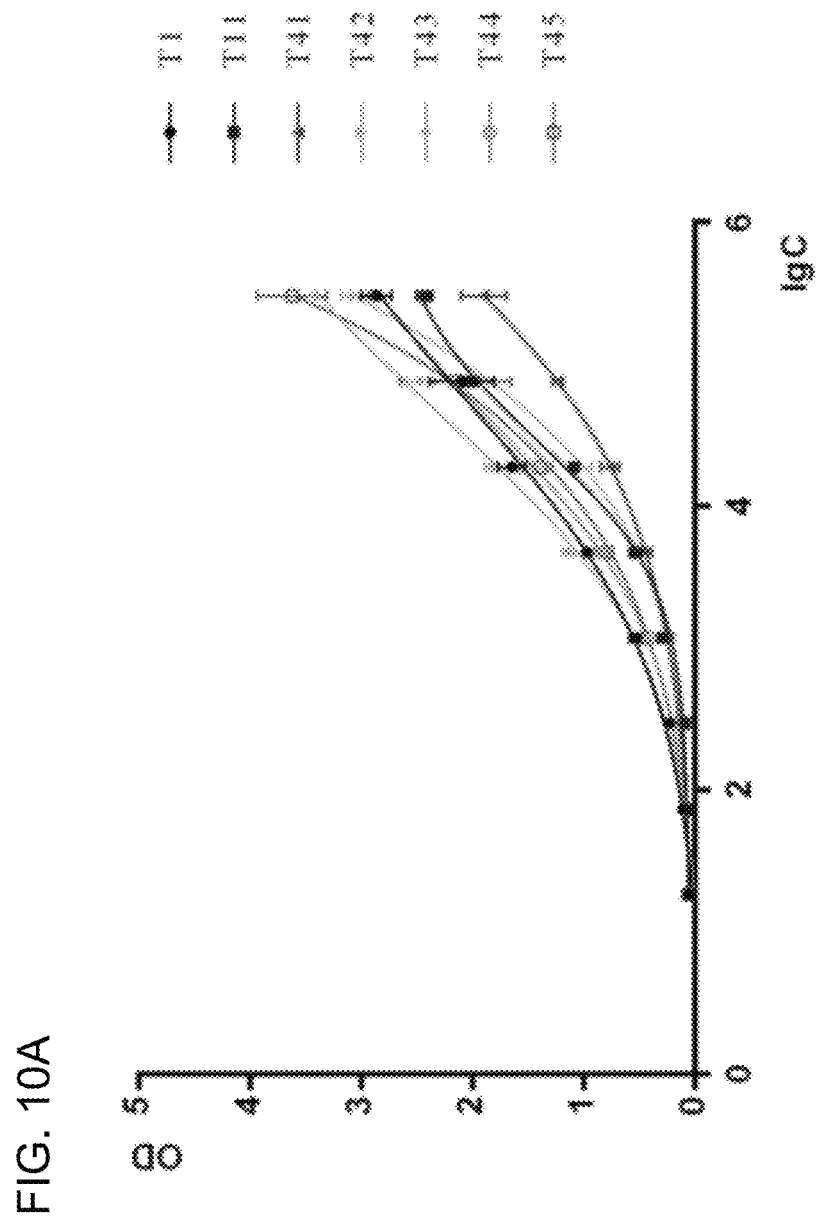
FIG. 10 depicts the effect on binding of the mutated heavy chain of (A) pertuzumab and (B) trastuzumab when paired with common light chains by ELISA.
Figure 10B:
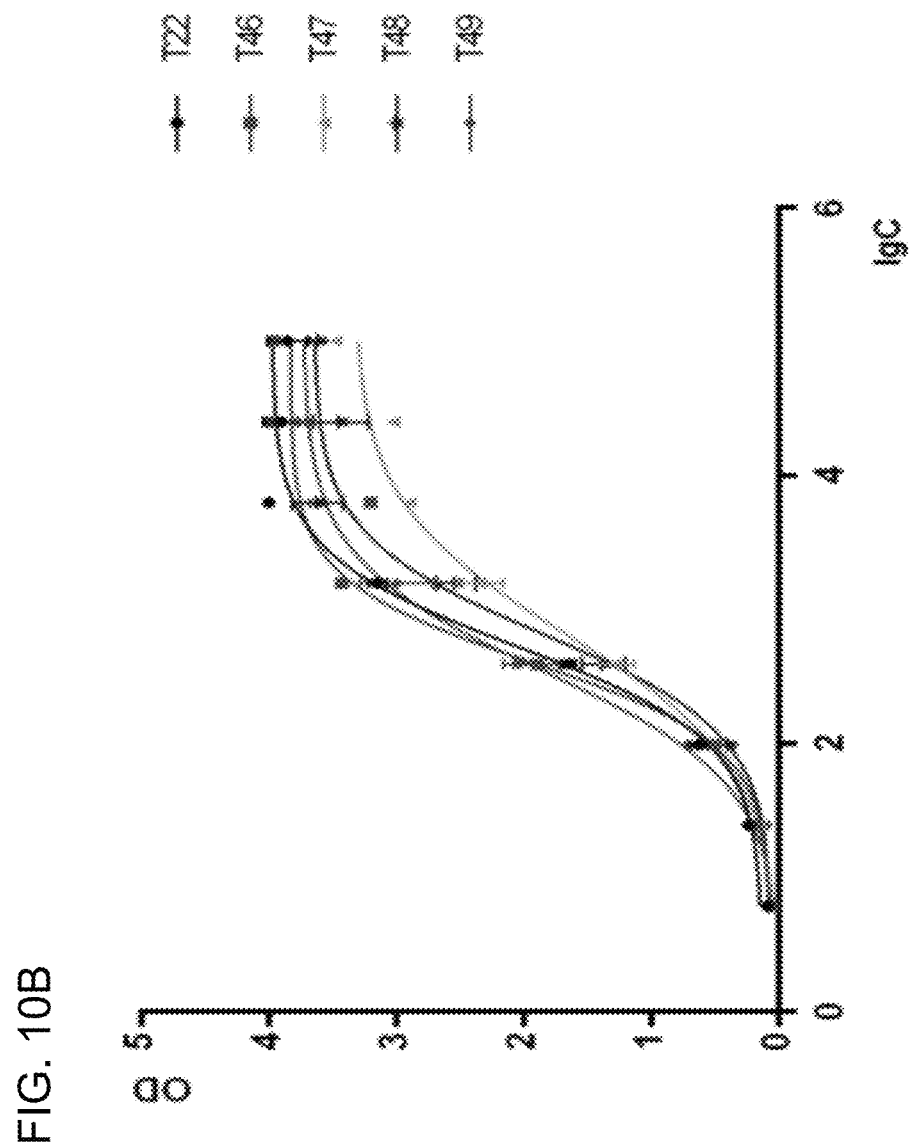

Example 3. Binding Potency of Antibodies Comprising Modified Pertuzumab or Trastuzumab Heavy Chain and Various Common Light Chains Using the same ELISA assay described above the binding potency of mAbs formed from modified heavy chains paired with various common light chains were determined (see Table 5). For mAbs utilizing a modified pertuzumab heavy chain, the best performer in this experiment was mAb T43 containing both the T30A and G56A substitutions in the heavy chain and which was paired with the common light chain containing the N30S, S56Y, and T94W substitutions in the trastuzumab light chain. This light chain performed well in other pairings (consider T44 and T45; FIG. 10A). For mAbs utilizing the modified trastuzumab heavy chain with the N54T and D98T substitutions, performance was generally similar. mAb T47 in which the common light chain lacked the S56Y substitution performed least well, while mAb T46 with the common light chain bearing the N30S, S56Y, and T94W substitutions performed best (FIG. 10B).

Example 4. Expression and Purification of Anti-HER2 Antibody Constructs

Expression constructs were made using standard molecule biology techniques. HEK293E cells were cultured in Freestyle 293 expression medium (ThermoFisher) at 37° C. with 5% $CO_2$. The cells (at $1\times10^6$ cells/ml) were transfected with plasmid DNA (0.5 to 2 ug DNA per $1\times10^6$ cells) of the expression constructs with 2-4 ug/ml PEI. Cells were harvested after the viability dropped to ~70% percent. The antibodies in the medium were purified with protein-A beads (Mabselect Sure (GE Life Tech)) according to manufacturer's instructions. The antibodies were dialyzed in PBS and analyzed on 4% to 10% SDS-PAGE gels (FIG. 11).

Example 5. Binding Potency of Biparatopic Antibody Constructs

Figures 12A, 12B:
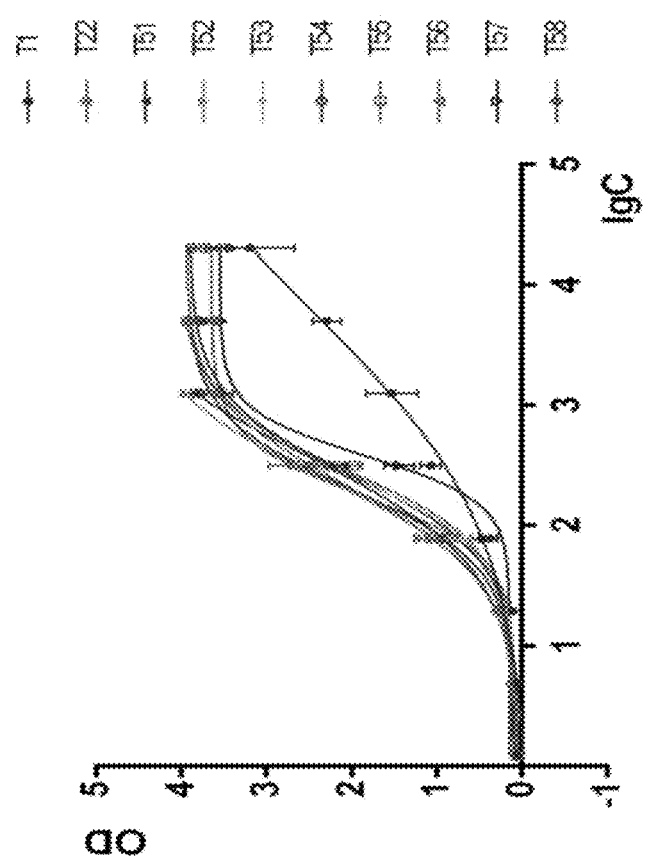

Using the same ELISA assay described above, the binding potency of biparatopic antibody constructs in various formats (see Table 5) was determined. All of the tested constructs performed better than pertuzumab and similarly to trastuzumab in this binding assay, with the exception of biparatopic mAb T57 which performed somewhat less well than the others (FIG. 12A). This assay was not able to distinguish between the heterodimer format antibodies, which are monovalent for the two epitopes and the Fab-Ig and Ig-Fab formats which are bivalent for the two epitopes. The EC50 for the biparatopic antibody constructs ranged from 377 ng/ml for biparatopic mAb T57 to 174 ng/ml or biparatopic mAb T56. By comparison the EC50 for trastuzumab (mAb T22) and pertuzumab (mAb T1) are 211 and 5460 ng/ml, respectively (FIG. 12B).

Example 6. Biparatopic Anti-HER2 mAb Construct Inhibits the Proliferation of Herceptin-Resistant BT474 Breast Cancer Cell Line To determine the potency of antibody in inhibiting the proliferation of BT474 Herceptin-drug resistant cells (BT474-HerDR), cells were plated in 90 μl of medium in 96-well plate at 5000 cells/well in RPMI-1640 medium supplemented with 10% FBS at 37° C. and 5% $CO_2$. 24 hours later, 10 μl of antibody construct diluted to various concentrations with the medium were added to the cell culture. After the cells were cultured for additional 72 hours, cell viability was determined by CellTiterGlo (Promega). The wells without addition of antibody were set as 100% cell viability and Docetaxel was used as a positive control for cytotoxicity. The data were then fitted into 4-parameter sigmoidal curve to generate IC50. The samples were done in triplicate.

Two different biparatopic antibody constructs were tested, biparatopic mAb constructs T51 and T54 (see Table 6) and both exhibited cytotoxicity (a decrease in viability) (FIG. 13, top two panels). By comparison HERCEPTIN® (trastuzumab) had no effect. As trastuzumab works through ADCC its lack of effect in this assay is not surprising, as the other components cellular cytotoxicity are absent. Thus the cytotoxic effect of the biparatopic antibody constructs is surprising and an encouraging predictor of clinical usefulness.

Example 7. Determination of Potency of Antibodies in Inhibiting Proliferation of NCI-N87 (N87) Cells The growth curve of NCI-N87 was initially determined by plating cells at various densities in 96-well tissue culture plates. Cells were gown in RPMI-1640 medium supplemented with 10% fetal bovine serum (FBS). Initial cell density of 1000 cells/well was found to be suitable a it reached confluency after 96 hours of culture and was selected to test the ability of the biparatopic antibody constructs to inhibit growth.

To determine the potency of the biparatopic antibody constructs for inhibiting the proliferation of NCI-N87 cells, the cells were plated in 90 μl of medium in 96-well plate at 1000 cells/well in RPMI-1640 medium supplemented with 10% FBS at 37° C. and 5% $CO_2$. 24 hours later, 10 μl of antibody construct diluted to various concentrations with the medium were added to the cell culture. After the cells were cultured for additional 72 hours, the cell proliferation rates were determined by adding 10 μl of CCK-8 reagent (Sigma). After 3 hour of incubation without light, the plates were read at OD450 nm. The wells without addition of antibody were set as 100% cell viability and Docetaxel was used as a positive control for cytotoxicity. The data were then fitted into 4-parameter sigmoidal curve to generate IC50. The samples were done in triplicate.

Three different biparatopic antibody constructs were tested, biparatopic mAb constructs T51, T52, and T54 (see Table 6) and both inhibited growth (FIG. 14B) and had greater effect than pertuzumab (mAb T1) or trastuzumab (mAb T22) (FIG. 14A). As above, as trastuzumab and pertuzumab work through ADCC their minimal effect in this assay is not surprising, as the other components cellular cytotoxicity are absent. The somewhat greater effect seen with pertuzumab may be related to pertuzumab's ability to inhibit ligand-mediated intracellular signalling. Thus the cytotoxic effect of the biparatopic antibody constructs is surprising and an encouraging predictor of clinical usefulness. Additionally, as noted above Gu's DVD-Ig molecule was seen to have a net agonistic effect in this system. Thus, that these biparatopic antibody constructs inhibit rather than promote growth of this cancer cell line also bodes well for their clinical usefulness.

TABLE 7

| Amino Acid Nomenclature | | |
|---|---|---|
| Name | 3-letter | 1-letter |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 8

Amino Acid Sequences

| SEQ. ID NO. | Description* | Amino Acid Sequence |
|---|---|---|
| 1 | pertuzumab light chain variable region | DIQMTQSPSSLSASVGDRVTITCKASQDVSIG VAWYQQKPGKAPKLLIYSASYRYTGVPSRFSG SGSGTDFTLTISSLQPEDFATYYCQQYYIYPY TFGQGTKVEIK |
| 2 | pertuzumab light chain | DIQMTQSPSSLSASVGDRVTITCKASQDVSIG VAWYQQKPGKAPKLLIYSASYRYTGVPSRFSG SGSGTDFTLTISSLQPEDFATYYCQQYYIYPY TFGQGTKVEIKRTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC |
| 3 | pertuzumab heavy chain variable region | EVQLVESGGGLVQPGGSLRLSCAASGFTFTDY TMDWVRQAPGKGLEWVADVNPNSGGSIYNQRF KGRFTLSVDRSKNTLYLQMNSLRAEDTAVYYC ARNLGPSFYFDYWGQGTLVTVSS |
| 4 | pertuzumab heavy chain | EVQLVESGGGLVQPGGSLRLSCAASGFTFTDY TMDWVRQAPGKGLEWVADVNPNSGGSIYNQRF KGRFTLSVDRSKNTLYLQMNSLRAEDTAVYYC ARNLGPSFYFDYWGQGTLVTVSSASTKGPSVF PLAPSSKSTSGGTAALGCLVKDYFPEPVTVSW NSGALTSGVHTFPAVLQSSGLYSLSSVVTVPS SSLGTQTYICNVNHKPSNTKVDKKVEPKSCDK THTCPPCPAPELLGGPSVFLFPPKPKDTLMIS RTPEVTCVVVDVSHEDPEVKFNWYVDGVEVHN AKTKPREEQYNSTYRVVSVLTVLHQDWLNGKE YKCKVSNKALPAPIEKTISKAKGQPREPQVYT LPPSREEMTKNQVSLTCLVKGFYPSDIAVEWE SNGQPENNYKTTPPVLDSDGSFFLYSKLTVDK SRWQQGNVFSCSVMHEALHNHYTQKSLSLSPG |
| 5 | trastuzumab light chain variable region | DIQMTQSPSSLSASVGDRVTITCRASQDVNTA VAWYQQKPGKAPKLLIYSASFLYSGVPSRFSG SRSGTDFTLTISSLQPEDFATYYCQQHYTTPP TFGQGTKVEIK |
| 6 | trastuzumab light chain | DIQMTQSPSSLSASVGDRVTITCRASQDVNTA VAWYQQKPGKAPKLLIYSASFLYSGVPSRFSG SRSGTDFTLTISSLQPEDFATYYCQQHYTTPP TFGQGTKVEIKRTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC |
| 7 | trastuzumab heavy chain variable region | EVQLVESGGGLVQPGGSLRLSCAASGFNIKDT YIHWVRQAPGKGLEWVARIYPTNGYTRYADSV KGRFTISADTSKNTAYLQMNSLRAEDTAVYYC SRWGGDGFYAMDYWGQGTLVTVSS |
| 8 | trastuzumab heavy chain | EVQLVESGGGLVQPGGSLRLSCAASGFNIKDT YIHWVRQAPGKGLEWVARIYPTNGYTRYADSV KGRFTISADTSKNTAYLQMNSLRAEDTAVYYC SRWGGDGFYAMDYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPPKSC DKTHTCPPCPAPELLGGPSVFLFPPKPKDTLM ISRTPEVTCVVVDVSHEDPEVKFNWYVDGVEV HNAKTKPREEQYNSTYRVVSVLTVLHQDWLNG KEYKCKVSNKALPAPIEKTISKAKGQPREPQV YTLPPSRDELTKNQVSLTCLVKGFYPSDIAVE WESNGQPENNYKTTPPVLDSDGSFFLYSKLTV DKSRWQQGNVFSCSVMHEALHNHYTQKSLSLS PGK |
| 9 | ramucirumab light chain variable region | DIQMTQSPSSVSASIGDRVTITCRASQGIDNW LGWYQQKPGKAPKLLIYDASNLDTGVPSRFSG SGSGTYFTLTISSLQAEDFAVYFCQQAKAFPP TFGGGTKVDIK |
| 10 | ramucirumab light chain | DIQMTQSPSSVSASIGDRVTITCRASQGIDNW LGWYQQKPGKAPKLLIYDASNLDTGVPSRFSG SGSGTYFTLTISSLQAEDFAVYFCQQAKAFPP |

TABLE 8-continued

Amino Acid Sequences

| SEQ. ID NO. | Description* | Amino Acid Sequence |
|---|---|---|
|  |  | TFGGGTKVDIKGTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC |
| 11 | ramucirumab heavy chain variable region | EVQLVQSGGGLVKPGGSLRLSCAASGFTFSSY SMNWVRQAPGKGLEWVSSISSSSSYIYYADSV KGRFTISRDNAKNSLYLQMNSLRAEDTAVYYC ARVTDAFDIWGQGTMVTVSS |
| 12 | ramucirumab heavy chain | EVQLVQSGGGLVKPGGSLRLSCAASGFTFSSY SMNWVRQAPGKGLEWVSSISSSSSYIYYADSV KGRFTISRDNAKNSLYLQMNSLRAEDTAVYYC ARVTDAFDIWGQGTMVTVSSASTKGPSVFPLA PSSKSTSGGTAALGCLVKDYFPEPVTVSWNSG ALTSGVHTFPAVLQSSGLYSLSSVVTVPSSSL GTQTYICNVNHKPSNTKVDKKVEPKSCDKTHT CPPCPAPELLGGPSVFLFPPKPKDTLMISRTP EVTCVVVDVSHEDPEVKFNWYVDGVEVHNAKT KPREEQYNSTYRVVSVLTVLHQDWLNGKEYKC KVSNKALPAPIEKTISKAKGQPREPQVYTLPP SREEMTKNQVSLTCLVKGFYPSDIAVEWESNG QPENNYKTTPPVLDSDGSFFLYSKLTVDKSRW QQGNVFSCSVMHEALHNHYTQKSLSLSPGK |
| 13 | Biparatopic antibody construct HC11 (including signal sequence); pertuzumab heavy chain V-region T30A, followed by trastuzumab V-region N54T and D98S, with Fc M428L (substitutions in bold and underlined); Fab-Ig format | MNFGLSLIFLVLILKGVQCEVQLVESGGGLVQ PGGSLRLSCAASGFTFADYTMDWVRQAPGKGL EWVADVNPNSGGSIYNQRFKGRFTLSVDRSKN TLYLQMNSLRAEDTAVYYCARNLGPSFYFDYW GQGTLVTVSSASTKGPSVFPLAPSSKSTSGGT AALGCLVKDYFPEPVTVSWNSGALTSGVHTFP AVLQSSGLYSLSSVVTVPSSSLGTQTYICNVN HKPSNTKVDKKVEPKSCDKGGGSGGGSGGGSG GGEVQLVESGGGLVQPGGSLRLSCAASGFNIK DTYIHWVRQAPGKGLEWVARIYPTTGYTRYAD SVKGRFTISADTSKNTAYLQMNSLRAEDTAVY YCSRWGGSGFYAMDYWGQGTLVTVSSASTKGP SVFPLAPSSKSTSGGTAALGCLVKDYFPEPVT VSWNSGALTSGVHTFPAVLQSSGLYSLSSVVT VPSSSLGTQTYICNVNHKPSNTKVDKKVEPKS CDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWLN GKEYKCKVSNKALPAPIEKTISKAKGQPREPQ VYTLPPSRDELTKNQVSLTCLVKGFYPSDIAV EWESNGQPENNYKTTPPVLDSDGSFFLYSKLT VDKSRWQQGNVFSCSVLHEALHNHYTQKSLSL SPGK |
| 15 | Biparatopic antibody construct HC12 (including signal sequence); pertuzumab heavy chain V-region T30A/G56A, followed by trastuzumab V-region N54T and D98S, with Fc M428L (substitutions in bold and underlined); Fab-Ig format | MNFGLSLIFLVLILKGVQCEVQLVESGGGLVQ PGGSLRLSCAASGFTFADYTMDWVRQAPGKGL EWVADVNPNSGASIYNQRFKGRFTLSVDRSKN TLYLQMNSLRAEDTAVYYCARNLGPSFYFDYW GQGTLVTVSSASTKGPSVFPLAPSSKSTSGGT AALGCLVKDYFPEPVTVSWNSGALTSGVHTFP AVLQSSGLYSLSSVVTVPSSSLGTQTYICNVN HKPSNTKVDKKVEPKSCDKGGGSGGGSGGGSG GGEVQLVESGGGLVQPGGSLRLSCAASGFNIK DTYIHWVRQAPGKGLEWVARIYPTTGYTRYAD SVKGRFTISADTSKNTAYLQMNSLRAEDTAVY YCSRWGGSGFYAMDYWGQGTLVTVSSASTKGP SVFPLAPSSKSTSGGTAALGCLVKDYFPEPVT VSWNSGALTSGVHTFPAVLQSSGLYSLSSVVT VPSSSLGTQTYICNVNHKPSNTKVDKKVEPKS CDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWLN GKEYKCKVSNKALPAPIEKTISKAKGQPREPQ VYTLPPSRDELTKNQVSLTCLVKGFYPSDIAV EWESNGQPENNYKTTPPVLDSDGSFFLYSKLT VDKSRWQQGNVFSCSVLHEALHNHYTQKSLSL SPGK |
| 17 | Biparatopic antibody construct HC13 | MNFGLSLIFLVLILKGVQCEVQLVESGGGLVQ PGGSLRLSCAASGFTFADYTMDWVRQAPGKGL |

TABLE 8-continued

Amino Acid Sequences

| SEQ. ID NO. | Description* | Amino Acid Sequence |
|---|---|---|
|  | (including signal sequence); pertuzumab heavy T30A, with Fc M428L, followed by trastuzumab V-region N54T and D98S (substitutions in bold and underlined); Ig-Fab format | EWVADVNPNSGGSIYNQRFKGRFTLSVDRSKN TLYLQMNSLRAEDTAVYYCARNLGPSFYFDYW GQGTLVTVSSASTKGPSVFPLAPSSKSTSGGT AALGCLVKDYFPEPVTVSWNSGALTSGVHTFP AVLQSSGLYSLSSVVTVPSSSLGTQTYICNVN HKPSNTKVDKKVEPKSCDKTHTCPPCPAPELL GGPSVFLFPPKPKDTLMISRTPEVICVVVDVS HEDPEVKFNWYVDGVEVHNAKTKPREEQYNST YRVVSVLTVLHQDWLNGKEYKCKVSNKALPAP IEKTISKAKGQPREPQVYTLPPSRDELTKNQV SLTCLVKGFYPSDIAVEWESNGQPENNYKTTP PVLDSDGSFFLYSKLTVDKSRWQQGNVFSCSV LHEALHNHYTQKSLSLSPGGGGSGGGSGGGSG GGEVQLVESGGGLVQPGGSLRLSCAASGFNIK DTYIHWVRQAPGKGLEWVARIYPTTGYTRYAD SVKGRFTISADTSKNTAYLQMNSLRAEDTAVY YCSRWGGSGFYAMDYWGQGTLVTVSSASTKGP SVFPLAPSSKSTSGGTAALGCLVKDYFPEPVT VSWNSGALTSGVHTFPAVLQSSGLYSLSSVVT VPSSSLGTQTYICNVNHKPSNTKVDKKVEPKS C |
| 19 | Biparatopic antibody construct HC14 (including signal sequence); pertuzumab heavy V-region T30A, with Fc "knob" for heterodimer format T366W and Fc M428L | MNFGLSLIFLVLILKGVQCEVQLVESGGGLVQ PGGSLRLSCAASGFTFADYTMDWVRQAPGKGL EWVADVNPNSGGSIYNQRFKGRFTLSVDRSKN TLYLQMNSLRAEDTAVYYCARNLGPSFYFDYW GQGTLVTVSSASTKGPSVFPLAPSSKSTSGGT AALGCLVKDYFPEPVTVSWNSGALTSGVHTFP AVLQSSGLYSLSSVVTVPSSSLGTQTYICNVN HKPSNTKVDKKVEPKSCDKTHTCPPCPAPELL GGPSVFLFPPKPKDTLMISRTPEVICVVVDVS HEDPEVKFNWYVDGVEVHNAKTKPREEQYNST YRVVSVLTVLHQDWLNGKEYKCKVSNKALPAP IEKTISKAKGQPREPQVYTLPPSRDELTKNQV SLWCLVKGFYPSDIAVEWESNGQPENNYKTTP PVLDSDGSFFLYSKLTVDKSRWQQGNVFSCSV LHEALHNHYTQKSLSLSPGK |
| 21 | Biparatopic antibody construct HC15 (including signal sequence); trastuzumab V-region N54T and D98S, with Fc "hole" for heterodimer format T366S/L368A/Y407V and Fc M428L | MNFGLSLIFLVLILKGVQCEVQLVESGGGLVQ PGGSLRLSCAASGFNIKDTYIHWVRQAPGKGL EWVARIYPTTGYTRYADSVKGRFTISADTSKN TAYLQMNSLRAEDTAVYYCSRWGGSGFYAMDY WGQGTLVTVSSASTKGPSVFPLAPSSKSTSGG TAALGCLVKDYFPEPVTVSWNSGALTSGVHTF PAVLQSSGLYSLSSVVTVPSSSLGTQTYICNV NHKPSNTKVDKKVEPKSCDKTHTCPPCPAPEL LGGPSVFLFPPKPKDTLMISRTPEVICVVVDV SHEDPEVKFNWYVDGVEVHNAKTKPREEQYNS TYRVVSVLTVLHQDWLNGKEYKCKVSNKALPA PIEKTISKAKGQPREPQVYTLPPSRDELTKNQ VSLSCAVKGFYPSDIAVEWESNGQPENNYKTT PPVLDSDGSFFLVSKLTVDKSRWQQGNVFSCS VLHEALHNHYTQKSLSLSPGK |
| 23 | Linker | GGGSGGGSGGGSGGG |
| 24 | Signal sequence | MNFGLSLIFLVLILKGVQC |
| 29 | Pert_$V_{H\_V16x}C_{H1}Fc_{ML}$ | MNFGLSLIFLVLILKGVQCEVQLVESGGGLVQ PGGSLRLSCAASGFTFTDYTMDWVRQAPGKGL EWVADVNPNSGGSIYNQRFKGRFTLSVDRSKN TLYLQMNSLRAEDTAVYYCARNLGPSFYFDYW GQGTLVTVSSASTKGPSVFPLAPSSKSTSGGT AALGCLVKDYFPEPVTVSWNSGALTSGVHTFP AVLQSSGLYSLSSVVTVPSSSLGTQTYICNVN HKPSNTKVDKKVEPKSCDK |
| 30 | Tra_$V_{H\-VNT\_DS}C_{H1}$ | EVQLVESGGGLVQPGGSLRLSCAASGFNIKDT YIHWVRQAPGKGLEWVARIYPTTGYTRYADSV KGRFTISADTSKNTAYLQMNSLRAEDTAVYYC SRWGGSGFYAMDYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPELLGGPSVFLFPPKPKDTLMI |

TABLE 8-continued

Amino Acid Sequences

| SEQ. ID NO. | Description* | Amino Acid Sequence |
|---|---|---|
|  |  | SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSREEMTKNQVSLTCLVKGFYPSDIAVEW ESNGQPENNYKTTPPVLDSDGSFFLYSKLTVD KSRWQQGNVFSCSVLHEALHNHYTQKSLSLSP GK |
| 31 | Pert_V$_{H\_V16x}$C$_{H1}$Fc$_{ML}$-linker-Tra_V$_{H-VNT\_DS}$C$_{H1}$ | MNFGLSLIFLVLILKGVQCEVQLVESGGGLVQ PGGSLRLSCAASGFTFTDYTMDWVRQAPGKGL EWVADVNPNSGGSIYNQRFKGRFTLSVDRSKN TLYLQMNSLRAEDTAVYYCARNLGPSFYFDYW GQGTLVTVSSASTKGPSVFPLAPSSKSTSGGT AALGCLVKDYFPEPVTVSWNSGALTSGVHTFP AVLQSSGLYSLSSVVTVPSSSLGTQTYICNVN HKPSNTKVDKKVEPKSCDKGGGSGGGSGGGSG GGEVQLVESGGGLVQPGGSLRLSCAASGFNIK DTYIHWVRQAPGKGLEWVARIYPTTGYTRYAD SVKGRFTISADTSKNTAYLQMNSLRAEDTAVY YCSRWGGSGFYAMDYWGQGTLVTVSSASTKGP SVFPLAPSSKSTSGGTAALGCLVKDYFPEPVT VSWNSGALTSGVHTFPAVLQSSGLYSLSSVVT VPSSSLGTQTYICNVNHKPSNTKVDKKVEPKS CDKTHTCPPCPAPELLGGPSVFLFPPKPKDTL MISRTPEVICVVVDVSHEDPEVKFNWYVDGVE VHNAKTKPREEQYNSTYRVVSVLTVLHQDWLN GKEYKCKVSNKALPAPIEKTISKAKGQPREPQ VYTLPPSREEMTKNQVSLTCLVKGFYPSDIAV EWESNGQPENNYKTIPPVLDSDGSFFLYSKLT VDKSRWQQGNVFSCSVLHEALHNHYTQKSLSL SPGK |
| 32 | Pert_Fab + Fc | MNFGLSLIFLVLILKGVQCEVQLVESGGGLVQ PGGSLRLSCAASGFTFTDYTMDWVRQAPGKGL EWVADVNPNSGGSIYNQRFKGRFTLSVDRSKN TLYLQMNSLRAEDTAVYYCARNLGPSFYFDYW GQGTLVTVSSASTKGPSVFPLAPSSKSTSGGT AALGCLVKDYFPEPVTVSWNSGALTSGVHTFP AVLQSSGLYSLSSVVTVPSSSLGTQTYICNVN HKPSNTKVDKKVEPKSCDKTHTCPPCPAPELL GGPSVFLFPPKPKDTLMISRTPEVTCVVVDVS HEDPEVKFNWYVDGVEVHNAKTKPREEQYNST YRVVSVLTVLHQDWLNGKEYKCKVSNKALPAP IEKTISKAKGQPREPQVYTLPPSREEMTKNQV SLTCLVKGFYPSDIAVEWESNGQPENNYKTTP PVLDSDGSFFLYSKLTVDKSRWQQGNVFSCSV LHEALHNHYTQKSLSLSPG |
| 33 | Tras_Fab | EVQLVESGGGLVQPGGSLRLSCAASGFNIKDT YIHWVRQAPGKGLEWVARIYPTTGYTRYADSV KGRFTISADTSKNTAYLQMNSLRAEDTAVYYC SRWGGSGFYAMDYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSC |
| 34 | Pert_HC_v2x-Tra_HC_vNT_DS_ML | MNFGLSLIFLVLILKGVQCEVQLVESGGGLVQ PGGSLRLSCAASGFTFTDYTMDWVRQAPGKGL EWVADVNPNSGGSIYNCTRFKGRFTLSVDRSK NTLYLQMNSLRAEDTAVYYCARNLGPSFYFDY WGQGTLVTVSSASTKGPSVFPLAPSSKSTSGG TAALGCLVKDYFPEPVTVSWNSGALTSGVHTF PAVLQSSGLYSLSSVVTVPSSSLGTQTYICNV NHKPSNTKVDKKVEPKSCDKTHTCPPCPAPEL LGGPSVFLFPPKPKDTLMISRTPEVTCVVVDV SHEDPEVKFNWYVDGVEVHNAKTKPREEQYNS TYRVVSVLTVLHQDWLNGKEYKCKVSNKALPA PIEKTISKAKGQPREPQVYTLPPSREEMTKNQ VSLTCLVKGFYPSDIAVEWESNGQPENNYKTT PPVLDSDGSFFLYSKLTVDKSRWQQGNVFSCS VLHEALHNHYTQKSLSLSPGGGGSGGGSGGGS GGEVQLVESGGGLVQPGGSLRLSCAASGFNI KDTYIHWVRQAPGKGLEWVARIYPTTGYTRYA DSVKGRFTISADTSKNTAYLQMNSLRAEDTAV YYCSRWGGSGFYAMDYWGQGTLVTVSSASTKG |

TABLE 8-continued

Amino Acid Sequences

| SEQ. ID NO. | Description* | Amino Acid Sequence |
|---|---|---|
| | | PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SC |
| 35 | Pert_HC_v16x Knob | MNFGLSLIFLVLILKGVQCEVQLVESGGGLVQ PGGSLRLSCAASGFTFTDYTMDWVRQAPGKGL EWVADVNPNSGGSIYNQRFKGRFTLSVDRSKN TLYLQMNSLRAEDTAVYYCARNLGPSFYFDYW GQGTLVTVSSASTKGPSVFPLAPSSKSTSGGT AALGCLVKDYFPEPVTVSWNSGALTSGVHTFP AVLQSSGLYSLSSVVTVPSSSLGTQTYICNVN HKPSNTKVDKKVEPKSCDKTHTCPPCPAPELL GGPSVFLFPPKPKDTLMISRTPEVTCVVVDVS HEDPEVKFNWYVDGVEVHNAKTKPREEQYNST YRVVSVLTVLHQDWLNGKEYKCKVSNKALPAP IEKTISKAKGQPREPQVYTLPPSREEMTKNQV SLWCLVKGFYPSDIAVEWESNGQPENNYKTTP PVLDSDGSFFLYSKLTVDKSRWQQGNVFSCSV LHEALHNHYTQKSLSLSPGK |
| 36 | Tras_HC_hole | EVQLVESGGGLVQPGGSLRLSCAASGFNIKDT YIHWVRQAPGKGLEWVARIYPTTGYTRYADSV KGRFTISADTSKNTAYLQMNSLRAEDTAVYYC SRWGGSGFYAMDYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPELLGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSREEMTKNQVSLSCAVKGFYPSDIAVEW ESNGQPENNYKTTPPVLDSDGSFFLVSKLTVD KSRWQQGNVFSCSVLHEALHNHYTQKALSLSP GK |
| 37 | gTra_HC_vNT_DT_ML | EVQLVESGGGLVQPGGSLRLSCAASGFNIKDT YIHWVRQAPGKGLEWVARIYPTTGYTRYADSV KGRFTISADTSKNTAYLQMNSLRAEDTAVYYC SRWGGTGFYAMDYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPELLGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSREEMTKNQVSLTCLVKGFYPSDIAVEW ESNGQPENNYKTTPPVLDSDGSFFLYSKLTVD KSRWQQGNVFSCSVLHEALHNHYTQKSLSLSP GK |

*V-region substitutions indicated with Kabat numbering; Fc region substitutions indicated with Eu numbering.

TABLE 9

Nucleic Acid Sequences

| SEQ ID NO. | Description | Nucleic Acid Sequence |
|---|---|---|
| 25 | Linker | GGCGGAGGGAGCGGCGGAGGCTCCGGAGGCG GCAGCGGAGGCGGA |
| 26 | EcoRI/Kozak sequence (before ATG) | GAATTCGCCACC |
| 27 | BamHI cloning site (following stop codon) | AGGATCC |
| 28 | Signal sequence | ATGAACTTTGGCCTGAGCCTGATTTTTCTCGTCC TGATCCTGAAGGGCGTGCAGTGT |

TABLE 9-continued

Nucleic Acid Sequences

| SEQ ID NO. | Description | Nucleic Acid Sequence |
|---|---|---|
| 14 | Biparatopic antibody construct HC11 (including 5' cloning site (ECoRI) and Kozak sequence, signal sequence, and 3' cloning site (BamHI)) | GAATTCGCCACCATGAACTTTGGCCTGAGCCTG<br>ATTTTTCTCGTCCTGATCCTGAAGGGCGTGCAG<br>TGTGAGGTGCAGCTGGTGGAGAGCGGCGGCG<br>GCCTGGTGCAGCCCGGCGGCAGCCTGCGCCTG<br>TCCTGCGCCGCCAGCGGCTTCACCTTTGCCGA<br>CTACACCATGGACTGGGTGCGCCAGGCTCCCG<br>GCAAGGGCCTGGAGTGGGTGGCCGACGTGAAC<br>CCCAACAGCGGCGGCAGCATCTACAACCAGCG<br>CTTCAAGGGCCGCTTCACCCTGAGCGTGGACC<br>GCAGCAAGAACACCCTGTACCTGCAGATGAACA<br>GCCTGCGCGCCGAGGACACCGCCGTGTACTAC<br>TGCGCCCGCAACCTGGGCCCCAGCTTCTACTTC<br>GACTATTGGGGCAGGGCACCCTGGTCACCGT<br>GAGCAGCGCTAGCACCAAGGGCCCATCCGTCT<br>TCCCCCTGGCACCCTCCTCCAAGAGCACCTCTG<br>GGGGCACAGCTGCCCTGGGCTGCCTGGTCAAG<br>GACTACTTCCCCGAACCAGTGACCGTGTCCTGG<br>AACTCAGGCGCCCTGACCAGCGGCGTGCACAC<br>CTTCCCTGCTGTCCTGCAGTCCTCAGGACTCTA<br>CTCCCTCAGCAGCGTGGTGACTGTGCCCTCTAG<br>CAGCTTGGGCACCCAGACCTACATCTGCAACGT<br>GAATCACAAGCCCAGCAACACCAAGGTGGACAA<br>GAAAGTTGAGCCCAAATCTTGTGACAAAGGCGG<br>AGGGAGCGGCGGAGGCTCCGGAGGCGGCAGC<br>GGAGGCGGAGAGGTGCAGCTGGTGGAGTCTGG<br>AGGAGGGCTGGTGCAGCCAGGAGGGTCCCTGA<br>GACTGTCTTGCGCCGCTAGTGGCTTCAACATCA<br>AGGACACCTACATCCACTGGGTGAGACAGGCC<br>CCCGGAAAAGGCCTGGAGTGGGTGGCCAGGAT<br>CTACCCTACCACCGGCTACACCAGGTACGCCGA<br>CAGCGTGAAGGGCAGGTTCACCATCAGCGCCG<br>ACACCAGCAAGAACACCGCCTACCTGCAGATGA<br>ACAGCCTGAGGGCCGAGGACACCGCCGTGTAC<br>TACTGCAGCAGATGGGGCGGCAGCGGCTTCTA<br>CGCCATGGACTACTGGGGACAGGGCACACTGG<br>TCACTGTGTCTAGTGCCTCAACAAAGGGGCCTA<br>GCGTGTTTCCACTGGCTCCCTCAAGCAAAAGCA<br>CTTCCGGAGGCACCGCTGCACTGGGATGTCTG<br>GTGAAGGACTACTTCCCAGAGCCCGTCACCGTG<br>TCTTGGAACAGTGGGGCTCTGACCAGCGGAGT<br>CCACACATTTCCTGCAGTGCTGCAGTCCTCTGG<br>CCTGTACAGCCTGAGTTCAGTGGTCACAGTCCC<br>AAGCTCCTCTCTGGGGACCCAGACATATATCTG<br>CAACGTGAATCACAAGCCAAGCAATACTAAAGT<br>CGACAAGAAAGTGGAGCCCAAGAGCTGTGATAA<br>AACTCATACCTGCCCCCCTTGTCCTGCACCAGA<br>ACTGCTGGGAGGACCATCCGTGTTCCTGTTTCC<br>ACCCAAGCCTAAAGACACCCTGATGATTTCCCG<br>CACACCCGAGGTCACTTGCGTGGTCGTGGACG<br>TGTCTCACGAGGACCCCGAAGTCAAGTTCAACT<br>GGTACGTGGATGGCGTCGAAGTGCATAATGCTA<br>AGACCAAACCAAGGGAGGAACAGTACAACTCCA<br>CATATCGCGTCGTGTCTGTCCTGACTGTGCTGC<br>ACCAGGATTGGCTGAACGGCAAAGAGTATAAGT<br>GCAAAGTGAGCAATAAGGCCCTGCCCGCTCCTA<br>TCGAGAAAACTATTAGCAAGGCTAAAGGGCAGC<br>CTCGCGAACCACAGGTGTACACCCTGCCTCCAT<br>CTCGGGACGAACTGACTAAGAACCAAGTCAGTC<br>TGACCTGTCTGGTGAAAGGGTTCTATCCTAGCG<br>ACATTGCAGTGGAGTGGGAATCCAATGGACAGC<br>CAGAGAACAATTACAAGACCACACCCCCTGTGC<br>TGGACTCAGATGGAAGCTTCTTTCTGTATAGTAA<br>GCTGACCGTGGATAAATCACGCTGGCAGCAGG<br>GCAACGTCTTTTCTTGTAGTGTGCTGCATGAAG<br>CCCTGCACAATCATTACACACAGAAGTCACTGA<br>GCCTGTCCCCTGGCAAATGAAGGATCC |
| 16 | Biparatopic antibody construct HC12 (including 5' cloning site (ECoRI) and Kozak sequence, signal sequence, and 3' cloning site (BamHI)) | GAATTCGCCACCATGAACTTTGGCCTGAGCCTG<br>ATTTTTCTCGTCCTGATCCTGAAGGGCGTGCAG<br>TGTGAGGTGCAGCTGGTGGAGAGCGGCGGCG<br>GCCTGGTGCAGCCCGGCGGCAGCCTGCGCCTG<br>TCCTGCGCCGCCAGCGGCTTCACCTTTGCCGA<br>CTACACCATGGACTGGGTGCGCCAGGCTCCCG<br>GCAAGGGCCTGGAGTGGGTGGCCGACGTGAAC |

TABLE 9-continued

Nucleic Acid Sequences

| SEQ ID NO. | Description | Nucleic Acid Sequence |
|---|---|---|
| | | CCCAACAGCGGCGCCAGCATCTACAACCAGCG |
| | | CTTCAAGGGCCGCTTCACCCTGAGCGTGGACC |
| | | GCAGCAAGAACACCCTGTACCTGCAGATGAACA |
| | | GCCTGCGCGCCGAGGACACCGCCGTGTACTAC |
| | | TGCGCCCGCAACCTGGGCCCCAGCTTCTACTTC |
| | | GACTATTGGGGCAGGGCACCCTGGTCACCGT |
| | | GAGCAGCGCTAGCACCAAGGGCCCATCCGTCT |
| | | TCCCCCTGGCACCCTCCTCCAAGAGCACCTCTG |
| | | GGGGCACAGCTGCCCTGGGCTGCCTGGTCAAG |
| | | GACTACTTCCCCGAACCAGTGACCGTGTCCTGG |
| | | AACTCAGGCGCCCTGACCAGCGGCGTGCACAC |
| | | CTTCCCTGCTGTCCTGCAGTCCTCAGGACTCTA |
| | | CTCCCTCAGCAGCGTGGTGACTGTGCCCTCTAG |
| | | CAGCTTGGGCACCCAGACCTACATCTGCAACGT |
| | | GAATCACAAGCCCAGCAACACCAAGGTGGACAA |
| | | GAAAGTTGAGCCCAAATCTTGTGACAAAGGCGG |
| | | AGGGAGCGGCGGAGGCTCCGGAGGCGGCAGC |
| | | GGAGGCGGAGAGGTGCAGCTGGTGGAGTCTGG |
| | | AGGAGGGCTGGTGCAGCCAGGAGGGTCCCTGA |
| | | GACTGTCTTGCGCCGCTAGTGGCTTCAACATCA |
| | | AGGACACCTACATCCACTGGGTGAGACAGGCC |
| | | CCCGGAAAAGGCCTGGAGTGGGTGGCCAGGAT |
| | | CTACCCTACCACCGGCTACACCAGGTACGCCGA |
| | | CAGCGTGAAGGGCAGGTTCACCATCAGCGCCG |
| | | ACACCAGCAAGAACACCGCCTACCTGCAGATGA |
| | | ACAGCCTGAGGGCCGAGGACACCGCCGTGTAC |
| | | TACTGCAGCAGATGGGGCGGCAGCGGCTTCTA |
| | | CGCCATGGACTACTGGGGACAGGGCACACTGG |
| | | TCACTGTGTCTAGTGCCTCAACAAAGGGGCCTA |
| | | GCGTGTTTCCACTGGCTCCCTCAAGCAAAAGCA |
| | | CTTCCGGAGGCACCGCTGCACTGGGATGTCTG |
| | | GTGAAGGACTACTTCCCAGAGCCCGTCACCGTG |
| | | TCTTGGAACAGTGGGGCTCTGACCAGCGGAGT |
| | | CCACACATTTCCTGCAGTGCTGCAGTCCTCTGG |
| | | CCTGTACAGCCTGAGTTCAGTGGTCACAGTCCC |
| | | AAGCTCCTCTCTGGGGACCCAGACATATATCTG |
| | | CAACGTGAATCACAAGCCAAGCAATACTAAAGT |
| | | CGACAAGAAAGTGGAGCCCAAGAGCTGTGATAA |
| | | AACTCATACCTGCCCCCCTTGTCCTGCACCAGA |
| | | ACTGCTGGGAGGACCATCCGTGTTCCTGTTTCC |
| | | ACCCAAGCCTAAAGACACCCTGATGATTTCCCG |
| | | CACACCCGAGGTCACTTGCGTGGTCGTGGACG |
| | | TGTCTCACGAGGACCCCGAAGTCAAGTTCAACT |
| | | GGTACGTGGATGGCGTCGAAGTGCATAATGCTA |
| | | AGACCAAACCAAGGGAGGAACAGTACAACTCCA |
| | | CATATCGCGTCGTGTCTGTCCTGACTGTGCTGC |
| | | ACCAGGATTGGCTGAACGGCAAGAGTATAAGT |
| | | GCAAAGTGAGCAATAAGGCCCTGCCCGCTCCTA |
| | | TCGAGAAAACTATTAGCAAGGCTAAAGGGCAGC |
| | | CTCGCGAACCACAGGTGTACACCCTGCCTCCAT |
| | | CTCGGGACGAACTGACTAAGAACCAAGTCAGTC |
| | | TGACCTGTCTGGTGAAAGGGTTCTATCCTAGCG |
| | | ACATTGCAGTGGAGTGGGAATCCAATGGACAGC |
| | | CAGAGAACAATTACAAGACCACACCCCCTGTGC |
| | | TGGACTCAGATGGAAGCTTCTTTCTGTATAGTAA |
| | | GCTGACCGTGGATAAATCACGCTGGCAGCAGG |
| | | GCAACGTCTTTTCTTGTAGTGTGCTGCATGAAG |
| | | CCCTGCACAATCATTACACACAGAAGTCACTGA |
| | | GCCTGTCCCTGGCAAATGAAGGATCC |
| 18 | Biparatopic antibody construct HC13 (including 5' cloning site (EcoRI) and Kozak sequence, signal sequence and 3' cloning site (BamHI)) | GAATTCGCCACCATGAACTTTGGCCTGAGCCTG |
| | | ATTTTTCTCGTCCTGATCCTGAAGGGCGTGCAG |
| | | TGTGAGGTGCAGCTGGTGGAGAGCGGCGGCG |
| | | GCCTGGTGCAGCCCGGCGGCAGCCTGCGCCTG |
| | | TCCTGCGCCGCCAGCGGCTTCACCTTTGCCGA |
| | | CTACACCATGGACTGGGTGCGCCAGGCTCCCG |
| | | GCAAGGGCCTGGAGTGGGTGGCCGACGTGAAC |
| | | CCCAACAGCGGCGGCAGCATCTACAACCAGCG |
| | | CTTCAAGGGCCGCTTCACCCTGAGCGTGGACC |
| | | GCAGCAAGAACACCCTGTACCTGCAGATGAACA |
| | | GCCTGCGCGCCGAGGACACCGCCGTGTACTAC |
| | | TGCGCCCGCAACCTGGGCCCCAGCTTCTACTTC |
| | | GACTATTGGGGCAGGGCACCCTGGTCACCGT |
| | | GAGCAGCGCTAGCACCAAGGGCCCATCCGTCT |
| | | TCCCCCTGGCACCCTCCTCCAAGAGCACCTCTG |

TABLE 9-continued

Nucleic Acid Sequences

| SEQ ID NO. | Description | Nucleic Acid Sequence |
|---|---|---|
| | | GGGGCACAGCTGCCCTGGGCTGCCTGGTCAAG GACTACTTCCCCGAACCAGTGACCGTGTCCTGG AACTCAGGCGCCCTGACCAGCGGCGTGCACAC CTTCCCTGCTGTCCTGCAGTCCTCAGGACTCTA CTCCCTCAGCAGCGTGGTGACTGTGCCCTCTAG CAGCTTGGGCACCCAGACCTACATCTGCAACGT GAATCACAAGCCCAGCAACACCAAGGTGGACAA GAAAGTTGAGCCCAAATCTTGTGATAAAACTCAT ACCTGCCCCCCTTGTCCTGCACCAGAACTGCTG GGAGGACCATCCGTGTTCCTGTTTCCACCCAAG CCTAAAGACACCCTGATGATTTCCCGCACACCC GAGGTCACTTGCGTGGTCGTGGACGTGTCTCAC GAGGACCCCGAAGTCAAGTTCAACTGGTACGTG GATGGCGTCGAAGTGCATAATGCTAAGACCAAA CCAAGGGAGGAACAGTACAACTCCACATATCGC GTCGTGTCTGTCCTGACTGTGCTGCACCAGGAT TGGCTGAACGGCAAAGAGTATAAGTGCAAAGTG AGCAATAAGGCCCTGCCCGCTCCTATCGAGAAA ACTATTAGCAAGGCTAAAGGGCAGCCTCGCGAA CCACAGGTGTACACCCTGCCTCCATCTCGGGAC GAACTGACTAAGAACCAAGTCAGTCTGACCTGT CTGGTGAAAGGGTTCTATCCTAGCGACATTGCA GTGGAGTGGGAATCCAATGGACAGCCAGAGAA CAATTACAAGACCACACCCCCTGTGCTGGACTC AGATGGAAGCTTCTTTCTGTATAGTAAGCTGACC GTGGATAAATCACGCTGGCAGCAGGGCAACGT CTTTTCTTGTAGTGTGCTGCATGAAGCCCTGCA CAATCATTACACACAGAAGTCACTGAGCCTGTC CCCTGGCGGCGGAGGGAGCGGCGGAGGCTCC GGAGGCGGCAGCGGAGGCGGAGAGGTGCAGC TGGTGGAGTCTGGAGGAGGGCTGGTGCAGCCA GGAGGGTCCCTGAGACTGTCTTGCGCCGCTAG TGGCTTCAACATCAAGGACACCTACATCCACTG GGTGAGACAGGCCCCCGGAAAAGGCCTGGAGT GGGTGGCCAGGATCTACCCTACCACCGGCTAC ACCAGGTACGCCGACAGCGTGAAGGGCAGGTT CACCATCAGCGCCGACACCAGCAAGAACACCG CCTACCTGCAGATGAACAGCCTGAGGGCCGAG GACACCGCCGTGTACTACTGCAGCAGATGGGG CGGCAGCGGCTTCTACGCCATGGACTACTGGG GACAGGGCACACTGGTCACTGTGTCTAGTGCCT CAACAAAGGGGCCTAGCGTGTTTCCACTGGCTC CCTCAAGCAAAAGCACTTCCGGAGGCACCGCT GCACTGGGATGTCTGGTGAAGGACTACTTCCCA GAGCCCGTCACCGTGTCTTGGAACAGTGGGGC TCTGACCAGCGGAGTCCACACATTTCCTGCAGT GCTGCAGTCCTCTGGCCTGTACAGCCTGAGTTC AGTGGTCACAGTCCCAAGCTCCTCTCTGGGGAC CCAGACATATATCTGCAACGTGAATCACAAGCC AAGCAATACTAAAGTCGACAAGAAAGTGGAGCC CAAGAGCTGTTGAAGGATCC |
| 20 | Biparatopic antibody construct HC14 (including 5' cloning site (ECoRI) and Kozak sequence, signal sequence, and 3' cloning site (BamHI)) | GAATTCGCCACCATGAACTTTGGCCTGAGCCTGA TTTTTCTCGTCCTGATCCTGAAGGGCGTGCAGTG TGAGGTGCAGCTGGTGGAGAGCGGCGGCGGCC TGGTGCAGCCCGGCGGCAGCCTGCGCCTGTCCT GCGCCGCCAGCGGCTTCACCTTTGCCGACTACA CCATGGACTGGGTGCGCCAGGCTCCCGGCAAG GGCCTGGAGTGGGTGGCCGACGTGAACCCCAA CAGCGGCGGCAGCATCTACAACCAGCGCTTCAA GGGCCGCTTCACCCTGAGCGTGGACCGCAGCAA GAACACCCTGTACCTGCAGATGAACAGCCTGCG CGCCGAGGACACCGCCGTGTACTACTGCGCCCG CAACCTGGGCCCCAGCTTCTACTTCGACTATTGG GGGCAGGGCACCCTGGTCACCGTGAGCAGCGC TAGCACCAAGGGCCCATCCGTCTTCCCCCTGGC ACCCTCCTCCAAGAGCACCTCTGGGGGCACAGC TGCCCTGGGCTGCCTGGTCAAGGACTACTTCCC CGAACCAGTGACCGTGTCCTGGAACTCAGGCGC CCTGACCAGCGGCGTGCACACCTTCCCTGCTGT CCTGCAGTCCTCAGGACTCTACTCCCTCAGCAG CGTGGTGACTGTGCCCTCTAGCAGCTTGGGCAC CCAGACCTACATCTGCAACGTGAATCACAAGCCC AGCAACACCAAGGTGGACAAGAAAGTTGAGCCC AAATCTTGTGATAAAACTCATACCTGCCCCCCTT |

TABLE 9-continued

Nucleic Acid Sequences

| SEQ ID NO. | Description | Nucleic Acid Sequence |
|---|---|---|
|  |  | GTCCTGCACCAGAACTGCTGGGAGGACCATCCG TGTTCCTGTTTCCACCCAAGCCTAAAGACACCCT GATGATTTCCCGCACACCCGAGGTCACTTGCGT GGTCGTGGACGTGTCTCACGAGGACCCCGAAGT CAAGTTCAACTGGTACGTGGATGGCGTCGAAGT GCATAATGCTAAGACCAAACCAAGGGAGGAACA GTACAACTCCACATATCGCGTCGTGTCTGTCCTG ACTGTGCTGCACCAGGATTGGCTGAACGGCAAA GAGTATAAGTGCAAAGTGAGCAATAAGGCCCTG CCCGCTCCTATCGAGAAAACTATTAGCAAGGCTA AAGGGCAGCCTCGCGAACCACAGGTGTACACCC TGCCTCCATCTCGGGACGAACTGACTAAGAACCA AGTCAGTCTGTGGTGTCTGGTGAAAGGGTTCTAT CCTAGCGACATTGCAGTGGAGTGGGAATCCAAT GGACAGCCAGAGAACAATTACAAGACCACACCC CCTGTGCTGGACTCAGATGGAAGCTTCTTTCTGT ATAGTAAGCTGACCGTGGATAAATCACGCTGGCA GCAGGGCAACGTCTTTTCTTGTAGTGTGCTGCAT GAAGCCCTGCACAATCATTACACACAGAAGTCAC TGAGCCTGTCCCCTGGCAAATGAAGGATCC |
| 22 | Biparatopic antibody construct HC15 (including 5' cloning site (ECoRI) and Kozak sequence, signal sequence, and 3' cloning site (BamHI)) | GAATTCGCCACCATGAACTTTGGCCTGAGCCTG ATTTTTCTCGTCCTGATCCTGAAGGGCGTGCAG TGTGAGGTGCAGCTGGTGGAGTCTGGAGGAGG GCTGGTGCAGCCAGGAGGGTCCCTGAGACTGT CTTGCGCCGCTAGTGGCTTCAACATCAAGGACA CCTACATCCACTGGGTGAGACAGGCCCCCGGA AAAGGCCTGGAGTGGGTGGCCAGGATCTACCC TACCACCGGCTACACCAGGTACGCCGACAGCG TGAAGGGCAGGTTCACCATCAGCGCCGACACC AGCAAGAACACCGCCTACCTGCAGATGAACAGC CTGAGGGCCGAGGACACCGCCGTGTACTACTG CAGCAGATGGGGCGGCAGCGGCTTCTACGCCA TGGACTACTGGGGACAGGGCACACTGGTCACT GTGTCTAGTGCCTCAACAAAGGGGCCTAGCGTG TTTCCACTGGCTCCCTCAAGCAAAAGCACTTCC GGAGGCACCGCTGCACTGGGATGTCTGGTGAA GGACTACTTCCCAGAGCCCGTCACCGTGTCTTG GAACAGTGGGGCTCTGACCAGCGGAGTCCACA CATTTCCTGCAGTGCTGCAGTCCTCTGGCCTGT ACAGCCTGAGTTCAGTGGTCACAGTCCCAAGCT CCTCTCTGGGGACCCAGACATATATCTGCAACG TGAATCACAAGCCAAGCAATACTAAAGTCGACA AGAAAGTGGAGCCCAAGAGCTGTGATAAAACTC ATACCTGCCCCCCTTGTCCTGCACCAGAACTGC TGGGAGGACCATCCGTGTTCCTGTTTCCACCCA AGCCTAAAGACACCCTGATGATTTCCCGCACAC CCGAGGTCACTTGCGTGGTCGTGGACGTGTCT CACGAGGACCCCGAAGTCAAGTTCAACTGGTAC GTGGATGGCGTCGAAGTGCATAATGCTAAGACC AAACCAAGGGAGGAACAGTACAACTCCACATAT CGCGTCGTGTCTGTCCTGACTGTGCTGCACCAG GATTGGCTGAACGGCAAAGAGTATAAGTGCAAA GTGAGCAATAAGGCCCTGCCCGCTCCTATCGAG AAAACTATTAGCAAGGCTAAAGGGCAGCCTCGC GAACCACAGGTGTACACCCTGCCTCCATCTCGG GACGAACTGACTAAGAACCAAGTCAGTCTGAGC TGTGCCGTGAAAGGGTTCTATCCTAGCGACATT GCAGTGGAGTGGGAATCCAATGGACAGCCAGA GAACAATTACAAGACCACACCCCCTGTGCTGGA CTCAGATGGAAGCTTCTTTCTGGTGAGTAAGCT GACCGTGGATAAATCACGCTGGCAGCAGGGCA ACGTCTTTTCTTGTAGTGTGCTGCATGAAGCCCT GCACAATCATTACACACAGAAGTCACTGAGCCT GTCCCCTGGCAAATGAAGGATCC |
| 38 | EcoRI-Kozak-Pert_$V_{H\_V16x}C_{H1}Fc_{ML}$ | GAATTCGCCACCATGAACTTTGGCCTGAGCCTG ATTTTTCTCGTCCTGATCCTGAAGGGCGTGCAG TGTGAGGTGCAGCTGGTGGAGAGCGGCGGCG GCCTGGTGCAGCCCGGCGGCAGCCTGCGCCTG TCCTGCGCCGCCAGCGGCTTCACCTTTACCGAC TACACCATGGACTGGGTGCGCCAGGCTCCCGG CAAGGGCCTGGAGTGGGTGGCCGACGTGAACC CCAACAGCGGCGGCAGCATCTACAACCAGCGC TTCAAGGGCCGCTTCACCCTGAGCGTGGACCG |

TABLE 9-continued

Nucleic Acid Sequences

| SEQ ID NO. | Description | Nucleic Acid Sequence |
|---|---|---|
| | | CAGCAAGAACACCCTGTACCTGCAGATGAACAG CCTGCGCGCCGAGGACACCGCCGTGTACTACT GCGCCCGCAACCTGGGCCCCAGCTTCTACTTC GACTATTGGGGCAGGGCACCCTGGTCACCGT GAGCAGCGCTAGCACCAAGGGCCCATCCGTCT TCCCCCTGGCACCCTCCTCCAAGAGCACCTCTG GGGGCACAGCTGCCCTGGGCTGCCTGGTCAAG GACTACTTCCCCGAACCAGTGACCGTGTCCTGG AACTCAGGCGCCCTGACCAGCGGCGTGCACAC CTTCCCTGCTGTCCTGCAGTCCTCAGGACTCTA CTCCCTCAGCAGCGTGGTGACTGTGCCCTCTAG CAGCTTGGGCACCCAGACCTACATCTGCAACGT GAATCACAAGCCCAGCAACACCAAGGTGGACAA GAAAGTTGAGCCCAAATCTTGTGACAAA |
| 39 | Tra_V$_{H\text{-}VNT\_DS}$C$_{H1}$ | GAGGTGCAGCTGGTGGAGTCTGGAGGAGGGCT GGTGCAGCCAGGAGGGTCCCTGAGACTGTCTT GCGCCGCTAGTGGCTTCAACATCAAGGACACCT ACATCCACTGGGTGAGACAGGCCCCCGGAAAA GGCCTGGAGTGGGTGGCCAGGATCTACCCTAC CACCGGCTACACCAGGTACGCCGACAGCGTGA AGGGCAGGTTCACCATCAGCGCCGACACCAGC AAGAACACCGCCTACCTGCAGATGAACAGCCTG AGGGCCGAGGACACCGCCGTGTACTACTGCAG CAGATGGGGCGGCAGCGGCTTCTACGCCATGG ACTACTGGGGACAGGGCACACTGGTCACTGTGT CTAGTGCCTCAACAAAGGGGCCTAGCGTGTTTC CACTGGCTCCCTCAAGCAAAAGCACTTCCGGAG GCACCGCTGCACTGGGATGTCTGGTGAAGGAC TACTTCCCAGAGCCCGTCACCGTGTCTTGGAAC AGTGGGGCTCTGACCAGCGGAGTCCACACATTT CCTGCAGTGCTGCAGTCCTCTGGCCTGTACAGC CTGAGTTCAGTGGTCACAGTCCCAAGCTCCTCT CTGGGGACCCAGACATATATCTGCAACGTGAAT CACAAGCCAAGCAATACTAAAGTCGACAAGAAA GTGGAGCCCAAGAGCTGTGATAAAACTCATACC TGCCCCCCTTGTCCTGCACCAGAACTGCTGGGA GGACCATCCGTGTTCCTGTTTCCACCCAAGCCT AAAGACACCCTGATGATTTCCCGCACACCCGAG GTCACTTGCGTGGTCGTGGACGTGTCTCACGAG GACCCCGAAGTCAAGTTCAACTGGTACGTGGAT GGCGTCGAAGTGCATAATGCTAAGACCAAACCA AGGGAGGAACAGTACAACTCCACATATCGCGTC GTGTCTGTCCTGACTGTGCTGCACCAGGATTGG CTGAACGGCAAAGAGTATAAGTGCAAAGTGAGC AATAAGGCCCTGCCCGCTCCTATCGAGAAAACT ATTAGCAAGGCTAAAGGGCAGCCTCGCGAACCA CAGGTGTACACCCTGCCTCCATCTCGGGAGGAA ATGACTAAGAACCAAGTCAGTCTGACCTGTCTG GTGAAAGGGTTCTATCCTAGCGACATTGCAGTG GAGTGGGAATCCAATGGACAGCCAGAGAACAAT TACAAGACCACACCCCCTGTGCTGGACTCAGAT GGAAGCTTCTTTCTGTATAGTAAGCTGACCGTG GATAAATCACGCTGGCAGCAGGGCAACGTCTTT TCTTGTAGTGTGCTGCATGAAGCCCTGCACAAT CATTACACACAGAAGTCACTGAGCCTGTCCCCT GGCAAATGAAGGATCC |
| 40 | Pert_HC_v2x_Tra_HC_ vNT_DS_ML | GAATTCGCCACCATGAACTTTGGCCTGAGCCTG ATTTTTCTCGTCCTGATCCTGAAGGGCGTGCAG TGTGAGGTGCAGCTGGTGGAGAGCGGCGGCG GCCTGGTGCAGCCCGGCGGCAGCCTGCGCCTG TCCTGCGCCGCCAGCGGCTTCACCTTTACCGAC TACACCATGGACTGGGTGCGCCAGGCTCCCGG CAAGGGCCTGGAGTGGGTGGCCGACGTGAACC CCAACAGCGGCGGCAGCATCTACAACCAGCGC TTCAAGGGCCGCTTCACCCTGAGCGTGGACCG CAGCAAGAACACCCTGTACCTGCAGATGAACAG CCTGCGCGCCGAGGACACCGCCGTGTACTACT GCGCCCGCAACCTGGGCCCCAGCTTCTACTTC GACTATTGGGGCAGGGCACCCTGGTCACCGT GAGCAGCGCTAGCACCAAGGGCCCATCCGTCT TCCCCCTGGCACCCTCCTCCAAGAGCACCTCTG GGGGCACAGCTGCCCTGGGCTGCCTGGTCAAG GACTACTTCCCCGAACCAGTGACCGTGTCCTGG |

TABLE 9-continued

Nucleic Acid Sequences

| SEQ ID NO. | Description | Nucleic Acid Sequence |
|---|---|---|
| | | AACTCAGGCGCCCTGACCAGCGGCGTGCACAC<br>CTTCCCTGCTGTCCTGCAGTCCTCAGGACTCTA<br>CTCCCTCAGCAGCGTGGTGACTGTGCCCTCTAG<br>CAGCTTGGGCACCCAGACCTACATCTGCAACGT<br>GAATCACAAGCCCAGCAACACCAAGGTGGACAA<br>GAAAGTTGAGCCCAAATCTTGTGATAAAACTCAT<br>ACCTGCCCCCCTTGTCCTGCACCAGAACTGCTG<br>GGAGGACCATCCGTGTTCCTGTTTCCACCCAAG<br>CCTAAAGACACCCTGATGATTTCCCGCACACCC<br>GAGGTCACTTGCGTGGTCGTGGACGTGTCTCAC<br>GAGGACCCCGAAGTCAAGTTCAACTGGTACGTG<br>GATGGCGTCGAAGTGCATAATGCTAAGACCAAA<br>CCAAGGGAGGAACAGTACAACTCCACATATCGC<br>GTCGTGTCTGTCCTGACTGTGCTGCACCAGGAT<br>TGGCTGAACGGCAAAGAGTATAAGTGCAAAGTG<br>AGCAATAAGGCCCTGCCCGCTCCTATCGAGAAA<br>ACTATTAGCAAGGCTAAAGGGCAGCCTCGCGAA<br>CCACAGGTGTACACCCTGCCTCCATCTCGGGAG<br>GAAATGACTAAGAACCAAGTCAGTCTGACCTGT<br>CTGGTGAAAGGGTTCTATCCTAGCGACATTGCA<br>GTGGAGTGGGAATCCAATGGACAGCCAGAGAA<br>CAATTACAAGACCACACCCCCTGTGCTGGACTC<br>AGATGGAAGCTTCTTTCTGTATAGTAAGCTGACC<br>GTGGATAAATCACGCTGGCAGCAGGGCAACGT<br>CTTTTCTTGTAGTGTGCTGCATGAAGCCCTGCA<br>CAATCATTACACACAGAAGTCACTGAGCCTGTC<br>CCCTGGCGGCGGAGGGAGCGGCGGAGGCTCC<br>GGAGGCGGCAGCGGAGGCGGAGAGGTGCAGC<br>TGGTGGAGTCTGGAGGAGGGCTGGTGCAGCCA<br>GGAGGGTCCCTGAGACTGTCTTGCGCCGCTAG<br>TGGCTTCAACATCAAGGACACCTACATCCACTG<br>GGTGAGACAGGCCCCCGGAAAAGGCCTGGAGT<br>GGGTGGCCAGGATCTACCCTACCACCGGCTAC<br>ACCAGGTACGCCGACAGCGTGAAGGGCAGGTT<br>CACCATCAGCGCCGACACCAGCAAGAACACCG<br>CCTACCTGCAGATGAACAGCCTGAGGGCCGAG<br>GACACCGCCGTGTACTACTGCAGCAGATGGGG<br>CGGCAGCGGCTTCTACGCCATGGACTACTGGG<br>GACAGGGCACACTGGTCACTGTGTCTAGTGCCT<br>CAACAAAGGGGCCTAGCGTGTTTCCACTGGCTC<br>CCTCAAGCAAAAGCACTTCCGGAGGCACCGCT<br>GCACTGGGATGTCTGGTGAAGGACTACTTCCCA<br>GAGCCCGTCACCGTGTCTTGGAACAGTGGGGC<br>TCTGACCAGCGGAGTCCACACATTTCCTGCAGT<br>GCTGCAGTCCTCTGGCCTGTACAGCCTGAGTTC<br>AGTGGTCACAGTCCCAAGCTCCTCTCTGGGGAC<br>CCAGACATATATCTGCAACGTGAATCACAAGCC<br>AAGCAATACTAAAGTCGACAAGAAAGTGGAGCC<br>CAAGAGCTGT |
| 41 | Pert_HC_v16x Knob | GAATTCGCCACCATGAACTTTGGCCTGAGCCTG<br>ATTTTTCTCGTCCTGATCCTGAAGGGCGTGCAG<br>TGTGAGGTGCAGCTGGTGGAGAGCGGCGGCG<br>GCCTGGTGCAGCCCGGCGGCAGCCTGCGCCTG<br>TCCTGCGCCGCCAGCGGCTTCACCTTTACCGAC<br>TACACCATGGACTGGGTGCGCCAGGCTCCCGG<br>CAAGGGCCTGGAGTGGGTGGCCGACGTGAACC<br>CCAACAGCGGCGGCAGCATCTACAACCAGCGC<br>TTCAAGGGCCGCTTCACCCTGAGCGTGGACCG<br>CAGCAAGAACACCCTGTACCTGCAGATGAACAG<br>CCTGCGCGCCGAGGACACCGCCGTGTACTACT<br>GCGCCCGCAACCTGGGCCCCAGCTTCTACTTC<br>GACTATTGGGGCAGGGCACCCTGGTCACCGT<br>GAGCAGCGCTAGCACCAAGGGCCCATCCGTCT<br>TCCCCCTGGCACCCTCCTCCAAGAGCACCTCTG<br>GGGGCACAGCTGCCCTGGGCTGCCTGGTCAAG<br>GACTACTTCCCCGAACCAGTGACCGTGTCCTGG<br>AACTCAGGCGCCCTGACCAGCGGCGTGCACAC<br>CTTCCCTGCTGTCCTGCAGTCCTCAGGACTCTA<br>CTCCCTCAGCAGCGTGGTGACTGTGCCCTCTAG<br>CAGCTTGGGCACCCAGACCTACATCTGCAACGT<br>GAATCACAAGCCCAGCAACACCAAGGTGGACAA<br>GAAAGTTGAGCCCAAATCTTGTGATAAAACTCAT<br>ACCTGCCCCCCTTGTCCTGCACCAGAACTGCTG<br>GGAGGACCATCCGTGTTCCTGTTTCCACCCAAG |

TABLE 9-continued

Nucleic Acid Sequences

| SEQ ID NO. | Description | Nucleic Acid Sequence |
|---|---|---|
| | | CCTAAAGACACCCTGATGATTTCCCGCACACCC<br>GAGGTCACTTGCGTGGTCGTGGACGTGTCTCAC<br>GAGGACCCCGAAGTCAAGTTCAACTGGTACGTG<br>GATGGCGTCGAAGTGCATAATGCTAAGACCAAA<br>CCAAGGGAGGAACAGTACAACTCCACATATCGC<br>GTCGTGTCTGTCCTGACTGTGCTGCACCAGGAT<br>TGGCTGAACGGCAAAGAGTATAAGTGCAAAGTG<br>AGCAATAAGGCCCTGCCCGCTCCTATCGAGAAA<br>ACTATTAGCAAGGCTAAAGGGCAGCCTCGCGAA<br>CCACAGGTGTACACCCTGCCTCCATCTCGGGAG<br>GAAATGACTAAGAACCAAGTCAGTCTGTGGTGT<br>CTGGTGAAAGGGTTCTATCCTAGCGACATTGCA<br>GTGGAGTGGGAATCCAATGGACAGCCAGAGAA<br>CAATTACAAGACCACACCCCCTGTGCTGGACTC<br>AGATGGAAGCTTCTTTCTGTATAGTAAGCTGACC<br>GTGGATAAATCACGCTGGCAGCAGGGCAACGT<br>CTTTTCTTGTAGTGTGCTGCATGAAGCCCTGCA<br>CAATCATTACACACAGAAGTCACTGAGCCTGTC<br>CCCTGGCAAATGAAGGATCC |
| 42 | Tras_HC_hole | GAATTCGCCACCATGAACTTTGGCCTGAGCCT<br>GATTTTTCTCGTCCTGATCCTGAAGGGCGTGCA<br>GTGTGAGGTGCAGCTGGTGGAGTCTGGAGGA<br>GGGCTGGTGCAGCCAGGAGGGTCCCTGAGAC<br>TGTCTTGCGCCGCTAGTGGCTTCAACATCAAG<br>GACACCTACATCCACTGGGTGAGACAGGCCCC<br>CGGAAAAGGCCTGGAGTGGGTGGCCAGGATC<br>TACCCTACCACCGGCTACACCAGGTACGCCGA<br>CAGCGTGAAGGGCAGGTTCACCATCAGCGCC<br>GACACCAGCAAGAACACCGCCTACCTGCAGAT<br>GAACAGCCTGAGGGCCGAGGACACCGCCGTG<br>TACTACTGCAGCAGATGGGGCGGCAGCGGCTT<br>CTACGCCATGGACTACTGGGGACAGGGCACAC<br>TGGTCACTGTGTCTAGTGCCTCAACAAAGGGG<br>CCTAGCGTGTTTCCACTGGCTCCCTCAAGCAA<br>AAGCACTTCCGGAGGCACCGCTGCACTGGGAT<br>GTCTGGTGAAGGACTACTTCCCAGAGCCCGTC<br>ACCGTGTCTTGGAACAGTGGGGCTCTGACCAG<br>CGGAGTCCACACATTTCCTGCAGTGCTGCAGT<br>CCTCTGGCCTGTACAGCCTGAGTTCAGTGGTC<br>ACAGTCCCAAGCTCCTCTCTGGGGACCCAGAC<br>ATATATCTGCAACGTGAATCACAAGCCAAGCAA<br>TACTAAAGTCGACAAGAAAGTGGAGCCCAAGA<br>GCTGTGATAAAACTCATACCTGCCCCCCTTGTC<br>CTGCACCAGAACTGCTGGGAGGACCATCCGTG<br>TTCCTGTTTCCACCCAAGCCTAAAGACACCCTG<br>ATGATTTCCCGCACACCCGAGGTCACTTGCGT<br>GGTCGTGGACGTGTCTCACGAGGACCCCGAA<br>GTCAAGTTCAACTGGTACGTGGATGGCGTCGA<br>AGTGCATAATGCTAAGACCAAACCAAGGGAGG<br>AACAGTACAACTCCACATATCGCGTCGTGTCTG<br>TCCTGACTGTGCTGCACCAGGATTGGCTGAAC<br>GGCAAAGAGTATAAGTGCAAAGTGAGCAATAA<br>GGCCCTGCCCGCTCCTATCGAGAAAACTATTA<br>GCAAGGCTAAAGGGCAGCCTCGCGAACCACA<br>GGTGTACACCCTGCCTCCATCTCGGGAGGAAA<br>TGACTAAGAACCAAGTCAGTCTGAGCTGTGCC<br>GTGAAAGGGTTCTATCCTAGCGACATTGCAGT<br>GGAGTGGGAATCCAATGGACAGCCAGAGAACA<br>ATTACAAGACCACACCCCCTGTGCTGGACTCA<br>GATGGAAGCTTCTTTCTGGTGAGTAAGCTGAC<br>CGTGGATAAATCACGCTGGCAGCAGGGCAACG<br>TCTTTTCTTGTAGTGTGCTGCATGAAGCCCTGC<br>ACAATCATTACACACAGAAGTCACTGAGCCTGT<br>CCCCTGGCAAATGAAGGATCC |
| 43 | Tras-optimized Fc | ATGAACTTTGGCCTGAGCCTGATTTTTCTCGTCC<br>TGATCCTGAAGGGCGTGCAGTGTGAGGTGCAG<br>CTGGTGGAGAGCGGCGGCGCCTGGTGCAGC<br>CCGGCGGCAGCCTGCGCCTGTCCTGCGCCGCC<br>AGCGGCTTCACCTTTGCCGACTACACCATGGAC<br>TGGGTGCGCCAGGCTCCCGGCAAGGGCCTGGA<br>GTGGGTGGCCGACGTGAACCCCAACAGCGGCG<br>CCAGCATCTACAACCAGCGCTTCAAGGGCCGCT<br>TCACCCTGAGCGTGGACCGCAGCAAGAACACC |

TABLE 9-continued

Nucleic Acid Sequences

| SEQ ID NO. | Description | Nucleic Acid Sequence |
|---|---|---|
|  |  | CTGTACCTGCAGATGAACAGCCTGCGCGCCGA GGACACCGCCGTGTACTACTGCGCCCGCAACC TGGGCCCCAGCTTCTACTTCGACTATTGGGGGC AGGGCACCCTGGTCACCGTGAGCAGCGCTAGC ACCAAGGGCCCATCCGTCTTCCCCCTGGCACC CTCCTCCAAGAGCACCTCTGGGGGCACAGCTG CCCTGGGCTGCCTGGTCAAGGACTACTTCCCC GAACCAGTGACCGTGTCCTGGAACTCAGGCGC CCTGACCAGCGGCGTGCACACCTTCCCTGCTGT CCTGCAGTCCTCAGGACTCTACTCCCTCAGCAG CGTGGTGACTGTGCCCTCTAGCAGCTTGGGCA CCCAGACCTACATCTGCAACGTGAATCACAAGC CCAGCAACACCAAGGTGGACAAGAAAGTTGAGC CCAAATCTTGTGACAAAGGCGGAGGGAGCGGC GGAGGCTCCGGAGGCGGCAGCGGAGGCGGA |
| 44 | gTra_HC_vNT_DT_ML minus signal peptide | GAGGTGCAGCTGGTGGAGTCTGGAGGAGGGCT GGTGCAGCCAGGAGGGTCCCTGAGACTGTCTT GCGCCGCTAGTGGCTTCAACATCAAGGACACCT ACATCCACTGGGTGAGACAGGCCCCCGGAAAA GGCCTGGAGTGGGTGGCCAGGATCTACCCTAC CACCGGCTACACCAGGTACGCCGACAGCGTGA AGGGCAGGTTCACCATCAGCGCCGACACCAGC AAGAACACCGCCTACCTGCAGATGAACAGCCTG AGGGCCGAGGACACCGCCGTGTACTACTGCAG CAGATGGGGCGGCACCGGCTTCTACGCCATGG ACTACTGGGGACAGGGCACACTGGTCACTGTGT CTAGTGCCTCAACAAAGGGGCCTAGCGTGTTTC CACTGGCTCCCTCAAGCAAAAGCACTTCCGGAG GCACCGCTGCACTGGGATGTCTGGTGAAGGAC TACTTCCCAGAGCCCGTCACCGTGTCTTGGAAC AGTGGGGCTCTGACCAGCGGAGTCCACACATTT CCTGCAGTGCTGCAGTCCTCTGGCCTGTACAGC CTGAGTTCAGTGGTCACAGTCCCAAGCTCCTCT CTGGGGACCCAGACATATATCTGCAACGTGAAT CACAAGCCAAGCAATACTAAAGTCGACAAGAAA GTGGAGCCCAAGAGCTGTGATAAAACTCATACC TGCCCCCCTTGTCCTGCACCAGAACTGCTGGGA GGACCATCCGTGTTCCTGTTTCCACCCAAGCCT AAAGACACCCTGATGATTTCCCGCACACCCGAG GTCACTTGCGTGGTCGTGGACGTGTCTCACGAG GACCCCGAAGTCAAGTTCAACTGGTACGTGGAT GGCGTCGAAGTGCATAATGCTAAGACCAAACCA AGGGAGGAACAGTACAACTCCACATATCGCGTC GTGTCTGTCCTGACTGTGCTGCACCAGGATTGG CTGAACGGCAAAGAGTATAAGTGCAAAGTGAGC AATAAGGCCCTGCCCGCTCCTATCGAGAAAACT ATTAGCAAGGCTAAAGGGCAGCCTCGCGAACCA CAGGTGTACACCCTGCCTCCATCTCGGGAGGAA ATGACTAAGAACCAAGTCAGTCTGACCTGTCTG GTGAAAGGGTTCTATCCTAGCGACATTGCAGTG GAGTGGGAATCCAATGGACAGCCAGAGAACAAT TACAAGACCACACCCCCTGTGCTGGACTCAGAT GGAAGCTTCTTTCTGTATAGTAAGCTGACCGTG GATAAATCACGCTGGCAGCAGGGCAACGTCTTT TCTTGTAGTGTGCTGCATGAAGCCCTGCACAAT CATTACACACAGAAGTCACTGAGCCTGTCCCCT GGCAAATGAAGGATCC |

SEQUENCE LISTING

This application contains a sequence listing having the filename 1403346-00002_Sequence_Listing, which is 113 kilobytes in size, and was created on Apr. 9, 2018. The entire content of this sequence listing is herein incorporated by reference.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A multiparatopic antibody construct comprising
   (1) a modified pertuzumab heavy chain variable region comprising:
      1) a T30A mutation; or
      2) a T30A and a G56A mutation; and
   (2) a modified trastuzumab heavy chain variable region comprising:
      a N54T and a D98S mutation; and
   (3) a common light chain comprising a modified trastuzumab light chain, wherein the modified trastuzumab light chain comprises:
      1) a N30S and a S56Y mutation; or
      2) a N30S and a S56Y and a T94W mutation; and
   wherein all amino acid modifications to SEQ ID NOs: 3, 7, and 5 are based on the Kabat numbering system, wherein the trastuzumab light chain variable region consists of the amino acid sequence of SEQ ID NO: 5 and the pertuzumab heavy chain variable region consists of the amino acid sequence of SEQ ID NO: 3 and the trastuzumab heavy chain variable region consists of the amino acid sequence of SEQ ID NO: 7.

2. The multiparatopic antibody construct of claim 1 that is biparatopic.

3. The biparatopic antibody construct of claim 2 having a Fab-Ig format.

4. The biparatopic antibody construct of claim 2 having a Ig-Fab format.

5. The biparatopic antibody construct of claim 2 having a heterodimer Ig format.

6. The biparatopic antibody construct of claim 2 having a modified Fc region comprising a substitution consisting of M428L, based on the Eu numbering system.

7. The multiparatopic antibody construct of claim 2, wherein the Fc of the multiparatopic antibody construct contains an Fc with increased antibody-dependent cellular cytotoxicity (ADCC), antibody-dependent cellular phagocytosis (ADCP) or complement-dependent cytotoxicty (CDC) activity.

8. The multiparatopic antibody construct of claim 2, wherein the biparatopic antibody construct is an afucosylated antibody.

9. The multiparatopic antibody construct of claim 8, wherein the afucosylated antibody is obtained by producing the biparatopic molecules in host cells that are defective in fucosylation.

10. The multiparatopic antibody construct of claim 9, wherein the defection in fucosylation is due to knock out of the FUT8 gene.

11. The multiparatopic antibody construct of claim 1, wherein:
   (1) the modified pertuzumab heavy chain variable region comprises the T30A mutation;
   (2) the modified trastuzumab heavy chain variable region comprises the N54T and the D98S mutations; and
   (3) the common light chain comprising the modified trastuzumab light chain comprises the N30S and the S56Y mutations.

12. The multiparatopic antibody construct of claim 11 having a heterodimer Ig format.

13. The multiparatopic antibody construct of claim 11, wherein the multiparatopic antibody construct is T54, having a structure of knob-into-holes, wherein T54 consists of:
   1) two heavy chains consisting of the amino acid sequences of SEQ ID NO: 19 (pertuzumab heavy chain) and SEQ ID NO: 21 (trastuzumab heavy chain), respectively; and
   2) the common light chain comprising the modified trastuzumab light chain, wherein the modified trastuzumab light chain consists of the S56Y and the N30S mutations.

14. The multiparatopic antibody construct of claim 13, wherein the Fc region of the knob consisting of a M428L and T366W mutation, and the Fc region of the hole consisting of a M428L, T366S, L368A and Y407V mutation, based on the Eu numbering system.

15. The multiparatopic antibody construct of claim 13, wherein the multiparatopic antibody construct is an afucosylated antibody.

16. The multiparatopic antibody construct of claim 11 having a structure of knob-into-holes, and the Fc region of the knob consisting of a M428L and T366W mutation, and the Fc region of the hole consisting of a M428L, T366S, L368A and Y407V mutation, based on the Eu numbering system.

17. The multiparatopic antibody construct of claim 11, wherein the multiparatopic antibody construct is an afucosylated antibody.

18. A composition comprising the multiparatopic antibody construct of claim 1, and a pharmaceutically acceptable carrier or excipient.

* * * * *